United States Patent
Idone et al.

(10) Patent No.: US 11,945,872 B2
(45) Date of Patent: Apr. 2, 2024

(54) ANTI-ACVR1 ANTIBODIES AND USES THEREOF

(71) Applicant: Regeneron Pharmaceuticals, Inc., Tarrytown, NY (US)

(72) Inventors: Vincent J. Idone, Ridgefield, CT (US); Sarah J. Hatsell, Nyack, NY (US); Aris N. Economides, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 184 days.

(21) Appl. No.: 17/172,856

(22) Filed: Feb. 10, 2021

(65) Prior Publication Data

US 2021/0253716 A1  Aug. 19, 2021

Related U.S. Application Data

(60) Provisional application No. 62/975,047, filed on Feb. 11, 2020, provisional application No. 63/030,131, filed on May 26, 2020.

(51) Int. Cl.
| | |
|---|---|
| *C07K 16/28* | (2006.01) |
| *A61K 39/00* | (2006.01) |
| *A61K 39/395* | (2006.01) |
| *A61K 45/06* | (2006.01) |
| *A61P 7/06* | (2006.01) |
| *A61P 19/00* | (2006.01) |

(52) U.S. Cl.
CPC ...... *C07K 16/2863* (2013.01); *A61K 39/3955* (2013.01); *A61K 45/06* (2013.01); *A61P 7/06* (2018.01); *A61P 19/00* (2018.01); *A61K 2039/505* (2013.01); *C07K 2317/21* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,596,541 B2 | 7/2003 | Murphy et al. |
| 7,582,298 B2 | 9/2009 | Stevens et al. |
| 8,246,995 B2 | 8/2012 | Dai et al. |
| 8,257,740 B1 | 9/2012 | Sung et al. |
| 8,859,752 B2 | 10/2014 | Kaplan et al. |
| 10,106,852 B2 | 10/2018 | Kaplan et al. |
| 10,428,148 B2 | 10/2019 | Katagiri et al. |
| 2004/0101920 A1 | 5/2004 | Radziejewski et al. |
| 2010/0331527 A1 | 12/2010 | Davis et al. |
| 2011/0195454 A1 | 8/2011 | McWhirter et al. |
| 2014/0243504 A1 | 8/2014 | Davis et al. |
| 2015/0037339 A1 | 2/2015 | Gromada et al. |
| 2018/0118835 A1 | 5/2018 | Katagiri et al. |
| 2021/0009709 A1 | 1/2021 | Katagiri et al. |

FOREIGN PATENT DOCUMENTS

| | | |
|---|---|---|
| EP | 3252074 A1 | 12/2017 |
| WO | 2005/103081 A2 | 11/2005 |
| WO | 2008/108918 A1 | 9/2008 |
| WO | 2019/172165 A1 | 9/2019 |
| WO | 2020/086730 A1 | 4/2020 |
| WO | 2020/118011 A1 | 6/2020 |
| WO | 2021/020282 A1 | 2/2021 |

OTHER PUBLICATIONS

Fenton et al. Rheostat positions: A new classification of protein positions relevant to pharmacogenomics Medicinal Chemistry Research 29:1133-1146; (2020). (Year: 2020).*
Bhattacharya et al. Impact of genetic variation on three dimensional structure and function of proteins PLoS One 12(3): e0171355; (2017). (Year: 2017).*
Tokuriki et al. Stability effects of mutations and protein evolvability. Curr. Opin. Struc. Biol. 19:596-604; (2009). (Year: 2009).*
Guo et al. Protein tolerance to random amino acid change. PNAS USA 101(25):9205-10; (2004). (Year: 2004).*
Alaoui-Ismaili et al. Design of second generation therapeutic recombinant bone morphogenetic proteins. Cytokine Growth Factor Rev. 20(5-6):501-7 (2009). (Year: 2009).*
Hatsell et al. ACVR1 antibodies exacerbate heterotopic ossification in fibrodysplasia ossificans progressiva (FOP). Journal of Bone and Mineral Research, Abstract. vol. 37, No. Suppl. 1, pp. 197; (Feb. 2022). (Year: 2022).*
Lees-Shepard et al. An anti-ACVR! antibody exacerbates heterotopic ossification by fibro-adipogenic progenitors in fibrodysplasia ossificans progressiva mice. The Journal of Clinical Investigation vol. 132(12)e153795, pp. 1-15 (2022). (Year: 2022).*
International Search Report and Written Opinion for International Application No. PCT/US2021/018427, dated Jun. 7, 2021, 18 pages total.
Agarwal et al., "Strategic Targeting of Multiple BMP Receptors Prevents Trauma-Induced Heterotopic Ossification," Molecular Therapy, vol. 25, No. 8, pp. 1974-1987 (Aug. 2017).

(Continued)

*Primary Examiner* — Elizabeth C. Kemmerer
*Assistant Examiner* — Regina M DeBerry
(74) *Attorney, Agent, or Firm* — Merchant & Gould P.C.

(57) ABSTRACT

The present invention provides monoclonal antibodies that bind to the Activin A type I receptor (ACVR1) protein, and methods of use thereof. In various embodiments of the invention, the antibodies are fully human antibodies that bind to ACVR1. In some embodiments, the antibodies of the invention are useful for inhibiting ACVR1-mediated bone morphogenetic protein (BMP) signal transduction, thus providing a means of treating or preventing a disease, disorder or condition associated with ACVR1.

21 Claims, 4 Drawing Sheets
Specification includes a Sequence Listing.

(56) References Cited

OTHER PUBLICATIONS

Al-Lazikani et al., "Standard Conformations for the Canonical Structures of Immunoglobulins," J Mol Biol, 273(4):927-948 (1997).
Altschul et al., "Basic Local Alignment Search Tool," J. Mol. Biol., vol. 215, pp. 403-410 (1990).
Altschul et al., "Gapped BLAST and PSI-BLAST: a new generation of protein database search programs," Nucleic Acids Research, vol. 25, No. 17, pp. 3389-3402 (1997).
Arruebo et al., "Antibody-Conjugated Nanoparticles for Biomedical Applications," Journal of Nanomaterials, vol. 2009, Article ID 439389, 24 pages, doi: 10.1155/2009/439389.
Buczkowicz et al, "Genomic analysis of diffuse intrinsic pontine gliomas identifies three molecular subgroups and recurrent activating ACVR1 mutations," Nat Genet. May 2014; 46(5): 451-456. doi:10.1038/ng.2936.
Cappato et al., "The Horizon of a Therapy for Rare Genetic Diseases: A "Druggable" Future for Fibrodysplasia Ossificans Progressiva," Int. J. Mol. Sci. 2018, 19, 989; doi:10.3390/ijms19040989.
Ehring, "Hydrogen Exchange/Electrospray Ionizatino Mass Spectrometry Studies of Structural Features of Proteins and Protein/Protein Interactions," Analytical Biochemistry; 267(2):252-259 (Feb. 15, 1999).
Engen et al., "Investigating protein structure and dynamics by hydrogen exchange MS," Analycial Chemistry, vol. 73, No. 9, pp. 256A-265A (2001).
Gonnet et al., "Exhaustive Matching of the Entire Protein Sequence Database," Science, 256(5062):1443-1445 (Jun. 5, 1992).
Hatsell et al., "ACVR1R206H receptor mutation causes fibrodysplasia ossificans progressiva by imparting responsiveness to activin A," Sci Transl Med. Sep. 2, 2015; 7(303): 303ra137.doi10.1126/scitranslmed.aac4358.
Hochleitner et al., "Characterization of a discontinuous epitope of the human immunodeficiency virus (HIV) core protein p24 by epitope excision and differential chemical modification followed by mass spectrometric peptide mapping analysis," Protein Science, vol. 9, pp. 487-496 (2000).
Junghans et al., "Anti-Tac-H, a Humanized Antibody to the Interleukin 2 Receptor with New Features for Immunotherapy in Malignant and Immune Disorders," Cancer Ressearch, vol. 50, pp. 1495-1502 (Mar. 1, 1990).
Kabat et al., "Sequences of Proteins of Immunological Interest," National Institutes of Health (U.S.), 6 pages (1991).
Kazane et al., "Self-Assembled Antibody Multimers through Peptide Nucleic Acid Conjugation," J Am Chem Soc., 135(1):340-346 (Jan. 9, 2013).
Klein et al., "Progress in overcoming the chain association issue in bispecific heterodimeric IgG antibodies," mAbs, 4:6, 653-663, DOI: 10.4161/mabs.21379 (2012).
Kufer et al., "A revival of bispecific antibodies," Trends Biotechnol, 22(5):238-244 (May 2004).
Langer, "New Methods of Drug Delivery," Science, 249:1527-1533 (Sep. 28, 1990).
Mao et al., "Tamoxifen Inhibits the Progression of Trauma-Induced Heterotopic Ossification in Mice," Med Sci Monit, 2019; 25:7872-7881; DOI: 10.12659/MSM.916733.
Martin et al., "Modeling antibody hypervariable loops: A combined algorithm," Proc. Natl. Acad. Sci. USA, vol. 86, pp. 9268-9272 (Dec. 1989).
Massagué, "TGF-β Signal Transduction," Annu. Rev. Biochem., vol. 67, pp. 753-791 (1998).
Massagué et al., "Smad transcription factors," Genes & Development, vol. 19, pp. 2783-2810 (2005).
Padlan et al., "Identification of specificity-determining residues in antibodies," FASEB J. 9:133-139 (1995).
Pagani et al., "Hepcidin and Anemia: A Tight Relationship," Front. Physiol. 10:1294. doi: 10.3389/fphys.2019.01294.
Parodi et al., "Established and Emerging Strategies for Drug Delivery Across the Blood-Brain Barrier in Brain Cancer," Pharmaceutics 2019, 11, 245; doi:10.3390/pharmaceutics11050245.
Pearson, "Using the FASTA Program to Search Protein and DNA Sequence Databases," Methods in Molecular Biology, 24(Ch 26): 307-331 (1994).
Petrie et al., "Novel Mutations in ACVR1 Result in Atypical Features in Two Fibrodysplasia Ossificans Progressiva Patients," PLoS One 4(3): e5005. doi:10.1371/journal.pone.0005005.
Pignolo et al. "Fibrodysplasia Ossificans Progressiva: Clinical and Genetic Aspects," Orphanet Journal of Rare Diseases 2011, 6:80.
Powell et al. "Compendium of excipients for parenteral formulations" PDA (1998) J Pharm Sci Technol 52:238-311.
Reddy et al., "Elimination of Fc Receptor-Dependent Effector Functions of a Modified IgG4 Monoclonal Antibody to Human CD4," The Journal of Immunology, vol. 164, pp. 1925-1933 (2000).
Reineke, "Antibody Epitope Mapping Using Arrays of Synthetic Peptides," Methods in Molecular Biology, 248(26):443-463 (2004).
Sangkhae et al., "Regulation of the Iron Homeostatic Hormone Hepcidin," Adv Nutr 2017;8:126-36; doi:10.3945/an.116.013961.
Shields et al., "Lack of Fucose on Human IgG1 N-Linked Oligosaccharide Improves Binding to Human Fc γRIII and Antibody-dependent Cellular Toxicity," The Journal of Biological Chemistry, vol. 277, No. 30, pp. 26733-26740 (2002).
Shore et al., Nat Genet. May 2006;38(5):525-7. Epub Apr. 23, 2006. PMID: 16642017; A recurrent mutation in the BMP type I receptor ACVR1 causes inherited and sporadic fibrodysplasia ossificans progressiva.
Sorkin et al., "Regulation of heterotopic ossification by monocytes in a mouse model of aberrant wound healing," Nature Communications (2020) 11:722 | https://doi.org/10.1038/s41467-019-14172-4.
Taylor et al., "Recurrent activating ACVR1 mutations in diffuse intrinsic pontine glioma," Nat Genet. May 2014; 46(5): 457-461. doi:10.1038/ng.2925.
Tutt et al., "Trispecific F(ab')3 derivatives that use cooperative signaling via the TCR/CD3 complex and CD2 to activiate and redirect resting cytotoxic T cells," Journal of Immunology, 147(1):60-69 (Jul. 1, 1991).
Upadhyay et al., "The Expansion of Heterotopic Bone in Fibrodysplasia Ossificans Progressiva is Activin A-Dependent," Journal of Bone and Mineral Research, vol. 32, No. 12, Dec. 2017, pp. 2489-2499; DOI: 10.1002/jbmr.3235.
Vajdos et al., "Comprehensive Functional Maps of the Antigen-binding Site of an Anti-ErbB2 Antibody Obtained with Shotgun Scanning Mutagenesis," J. Mol. Biol., 320{2}:415-428 (Jul. 2002).
Van Dinther et al., "ALK2 R206H Mutation Linked to Fibrodysplasia Ossificans Progressiva Confers Constitutive Activity to the BMP Type I Receptor and Sensitizes Mesenchymal Cells to BMP-Induced Osteoblast Differentiation and Bone Formation," Journal of Bone and Mineral Research, vol. 25, No. 6, pp. 1208-1215 (Jun. 2010).
Wu et al., "Receptor-mediated in Vitro Gene Transformation by a Soluble DNA Carrier System," The Journal of Biological Chemistry, vol. 262, No. 10, pp. 4429-4432 (Apr. 5, 1987).
Dondelinger et al., "Understanding the Significance and Implications of Antibody Numbering and Antigen-Binding Surface/Residue Definition," Frontiers in Immunology, vol. 9, Article 2278, doi.org/10.3389/fimmu.2018.02278, pp. 1-15 (Oct. 2018).
European Office Action for Application No. 21710676.4 dated Feb. 8, 2024.
Vaughan et al. "Human Antibodies with Sub-nanomolar Affinities Isolated from a Large Non-immunized Phage Display Library," Nature Biotechnology, vol. 14, pp. 309-314 (Mar. 1996).

\* cited by examiner

SEQUENCE LISTING

```
<160> NUMBER OF SEQ ID NOS: 342

<210> SEQ ID NO 1
<211> LENGTH: 366
<212> TYPE: DNA
<213> ORGANISM: Artificial Sequence
<220> FEATURE:
<223> OTHER INFORMATION: synthetic

<400> SEQUENCE: 1
caggtgcatc tggtggagtc tggggggaggc gtggtccagc ctgggaggtc cctgagactc      60
tcctgtgcag cctctggatt caccttcagt aactatggca tacactgggt ccgccaggtt     120
ccaggcaagg ggctggagtg ggtggcagtt atatcatatg atggaaataa taatactat      180 ggggactccg tgaagggccg attcaccatc tctagagaca attccaagaa cacactgtat     240
ctgcaaatga acagcctgag acctgaggac acggctatct attactgtgc gaaagatcgt     300
ggcctggaca cagctggtga ctactttgac tattggggcc agggaaccct ggtcaccgtc     360
tcctca                                                                 366

<210> SEQ ID NO 2
<211> LENGTH: 122
<212> TYPE: PRT
<213> ORGANISM: Artificial Sequence
<220> FEATURE:
<223> OTHER INFORMATION: synthetic

<400> SEQUENCE: 2

Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Val Pro Gly Lys Gly Leu Glu Trp Val
        35                  40                  45

Ala Val Ile Ser Tyr Asp Gly Asn Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ile Tyr Tyr Cys
                85                  90                  95

Ala Lys Asp Arg Gly Leu Asp Thr Ala Gly Asp Tyr Phe Asp Tyr Trp
            100                 105                 110

Gly Gln Gly Thr Leu Val Thr Val Ser Ser
        115                 120

<210> SEQ ID NO 3
<211> LENGTH: 24
```

```
<212> TYPE: DNA
<213> ORGANISM: Artificial Sequence
<220> FEATURE:
<223> OTHER INFORMATION: synthetic

<400> SEQUENCE: 3
ggattcacct tcagtaacta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Asn Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atatcatatg atggaaataa taaa                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Tyr Asp Gly Asn Asn Lys
1               5

<210> SEQ ID NO 7
<211> LENGTH: 45
<212> TYPE: DNA
<213> ORGANISM: Artificial Sequence
<220> FEATURE:
<223> OTHER INFORMATION: synthetic

<400> SEQUENCE: 7
gcgaaagatc gtggcctgga cacagctggt gactactttg actat                   45

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Ala Lys Asp Arg Gly Leu Asp Thr Ala Gly Asp Tyr Phe Asp Tyr
1               5                   10                  15

<210> SEQ ID NO 9
<211> LENGTH: 318
<212> TYPE: DNA
<213> ORGANISM: Artificial Sequence
<220> FEATURE:
<223> OTHER INFORMATION: synthetic
```

-continued

<400> SEQUENCE: 9

```
gaaatagtga tgacgcagtc tccagccacc ctgtctgtgt ctacagggga aagagccacc    60
ctctcctgca gggccagtca gaatattagt agcaaattgg cctggtacca gcagaaacct   120
ggccaggctc ccaggctcct catttatggt gcatccacca gggcctctgg tatcccagcc   180
agattctggg gcagtgggtc tgggacagag ttcactctca ccatcagcag tctgcagtct   240
gaagattttg cagttttttta ctgtctccag tataataact ggtggacgtt cggccaaggg   300
accaaggtgg aaatcaaa                                                 318
```

<210> SEQ ID NO 10
<211> LENGTH: 106
<212> TYPE: PRT
<213> ORGANISM: Artificial Sequence
<220> FEATURE:
<223> OTHER INFORMATION: synthetic

<400> SEQUENCE: 10

```
Glu Ile Val Met Thr Gln Ser Pro Ala Thr Leu Ser Val Ser Thr Gly
1               5                  10                  15

Glu Arg Ala Thr Leu Ser Cys Arg Ala Ser Gln Asn Ile Ser Ser Lys
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Trp Gly
    50                  55                  60

Ser Gly Ser Gly Thr Glu Phe Thr Leu Thr Ile Ser Ser Leu Gln Ser
65                  70                  75                  80

Glu Asp Phe Ala Val Phe Tyr Cys Leu Gln Tyr Asn Asn Trp Trp Thr
                85                  90                  95

Phe Gly Gln Gly Thr Lys Val Glu Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11

```
cagaatatta gtagcaaa                                                  18
```

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

```
Gln Asn Ile Ser Ser Lys
1               5
```

<210> SEQ ID NO 13
<211> LENGTH: 9
<212> TYPE: DNA
<213> ORGANISM: Artificial Sequence
<220> FEATURE:
<223> OTHER INFORMATION: synthetic -continued

<400> SEQUENCE: 13 ggtgcatcc                                                                      9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Gly Ala Ser
1

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
ctccagtata ataactggtg gacg                                                    24

<210> SEQ ID NO 16
<211> LENGTH: 8
<212> TYPE: PRT
<213> ORGANISM: Artificial Sequence
<220> FEATURE:
<223> OTHER INFORMATION: synthetic

<400> SEQUENCE: 16

Leu Gln Tyr Asn Asn Trp Trp Thr
1               5

<210> SEQ ID NO 17
<211> LENGTH: 1350
<212> TYPE: DNA
<213> ORGANISM: Artificial Sequence
<220> FEATURE:
<223> OTHER INFORMATION: synthetic

<400> SEQUENCE: 17
caggtgcatc tggtggagtc tgggggaggc gtggtccagc ctgggaggtc cctgagactc      60
tcctgtgcag cctctggatt caccttcagt aactatggca tacactgggt ccgccaggtt     120
ccaggcaagg ggctggagtg ggtggcagtt atatcatatg atggaaataa taaatactat     180
ggggactccg tgaagggccg attcaccatc tctagagaca attccaagaa cacactgtat     240
ctgcaaatga acagcctgag acctgaggac acggctatct attactgtgc gaaagatcgt     300
ggcctggaca cagctggtga ctactttgac tattggggcc agggaaccct ggtcaccgtc     360
tcctcagcct ccaccaaggg cccatcggtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccaccc tgcccagcac ctgagttcct ggggggacca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840

```
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020 gccaagggc agccccgaga gccacaggtg tacaccctgc ccccatccca ggaggagatg    1080
accaagaacc aggtcagcct gacctgcctg gtcaaaggct tctaccccag cgacatcgcc   1140
gtggagtggg agagcaatgg gcagccggag aacaactaca agaccacgcc tcccgtgctg   1200
gactccgacg gctccttctt cctctacagc aggctcaccg tggacaagag caggtggcag   1260
gaggggaatg tcttctcatg ctccgtgatg catgaggctc tgcacaacca ctacacacag   1320
aagtccctct ccctgtctct gggtaaatga                                    1350
```

<210> SEQ ID NO 18
<211> LENGTH: 449
<212> TYPE: PRT
<213> ORGANISM: Artificial Sequence
<220> FEATURE:
<223> OTHER INFORMATION: synthetic

<400> SEQUENCE: 18

```
Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Val Pro Gly Lys Gly Leu Glu Trp Val
        35                  40                  45

Ala Val Ile Ser Tyr Asp Gly Asn Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ile Tyr Tyr Cys
                85                  90                  95

Ala Lys Asp Arg Gly Leu Asp Thr Ala Gly Asp Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270
```

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 19
<211> LENGTH: 642
<212> TYPE: DNA
<213> ORGANISM: Artificial Sequence
<220> FEATURE:
<223> OTHER INFORMATION: synthetic

<400> SEQUENCE: 19
gaaatagtga tgacgcagtc tccagccacc ctgtctgtgt ctacagggga agagccacc      60 ctctcctgca gggccagtca gaatattagt agcaaattgg cctggtacca gcagaaacct    120
ggccaggctc ccaggctcct catttatggt gcatccacca gggcctctgg tatcccagcc    180
agattctggg gcagtgggtc tgggacagag ttcactctca ccatcagcag tctgcagtct    240
gaagattttg cagttttta ctgtctccag tataataact ggtggacgtt cggccaaggg     300
accaaggtgg aaatcaaacg aactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag     480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ag                        642

<210> SEQ ID NO 20
<211> LENGTH: 213
<212> TYPE: PRT
<213> ORGANISM: Artificial Sequence
<220> FEATURE:
<223> OTHER INFORMATION: synthetic

<400> SEQUENCE: 20

Glu Ile Val Met Thr Gln Ser Pro Ala Thr Leu Ser Val Ser Thr Gly
1               5                   10                  15

Glu Arg Ala Thr Leu Ser Cys Arg Ala Ser Gln Asn Ile Ser Ser Lys
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Trp Gly
    50                  55                  60

Ser Gly Ser Gly Thr Glu Phe Thr Leu Thr Ile Ser Ser Leu Gln Ser
65                  70                  75                  80

Glu Asp Phe Ala Val Phe Tyr Cys Leu Gln Tyr Asn Asn Trp Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 21
<211> LENGTH: 345
<212> TYPE: DNA
<213> ORGANISM: Artificial Sequence
<220> FEATURE:
<223> OTHER INFORMATION: synthetic

<400> SEQUENCE: 21
caggtgcagc tacagcagtg gggcgcagga ctgttgaagc cttcggagac cctgtccctc    60
acctgcgctg tctataatgg gtccttcagt agttactact ggaactggat ccgccagccc   120
ccggggaagg ggctggagtg gcttggagaa atcaatcata gaggaagcac caactacaac   180
ccgtccctca cgagtcgagt caccatatca gttgacacgt ccaagaacca gttctccctg   240
aagctgacct ctgtgaccgc cgcggacacg gcaatatatt attgtacggc gcatactcgg   300
ggctttctat actggggcca gggaaccctg gtcaccgtct cctca                   345

<210> SEQ ID NO 22
<211> LENGTH: 115
<212> TYPE: PRT
<213> ORGANISM: Artificial Sequence
<220> FEATURE:
<223> OTHER INFORMATION: synthetic

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Asn Gly Ser Phe Ser Ser Tyr
            20                  25                  30

Tyr Trp Asn Trp Ile Arg Gln Pro Pro Gly Lys Gly Leu Glu Trp Leu
             35                  40                  45

Gly Glu Ile Asn His Arg Gly Ser Thr Asn Tyr Asn Pro Ser Leu Thr
 50                  55                  60

Ser Arg Val Thr Ile Ser Val Asp Thr Ser Lys Asn Gln Phe Ser Leu
 65                  70                  75                  80

Lys Leu Thr Ser Val Thr Ala Ala Asp Thr Ala Ile Tyr Tyr Cys Thr
                 85                  90                  95

Ala His Thr Arg Gly Phe Leu Tyr Trp Gly Gln Gly Thr Leu Val Thr
            100                 105                 110

Val Ser Ser
        115

<210> SEQ ID NO 23
<211> LENGTH: 24
<212> TYPE: DNA
<213> ORGANISM: Artificial Sequence
<220> FEATURE:
<223> OTHER INFORMATION: synthetic

<400> SEQUENCE: 23
aatgggtcct tcagtagtta ctac                                      24

<210> SEQ ID NO 24
<211> LENGTH: 8
<212> TYPE: PRT
<213> ORGANISM: Artificial Sequence
<220> FEATURE:
<223> OTHER INFORMATION: synthetic

<400> SEQUENCE: 24

Asn Gly Ser Phe Ser Ser Tyr Tyr
 1               5

<210> SEQ ID NO 25
<211> LENGTH: 21
<212> TYPE: DNA
<213> ORGANISM: Artificial Sequence
<220> FEATURE:
<223> OTHER INFORMATION: synthetic

<400> SEQUENCE: 25
atcaatcata gaggaagcac c                                         21

<210> SEQ ID NO 26
<211> LENGTH: 7
<212> TYPE: PRT
<213> ORGANISM: Artificial Sequence
<220> FEATURE:
<223> OTHER INFORMATION: synthetic

<400> SEQUENCE: 26

Ile Asn His Arg Gly Ser Thr
 1               5

<210> SEQ ID NO 27
<211> LENGTH: 27
<212> TYPE: DNA
<213> ORGANISM: Artificial Sequence
<220> FEATURE:
<223> OTHER INFORMATION: synthetic

<400> SEQUENCE: 27
acggcgcata ctcggggctt tctatac                                   27

```
<210> SEQ ID NO 28
<211> LENGTH: 9
<212> TYPE: PRT
<213> ORGANISM: Artificial Sequence
<220> FEATURE:
<223> OTHER INFORMATION: synthetic

<400> SEQUENCE: 28

Thr Ala His Thr Arg Gly Phe Leu Tyr
1               5

<210> SEQ ID NO 29
<211> LENGTH: 321
<212> TYPE: DNA
<213> ORGANISM: Artificial Sequence
<220> FEATURE:
<223> OTHER INFORMATION: synthetic

<400> SEQUENCE: 29
gacatccaga tgacccagtc tccatcctcc ctgtctgcat ctgtaggaga cagagtcacc    60
atcacttgcc aggcgagtca ggacattaac atctatttaa attggtatca gcagcaacca   120
gggaaagccc ctaaactcct gatctacgat gtatccaatt tggtaccggg ggtcccatca   180
aggttcagtg gtactggatc tgggacacat ttttccttca ccatcagcag cctgcaacct   240
gaagatattg caacatatta ctgtcaaCac tatgatgatc tcccgctcac tttcggcgga   300
gggaccacgg tggcgatcag a                                             321

<210> SEQ ID NO 30
<211> LENGTH: 107
<212> TYPE: PRT
<213> ORGANISM: Artificial Sequence
<220> FEATURE:
<223> OTHER INFORMATION: synthetic

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Ile Tyr
            20                  25                  30

Leu Asn Trp Tyr Gln Gln Gln Pro Gly Lys Ala Pro Lys Leu Leu Ile
        35                  40                  45

Tyr Asp Val Ser Asn Leu Val Pro Gly Val Pro Ser Arg Phe Ser Gly
    50                  55                  60

Thr Gly Ser Gly Thr His Phe Ser Phe Thr Ile Ser Ser Leu Gln Pro
65                  70                  75                  80

Glu Asp Ile Ala Thr Tyr Tyr Cys Gln His Tyr Asp Asp Leu Pro Leu
                85                  90                  95

Thr Phe Gly Gly Gly Thr Thr Val Ala Ile Arg
            100                 105

<210> SEQ ID NO 31
<211> LENGTH: 18
<212> TYPE: DNA
<213> ORGANISM: Artificial Sequence
<220> FEATURE:
<223> OTHER INFORMATION: synthetic

<400> SEQUENCE: 31
caggacatta acatctat                                                  18
```

```
<210> SEQ ID NO 32
<211> LENGTH: 6
<212> TYPE: PRT
<213> ORGANISM: Artificial Sequence
<220> FEATURE:
<223> OTHER INFORMATION: synthetic

<400> SEQUENCE: 32

Gln Asp Ile Asn Ile Tyr
1               5

<210> SEQ ID NO 33
<211> LENGTH: 9
<212> TYPE: DNA
<213> ORGANISM: Artificial Sequence
<220> FEATURE:
<223> OTHER INFORMATION: synthetic

<400> SEQUENCE: 33 gatgtatcc                                                                 9

<210> SEQ ID NO 34
<211> LENGTH: 3
<212> TYPE: PRT
<213> ORGANISM: Artificial Sequence
<220> FEATURE:
<223> OTHER INFORMATION: synthetic

<400> SEQUENCE: 34

Asp Val Ser
1

<210> SEQ ID NO 35
<211> LENGTH: 27
<212> TYPE: DNA
<213> ORGANISM: Artificial Sequence
<220> FEATURE:
<223> OTHER INFORMATION: synthetic

<400> SEQUENCE: 35
caacactatg atgatctccc gctcact                                            27

<210> SEQ ID NO 36
<211> LENGTH: 9
<212> TYPE: PRT
<213> ORGANISM: Artificial Sequence
<220> FEATURE:
<223> OTHER INFORMATION: synthetic

<400> SEQUENCE: 36

Gln His Tyr Asp Asp Leu Pro Leu Thr
1               5

<210> SEQ ID NO 37
<211> LENGTH: 1329
<212> TYPE: DNA
<213> ORGANISM: Artificial Sequence
<220> FEATURE:
<223> OTHER INFORMATION: synthetic

<400> SEQUENCE: 37
caggtgcagc tacagcagtg gggcgcagga ctgttgaagc cttcggagac cctgtccctc         60
acctgcgctg tctataatgg gtccttcagt agttactact ggaactggat ccgccagccc        120
ccggggaagg ggctggagtg gcttggagaa atcaatcata gaggaagcac caactacaac        180
```

```
ccgtccctca cgagtcgagt caccatatca gttgacacgt ccaagaacca gttctccctg    240
aagctgacct ctgtgaccgc cgcggacacg gcaatatatt attgtacggc catactcgg    300 ggctttctat actggggcca gggaaccctg gtcaccgtct cctcagcctc caccaagggc    360
ccatcggtct tccccctggc gccctgctcc aggagcacct ccgagagcac agccgccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcacga gacctacac ctgcaacgta    600 gatcacaagc ccagcaacac caaggtggac aagagagttg agtccaaata tggtccccca    660
tgcccaccct gcccagcacc tgagttcctg ggggaccat cagtcttcct gttccccca    720 aaacccaagg acactctcat gatctcccgg acccctgagg tcacgtgcgt ggtggtggac    780
gtgagccagg aagaccccga ggtccagttc aactggtacg tggatggcgt ggaggtgcat    840
aatgccaaga caaagccgcg ggaggagcag ttcaacagca cgtaccgtgt ggtcagcgtc    900
ctcaccgtcc tgcaccagga ctggctgaac ggcaaggagt acaagtgcaa ggtctccaac    960
aaaggcctcc cgtcctccat cgagaaaacc atctccaaag ccaaagggca gccccgagag   1020
ccacaggtgt acaccctgcc cccatcccag gaggagatga ccaagaacca ggtcagcctg   1080
acctgcctgg tcaaaggctt ctaccccagc gacatcgccg tggagtggga gagcaatggg   1140
cagccggaga caactacaa gaccacgcct cccgtgctgg actccgacgg ctccttcttc    1200
ctctacagca ggctcaccgt ggacaagagc aggtggcagg aggggaatgt cttctcatgc   1260
tccgtgatgc atgaggctct gcacaaccac tacacacaga gtccctctc cctgtctctg    1320 ggtaaatga                                                            1329
```

<210> SEQ ID NO 38
<211> LENGTH: 442
<212> TYPE: PRT
<213> ORGANISM: Artificial Sequence
<220> FEATURE:
<223> OTHER INFORMATION: synthetic

<400> SEQUENCE: 38

```
Gln Val Gln Leu Gln Gln Trp Gly Ala Gly Leu Leu Lys Pro Ser Glu
1               5                   10                  15

Thr Leu Ser Leu Thr Cys Ala Val Tyr Asn Gly Ser Phe Ser Ser Tyr
            20                  25                  30

Tyr Trp Asn Trp Ile Arg Gln Pro Pro Gly Lys Gly Leu Glu Trp Leu
        35                  40                  45

Gly Glu Ile Asn His Arg Gly Ser Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Ile Tyr Tyr Cys Thr
                85                  90                  95

Ala His Thr Arg Gly Phe Leu Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Lys Thr Tyr Thr Cys Asn Val Asp His Lys Pro Ser Asn Thr Lys
    195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 39
<211> LENGTH: 645
<212> TYPE: DNA
<213> ORGANISM: Artificial Sequence
<220> FEATURE:
<223> OTHER INFORMATION: synthetic

<400> SEQUENCE: 39
gacatccaga tgacccagtc tccatcctcc ctgtctgcat ctgtaggaga cagagtcacc      60
atcacttgcc aggcgagtca ggacattaac atctatttaa attggtatca gcagcaacca     120
gggaaagccc ctaaactcct gatctacgat gtatccaatt tggtaccggg gtcccatca      180 aggttcagtg gtactggatc tgggacacat ttttccttca ccatcagcag cctgcaacct     240
gaagatattg caacatatta ctgtcaaaca tatgatgatc cccgctcac tttcggcgga      300 gggaccacgg tggcgatcag acgaactgtg gctgcaccat ctgtcttcat cttcccgcca     360
tctgatgagc agttgaaatc tggaactgcc tctgttgtgt gcctgctgaa taacttctat     420

```
cccagagagg ccaaagtaca gtggaaggtg ataacgccc tccaatcggg taactcccag    480
gagagtgtca cagagcagga cagcaaggac agcacctaca gcctcagcag cacccctgacg  540 ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 40
<211> LENGTH: 214
<212> TYPE: PRT
<213> ORGANISM: Artificial Sequence
<220> FEATURE:
<223> OTHER INFORMATION: synthetic

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Ile Tyr
            20                  25                  30

Leu Asn Trp Tyr Gln Gln Pro Gly Lys Ala Pro Lys Leu Leu Ile
        35                  40                  45

Tyr Asp Val Ser Asn Leu Val Pro Gly Val Pro Ser Arg Phe Ser Gly
50                  55                  60

Thr Gly Ser Gly Thr His Phe Ser Phe Thr Ile Ser Ser Leu Gln Pro
65                  70                  75                  80

Glu Asp Ile Ala Thr Tyr Tyr Cys Gln His Tyr Asp Asp Leu Pro Leu
                85                  90                  95

Thr Phe Gly Gly Gly Thr Thr Val Ala Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 41
<211> LENGTH: 345
<212> TYPE: DNA
<213> ORGANISM: Artificial Sequence
<220> FEATURE:
<223> OTHER INFORMATION: synthetic

<400> SEQUENCE: 41

```
caggtgcagc tacagcagtg gggcgcagga ctgttgaagc cttcggagac cctgtccctc    60
acctgcgctg tctataatgg gtccttcagt agtttctact ggagctggat ccgccagccc   120
ccggggaagg ggctggagtg gcttgggaa atcaatcata aggaagaac caacaacaac    180 ccgtccctcg cgagtcgagt caccatatca gttgacacgt ccaagagcca gttctccctg   240
```

-continued

```
aggctgacct ctgtgaccgc cgcggacacg gctacatatt attgtacggc gcatactcgg       300
ggctttctat actggggcca gggaacccgg gtcaccgtct cctca                     345
```

<210> SEQ ID NO 42
<211> LENGTH: 115
<212> TYPE: PRT
<213> ORGANISM: Artificial Sequence
<220> FEATURE:
<223> OTHER INFORMATION: synthetic
<400> SEQUENCE: 42

```
Gln Val Gln Leu Gln Gln Trp Gly Ala Gly Leu Leu Lys Pro Ser Glu
1               5                   10                  15

Thr Leu Ser Leu Thr Cys Ala Val Tyr Asn Gly Ser Phe Ser Ser Phe
            20                  25                  30

Tyr Trp Ser Trp Ile Arg Gln Pro Pro Gly Lys Gly Leu Glu Trp Leu
        35                  40                  45

Gly Glu Ile Asn His Arg Gly Arg Thr Asn Asn Pro Ser Leu Ala
    50                  55                  60

Ser Arg Val Thr Ile Ser Val Asp Thr Ser Lys Ser Gln Phe Ser Leu
65                  70                  75                  80

Arg Leu Thr Ser Val Thr Ala Ala Asp Thr Ala Thr Tyr Tyr Cys Thr
                85                  90                  95

Ala His Thr Arg Gly Phe Leu Tyr Trp Gly Gln Gly Thr Arg Val Thr
            100                 105                 110

Val Ser Ser
       115
```

<210> SEQ ID NO 43
<211> LENGTH: 24
<212> TYPE: DNA
<213> ORGANISM: Artificial Sequence
<220> FEATURE:
<223> OTHER INFORMATION: synthetic
<400> SEQUENCE: 43

```
aatgggtcct tcagtagttt ctac                                             24
```

<210> SEQ ID NO 44
<211> LENGTH: 8
<212> TYPE: PRT
<213> ORGANISM: Artificial Sequence
<220> FEATURE:
<223> OTHER INFORMATION: synthetic
<400> SEQUENCE: 44

```
Asn Gly Ser Phe Ser Ser Phe Tyr
1               5
```

<210> SEQ ID NO 45
<211> LENGTH: 21
<212> TYPE: DNA
<213> ORGANISM: Artificial Sequence
<220> FEATURE:
<223> OTHER INFORMATION: synthetic
<400> SEQUENCE: 45

```
atcaatcata gaggaagaac c                                                21
```

<210> SEQ ID NO 46
<211> LENGTH: 7
<212> TYPE: PRT

<213> ORGANISM: Artificial Sequence
<220> FEATURE:
<223> OTHER INFORMATION: synthetic

<400> SEQUENCE: 46

Ile Asn His Arg Gly Arg Thr
1               5

<210> SEQ ID NO 47
<211> LENGTH: 321
<212> TYPE: DNA
<213> ORGANISM: Artificial Sequence
<220> FEATURE:
<223> OTHER INFORMATION: synthetic

<400> SEQUENCE: 47

```
gacatccaga tgacccagtc tccatcctcc ctgtctgcat ctgtaggaga cagagtcacc      60
atcacttgcc aggcgagtca ggacattaac aactatttaa attggtatca gcagaaacca     120
gggcaagccc ctaacctcct gatctacgat gtatttaatt tactaccggg ggtcccatca     180
aggttcagtg aagtggatc tgggacagat ttttccttca ccatcagcag cctgcagcct     240
gaagatattg caacatatta ctgtcaaca tatgatgatc tcccgctcac tttcggcggc     300
gggaccacgg tggcgatcag a                                              321
```

<210> SEQ ID NO 48
<211> LENGTH: 107
<212> TYPE: PRT
<213> ORGANISM: Artificial Sequence
<220> FEATURE:
<223> OTHER INFORMATION: synthetic

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Gln Ala Pro Asn Leu Leu Ile
        35                  40                  45

Tyr Asp Val Phe Asn Leu Leu Pro Gly Val Pro Ser Arg Phe Ser Gly
    50                  55                  60

Ser Gly Ser Gly Thr Asp Phe Ser Phe Thr Ile Ser Ser Leu Gln Pro
65                  70                  75                  80

Glu Asp Ile Ala Thr Tyr Tyr Cys Gln His Tyr Asp Asp Leu Pro Leu
                85                  90                  95

Thr Phe Gly Gly Gly Thr Thr Val Ala Ile Arg
            100                 105

<210> SEQ ID NO 49
<211> LENGTH: 18
<212> TYPE: DNA
<213> ORGANISM: Artificial Sequence
<220> FEATURE:
<223> OTHER INFORMATION: synthetic

<400> SEQUENCE: 49
caggacatta acaactat                                                   18

<210> SEQ ID NO 50
<211> LENGTH: 6
<212> TYPE: PRT
<213> ORGANISM: Artificial Sequence

```
<220> FEATURE:
<223> OTHER INFORMATION: synthetic

<400> SEQUENCE: 50

Gln Asp Ile Asn Asn Tyr
1               5

<210> SEQ ID NO 51
<211> LENGTH: 9
<212> TYPE: DNA
<213> ORGANISM: Artificial Sequence
<220> FEATURE:
<223> OTHER INFORMATION: synthetic

<400> SEQUENCE: 51 gatgtattt                                                                  9

<210> SEQ ID NO 52
<211> LENGTH: 3
<212> TYPE: PRT
<213> ORGANISM: Artificial Sequence
<220> FEATURE:
<223> OTHER INFORMATION: synthetic

<400> SEQUENCE: 52

Asp Val Phe
1

<210> SEQ ID NO 53
<211> LENGTH: 1329
<212> TYPE: DNA
<213> ORGANISM: Artificial Sequence
<220> FEATURE:
<223> OTHER INFORMATION: synthetic

<400> SEQUENCE: 53
caggtgcagc tacagcagtg gggcgcagga ctgttgaagc cttcggagac cctgtccctc        60
acctgcgctg tctataatgg gtccttcagt agtttctact ggagctggat ccgccagccc       120
ccggggaagg ggctggagtg gcttggggaa atcaatcata gaggaagaac caacaacaac       180
ccgtccctcg cgagtcgagt caccatatca gttgacacgt ccaagagcca gttctccctg       240
aggctgacct ctgtgaccgc cgcggacacg gctacatatt attgtacggc gcatactcgg       300
ggctttctat actggggcca gggaacccgg gtcaccgtct cctcagcctc caccaagggc       360
ccatcggtct tccccctggc gccctgctcc aggagcacct ccgagagcac agccgccctg       420
ggctgcctgg tcaaggacta cttccccgaa ccggtgacgg tgtcgtggaa ctcaggcgcc       480
ctgaccagcg gcgtgcacac cttcccggct gtcctacagt cctcaggact ctactccctc       540
agcagcgtgg tgaccgtgcc ctccagcagc ttgggcacga agacctacac ctgcaacgta       600
gatcacaagc ccagcaacac caaggtggac aagagagttg agtccaaata tggtccccca       660
tgcccaccct gcccagcacc tgagttcctg ggggaccat cagtcttcct gttccccca         720 aaacccaagg acactctcat gatctcccgg acccctgagg tcacgtgcgt ggtggtggac       780
gtgagccagg aagaccccga ggtccagttc aactggtacg tggatggcgt ggaggtgcat       840
aatgccaaga caaagccgcg ggaggagcag ttcaacagca cgtaccgtgt ggtcagcgtc       900
ctcaccgtcc tgcaccagga ctggctgaac ggcaaggagt acaagtgcaa ggtctccaac       960
aaaggcctcc cgtcctccat cgagaaaacc atctccaaag ccaaaggcag ccccgagag      1020 ccacaggtgt acaccctgcc cccatcccag gaggagatga ccaagaacca ggtcagcctg      1080
```

```
acctgcctgg tcaaaggctt ctaccccagc gacatcgccg tggagtggga gagcaatggg    1140
cagccggaga caactacaa gaccacgcct cccgtgctgg actccgacgg ctccttcttc    1200
ctctacagca ggctcaccgt ggacaagagc aggtggcagg agggggaatgt cttctcatgc    1260 tccgtgatgc atgaggctct gcacaaccac tacacacaga agtccctctc cctgtctctg    1320
ggtaaatga                                                             1329
```

<210> SEQ ID NO 54
<211> LENGTH: 442
<212> TYPE: PRT
<213> ORGANISM: Artificial Sequence
<220> FEATURE:
<223> OTHER INFORMATION: synthetic

<400> SEQUENCE: 54

```
Gln Val Gln Leu Gln Gln Trp Gly Ala Gly Leu Leu Lys Pro Ser Glu
1               5                   10                  15

Thr Leu Ser Leu Thr Cys Ala Val Tyr Asn Gly Ser Phe Ser Ser Phe
            20                  25                  30

Tyr Trp Ser Trp Ile Arg Gln Pro Pro Gly Lys Gly Leu Glu Trp Leu
        35                  40                  45

Gly Glu Ile Asn His Arg Gly Arg Thr Asn Asn Pro Ser Leu Ala
    50                  55                  60

Ser Arg Val Thr Ile Ser Val Asp Thr Ser Lys Ser Gln Phe Ser Leu
65                  70                  75                  80

Arg Leu Thr Ser Val Thr Ala Ala Asp Thr Ala Thr Tyr Tyr Cys Thr
                85                  90                  95

Ala His Thr Arg Gly Phe Leu Tyr Trp Gly Gln Gly Thr Arg Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320
```

Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
        340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
            435                 440

<210> SEQ ID NO 55
<211> LENGTH: 645
<212> TYPE: DNA
<213> ORGANISM: Artificial Sequence
<220> FEATURE:
<223> OTHER INFORMATION: synthetic

<400> SEQUENCE: 55
gacatccaga tgacccagtc tccatcctcc ctgtctgcat ctgtaggaga cagagtcacc      60
atcacttgcc aggcgagtca ggacattaac aactatttaa attggtatca gcagaaacca     120
gggcaagccc ctaacctcct gatctacgat gtatttaatt tactaccggg ggtcccatca     180
aggttcagtg aagtggatc tgggacagat ttttccttca ccatcagcag cctgcagcct     240
gaagatattg caacatatta ctgtcaaaca tatgatgatc tcccgctcac tttcggcggc     300
gggaccacgg tggcgatcag acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                      645

<210> SEQ ID NO 56
<211> LENGTH: 214
<212> TYPE: PRT
<213> ORGANISM: Artificial Sequence
<220> FEATURE:
<223> OTHER INFORMATION: synthetic

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Gln Ala Pro Asn Leu Leu Ile
        35                  40                  45

Tyr Asp Val Phe Asn Leu Leu Pro Gly Val Pro Ser Arg Phe Ser Gly
    50                  55                  60

Ser Gly Ser Gly Thr Asp Phe Ser Phe Thr Ile Ser Ser Leu Gln Pro
 65                  70                  75                  80

Glu Asp Ile Ala Thr Tyr Tyr Cys Gln His Tyr Asp Asp Leu Pro Leu
                 85                  90                  95

Thr Phe Gly Gly Gly Thr Thr Val Ala Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 57
<211> LENGTH: 345
<212> TYPE: DNA
<213> ORGANISM: Artificial Sequence
<220> FEATURE:
<223> OTHER INFORMATION: synthetic

<400> SEQUENCE: 57
caggtgcagc tacagcagtg gggcgcagga ctgttgaagc cttcggagac cctgtccctc      60
acctgcgctg tctataatgg gtccttcagt agttactact ggagctggat ccgccagccc     120
ccggggaagg gactggagtg gcttggggaa atcaatcata aggaagaac caactacaac      180 ccgtccctca cgagtcgagt caccatttca gttgacacgt ccaagaacca gttctccctg     240
aagctgccct ctgtgaccgc cgcagacacg gccatatatt attgttcggc acatactcgg     300
ggctttctat attggggcca gggaaccctg gtcaccgtct cctca                     345

<210> SEQ ID NO 58
<211> LENGTH: 115
<212> TYPE: PRT
<213> ORGANISM: Artificial Sequence
<220> FEATURE:
<223> OTHER INFORMATION: synthetic

<400> SEQUENCE: 58

Gln Val Gln Leu Gln Gln Trp Gly Ala Gly Leu Leu Lys Pro Ser Glu
 1               5                  10                  15

Thr Leu Ser Leu Thr Cys Ala Val Tyr Asn Gly Ser Phe Ser Ser Tyr
                20                  25                  30

Tyr Trp Ser Trp Ile Arg Gln Pro Pro Gly Lys Gly Leu Glu Trp Leu
            35                  40                  45

Gly Glu Ile Asn His Arg Gly Arg Thr Asn Tyr Asn Pro Ser Leu Thr
        50                  55                  60

Ser Arg Val Thr Ile Ser Val Asp Thr Ser Lys Asn Gln Phe Ser Leu
 65                  70                  75                  80

Lys Leu Pro Ser Val Thr Ala Ala Asp Thr Ala Ile Tyr Tyr Cys Ser
                 85                  90                  95

Ala His Thr Arg Gly Phe Leu Tyr Trp Gly Gln Gly Thr Leu Val Thr
            100                 105                 110

Val Ser Ser
        115

<210> SEQ ID NO 59
<211> LENGTH: 27
<212> TYPE: DNA
<213> ORGANISM: Artificial Sequence
<220> FEATURE:
<223> OTHER INFORMATION: synthetic

<400> SEQUENCE: 59
tcggcacata ctcggggctt tctatat                                          27

<210> SEQ ID NO 60
<211> LENGTH: 9
<212> TYPE: PRT
<213> ORGANISM: Artificial Sequence
<220> FEATURE:
<223> OTHER INFORMATION: synthetic

<400> SEQUENCE: 60

Ser Ala His Thr Arg Gly Phe Leu Tyr
1               5

<210> SEQ ID NO 61
<211> LENGTH: 321
<212> TYPE: DNA
<213> ORGANISM: Artificial Sequence
<220> FEATURE:
<223> OTHER INFORMATION: synthetic

<400> SEQUENCE: 61
gacatccaga tgacccagtc tccatcctcc ctgtctgcat ctgttggaga cagagtcacc      60
atcacttgcc aggcgagtca ggacattaac aactatttaa attggtatca gcagaaacca     120
gggaaagccc ctaagctcct gatctacgat gcatccaatt tggtaccggg ggtcccatca     180
aggttcagtg gtactggatc tgggacagat ttttccttca ccatcagcag cctgcagcct     240
gaagatattg caacatatta ctgtcaacac tattatgatc tcccgctcac tttcggcgga     300
gggaccacgg tggcgatcag c                                                321

<210> SEQ ID NO 62
<211> LENGTH: 107
<212> TYPE: PRT
<213> ORGANISM: Artificial Sequence
<220> FEATURE:
<223> OTHER INFORMATION: synthetic

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Val Pro Gly Val Pro Ser Arg Phe Ser Gly
    50                  55                  60

Thr Gly Ser Gly Thr Asp Phe Ser Phe Thr Ile Ser Ser Leu Gln Pro
65                  70                  75                  80

Glu Asp Ile Ala Thr Tyr Tyr Cys Gln His Tyr Tyr Asp Leu Pro Leu
            85                  90                  95

Thr Phe Gly Gly Gly Thr Thr Val Ala Ile Ser
        100                 105

<210> SEQ ID NO 63
<211> LENGTH: 9
<212> TYPE: DNA
<213> ORGANISM: Artificial Sequence
<220> FEATURE:
<223> OTHER INFORMATION: synthetic

<400> SEQUENCE: 63 gatgcatcc                                                                9

<210> SEQ ID NO 64
<211> LENGTH: 3
<212> TYPE: PRT
<213> ORGANISM: Artificial Sequence
<220> FEATURE:
<223> OTHER INFORMATION: synthetic

<400> SEQUENCE: 64

Asp Ala Ser
1

<210> SEQ ID NO 65
<211> LENGTH: 27
<212> TYPE: DNA
<213> ORGANISM: Artificial Sequence
<220> FEATURE:
<223> OTHER INFORMATION: synthetic

<400> SEQUENCE: 65
caacactatt atgatctccc gctcact                                           27

<210> SEQ ID NO 66
<211> LENGTH: 9
<212> TYPE: PRT
<213> ORGANISM: Artificial Sequence
<220> FEATURE:
<223> OTHER INFORMATION: synthetic

<400> SEQUENCE: 66

Gln His Tyr Tyr Asp Leu Pro Leu Thr
1               5

<210> SEQ ID NO 67
<211> LENGTH: 1329
<212> TYPE: DNA
<213> ORGANISM: Artificial Sequence
<220> FEATURE:
<223> OTHER INFORMATION: synthetic

<400> SEQUENCE: 67
caggtgcagc tacagcagtg gggcgcagga ctgttgaagc cttcggagac cctgtccctc        60
acctgcgctg tctataatgg gtccttcagt agttactact ggagctggat ccgccagccc       120
ccggggaagg gactggagtg gcttggggaa atcaatcata gaggaagaac caactacaac       180
ccgtccctca cgagtcgagt caccatttca gttgacacgt ccaagaacca gttctccctg       240
aagctgccct ctgtgaccgc cgcagacacg gccatatatt attgttcggc acatactcgg       300
ggctttctat attggggcca gggaaccctg gtcaccgtct cctcagcctc caccaagggc       360
ccatcggtct tccccctggc gccctgctcc aggagcacct ccgagagcac agccgccctg       420

```
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcacga agacctacac ctgcaacgta    600
gatcacaagc ccagcaacac caaggtggac aagagagttg agtccaaata tggtccccca    660
tgcccaccct gcccagcacc tgagttcctg ggggaccat cagtcttcct gttccccca     720 aaacccaagg acactctcat gatctcccgg accctgagg tcacgtgcgt ggtggtggac    780
gtgagccagg aagaccccga ggtccagttc aactggtacg tggatggcgt ggaggtgcat    840
aatgccaaga caaagccgcg ggaggagcag ttcaacagca cgtaccgtgt ggtcagcgtc    900
ctcaccgtcc tgcaccagga ctggctgaac ggcaaggagt acaagtgcaa ggtctccaac    960
aaaggcctcc cgtcctccat cgagaaaacc atctccaaag ccaagggcag ccccgagag   1020 ccacaggtgt acaccctgcc cccatcccag gaggagatga ccaagaacca ggtcagcctg   1080
acctgcctgg tcaaaggctt ctaccccagc gacatcgccg tggagtggga gagcaatggg   1140
cagccggaga caactacaa gaccacgcct cccgtgctgg actccgacgg ctccttcttc    1200
ctctacagca ggctcaccgt ggacaagagc aggtggcagg aggggaatgt cttctcatgc   1260
tccgtgatgc atgaggctct gcacaaccac tacacacaga gtccctctc cctgtctctg    1320 ggtaaatga                                                            1329
```

<210> SEQ ID NO 68
<211> LENGTH: 442
<212> TYPE: PRT
<213> ORGANISM: Artificial Sequence
<220> FEATURE:
<223> OTHER INFORMATION: synthetic

<400> SEQUENCE: 68

```
Gln Val Gln Leu Gln Gln Trp Gly Ala Gly Leu Leu Lys Pro Ser Glu
1               5                   10                  15

Thr Leu Ser Leu Thr Cys Ala Val Tyr Asn Gly Ser Phe Ser Ser Tyr
            20                  25                  30

Tyr Trp Ser Trp Ile Arg Gln Pro Pro Gly Lys Gly Leu Glu Trp Leu
        35                  40                  45

Gly Glu Ile Asn His Arg Gly Arg Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

Lys Leu Pro Ser Val Thr Ala Ala Asp Thr Ala Ile Tyr Tyr Cys Ser
                85                  90                  95

Ala His Thr Arg Gly Phe Leu Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 69
<211> LENGTH: 645
<212> TYPE: DNA
<213> ORGANISM: Artificial Sequence
<220> FEATURE:
<223> OTHER INFORMATION: synthetic

<400> SEQUENCE: 69
gacatccaga tgacccagtc tccatcctcc ctgtctgcat ctgttggaga cagagtcacc      60
atcacttgcc aggcgagtca ggacattaac aactatttaa attggtatca gcagaaacca     120
gggaaagccc ctaagctcct gatctacgat gcatccaatt tggtaccggg ggtcccatca     180
aggttcagtg gtactggatc tgggacagat ttttccttca ccatcagcag cctgcagcct     240
gaagatattg caacatatta ctgtcaacac tattatgatc tcccgctcac tttcggcgga     300
gggaccacgg tggcgatcag ccgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

<210> SEQ ID NO 70
<211> LENGTH: 214
<212> TYPE: PRT
<213> ORGANISM: Artificial Sequence
<220> FEATURE:
<223> OTHER INFORMATION: synthetic

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Val Pro Gly Val Pro Ser Arg Phe Ser Gly
50                  55                  60

Thr Gly Ser Gly Thr Asp Phe Ser Phe Thr Ile Ser Ser Leu Gln Pro
65                  70                  75                  80

Glu Asp Ile Ala Thr Tyr Tyr Cys Gln His Tyr Tyr Asp Leu Pro Leu
                85                  90                  95

Thr Phe Gly Gly Gly Thr Thr Val Ala Ile Ser Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 71
<211> LENGTH: 321
<212> TYPE: DNA
<213> ORGANISM: Artificial Sequence
<220> FEATURE:
<223> OTHER INFORMATION: synthetic

<400> SEQUENCE: 71

```
gacatccaga tgacccagtc tccatcctcc ctgtctgcat ctgtaggaga cagagtcacc    60
atcacttgcc aggcgagtca ggacattaac aactatttaa attggtatca gcagaaacca   120
gggaaagccc ctaagctcct gatctacgat gcatccaatt tggtaccggg ggtcccatca   180
aggttcagtg gtactggatc tgggacagat ttttccttca ccatcagcag cctgcagcct   240
gaagatattg caacatatta ctgtcaacac tattatgatc tcccgctcac tttcggcgga   300
gggaccacgg tggcgatcag a                                             321
```

<210> SEQ ID NO 72
<211> LENGTH: 107
<212> TYPE: PRT
<213> ORGANISM: Artificial Sequence

```
<220> FEATURE:
<223> OTHER INFORMATION: synthetic

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Val Pro Gly Val Pro Ser Arg Phe Ser Gly
50                  55                  60

Thr Gly Ser Gly Thr Asp Phe Ser Phe Thr Ile Ser Ser Leu Gln Pro
65                  70                  75                  80

Glu Asp Ile Ala Thr Tyr Tyr Cys Gln His Tyr Tyr Asp Leu Pro Leu
                85                  90                  95

Thr Phe Gly Gly Gly Thr Thr Val Ala Ile Arg
            100                 105

<210> SEQ ID NO 73
<211> LENGTH: 645
<212> TYPE: DNA
<213> ORGANISM: Artificial Sequence
<220> FEATURE:
<223> OTHER INFORMATION: synthetic

<400> SEQUENCE: 73
gacatccaga tgacccagtc tccatcctcc ctgtctgcat ctgtaggaga cagagtcacc      60
atcacttgcc aggcgagtca ggacattaac aactatttaa attggtatca gcagaaacca    120
gggaaagccc ctaagctcct gatctacgat gcatccaatt tggtaccggg ggtcccatca    180
aggttcagtg gtactggatc tgggacagat ttttccttca ccatcagcag cctgcagcct    240
gaagatattg caacatatta ctgtcaacac tattatgatc tcccgctcac tttcggcgga    300
gggaccacgg tggcgatcag acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 74
<211> LENGTH: 214
<212> TYPE: PRT
<213> ORGANISM: Artificial Sequence
<220> FEATURE:
<223> OTHER INFORMATION: synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Val Pro Gly Val Pro Ser Arg Phe Ser Gly
50                  55                  60
```

```
Thr Gly Ser Gly Thr Asp Phe Ser Phe Thr Ile Ser Ser Leu Gln Pro
 65                  70                  75                  80

Glu Asp Ile Ala Thr Tyr Tyr Cys Gln His Tyr Tyr Asp Leu Pro Leu
                 85                  90                  95

Thr Phe Gly Gly Gly Thr Thr Val Ala Ile Arg Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210

<210> SEQ ID NO 75
<211> LENGTH: 348
<212> TYPE: DNA
<213> ORGANISM: Artificial Sequence
<220> FEATURE:
<223> OTHER INFORMATION: synthetic

<400> SEQUENCE: 75
gaaatacaac tggtagagtc tgggggtgac ttggtccagc ctggggggtc cctgaaactc      60
tcctgtgcag cctctggatt caccttcagt gactctgcta tgcactgggt ccgccaggct     120
tccgggaaag gctggagtg ggttggccgt attagaaaca agctaacac ttacgcgaca       180 tcatacgctg cgtcggtgaa aggcaggttc accgtctcca cagatgattc aaagaccacg     240
gcgtatctgc agatgagata cctgaaaatc gaggacacgg ccatctatta ctgtactagt     300
gaccaatttg actactgggg ccagggaacc ctggtcaccg tctcctca                  348

<210> SEQ ID NO 76
<211> LENGTH: 116
<212> TYPE: PRT
<213> ORGANISM: Artificial Sequence
<220> FEATURE:
<223> OTHER INFORMATION: synthetic

<400> SEQUENCE: 76

Glu Ile Gln Leu Val Glu Ser Gly Gly Asp Leu Val Gln Pro Gly Gly
  1               5                  10                  15

Ser Leu Lys Leu Ser Cys Ala Ala Ser Gly Phe Thr Phe Ser Asp Ser
             20                  25                  30

Ala Met His Trp Val Arg Gln Ala Ser Gly Lys Gly Leu Glu Trp Val
         35                  40                  45

Gly Arg Ile Arg Asn Lys Ala Asn Thr Tyr Ala Thr Ser Tyr Ala Ala
     50                  55                  60

Ser Val Lys Gly Arg Phe Thr Val Ser Thr Asp Asp Ser Lys Thr Thr
 65                  70                  75                  80

Ala Tyr Leu Gln Met Arg Tyr Leu Lys Ile Glu Asp Thr Ala Ile Tyr
                 85                  90                  95
```

Tyr Cys Thr Ser Asp Gln Phe Asp Tyr Trp Gly Gln Gly Thr Leu Val
            100                 105                 110

Thr Val Ser Ser
        115

<210> SEQ ID NO 77
<211> LENGTH: 24
<212> TYPE: DNA
<213> ORGANISM: Artificial Sequence
<220> FEATURE:
<223> OTHER INFORMATION: synthetic

<400> SEQUENCE: 77
ggattcacct tcagtgactc tgct                                              24

<210> SEQ ID NO 78
<211> LENGTH: 8
<212> TYPE: PRT
<213> ORGANISM: Artificial Sequence
<220> FEATURE:
<223> OTHER INFORMATION: synthetic

<400> SEQUENCE: 78

Gly Phe Thr Phe Ser Asp Ser Ala
1               5

<210> SEQ ID NO 79
<211> LENGTH: 30
<212> TYPE: DNA
<213> ORGANISM: Artificial Sequence
<220> FEATURE:
<223> OTHER INFORMATION: synthetic

<400> SEQUENCE: 79
attagaaaca aagctaacac ttacgcgaca                                        30

<210> SEQ ID NO 80
<211> LENGTH: 10
<212> TYPE: PRT
<213> ORGANISM: Artificial Sequence
<220> FEATURE:
<223> OTHER INFORMATION: synthetic

<400> SEQUENCE: 80

Ile Arg Asn Lys Ala Asn Thr Tyr Ala Thr
1               5                   10

<210> SEQ ID NO 81
<211> LENGTH: 21
<212> TYPE: DNA
<213> ORGANISM: Artificial Sequence
<220> FEATURE:
<223> OTHER INFORMATION: synthetic

<400> SEQUENCE: 81
actagtgacc aatttgacta c                                                 21

<210> SEQ ID NO 82
<211> LENGTH: 6
<212> TYPE: PRT
<213> ORGANISM: Artificial Sequence
<220> FEATURE:
<223> OTHER INFORMATION: synthetic

<400> SEQUENCE: 82

Thr Ser Asp Gln Phe Asp
1               5

<210> SEQ ID NO 83
<211> LENGTH: 336
<212> TYPE: DNA
<213> ORGANISM: Artificial Sequence
<220> FEATURE:
<223> OTHER INFORMATION: synthetic

<400> SEQUENCE: 83

```
gatgttgtga tgactcagtc tccactctcc ctgtccgcca cccttggaca gccggcctcc    60
atctcctgca ggtctagtca aagcctcgta tacagtgatg gaatcaccta cttgacttgg   120
tttcaacaga ggccaggcca atctccaacg cgcctgattt atcaggtttc taaccgggac   180
tctggagtcc cagacagatt caacggcagt gggtcaggca ctgatttac actgaacatc    240
agcagggtgg aggctgaaga tgttggattt tattactgca tggaaggaac acactggccg   300
tggacgttcg gccaagggac caaggtggag ctcaaa                             336
```

<210> SEQ ID NO 84
<211> LENGTH: 112
<212> TYPE: PRT
<213> ORGANISM: Artificial Sequence
<220> FEATURE:
<223> OTHER INFORMATION: synthetic

<400> SEQUENCE: 84

Asp Val Val Met Thr Gln Ser Pro Leu Ser Leu Ser Ala Thr Leu Gly
1               5                   10                  15

Gln Pro Ala Ser Ile Ser Cys Arg Ser Ser Gln Ser Leu Val Tyr Ser
            20                  25                  30

Asp Gly Ile Thr Tyr Leu Thr Trp Phe Gln Gln Arg Pro Gly Gln Ser
        35                  40                  45

Pro Thr Arg Leu Ile Tyr Gln Val Ser Asn Arg Asp Ser Gly Val Pro
    50                  55                  60

Asp Arg Phe Asn Gly Ser Gly Ser Gly Thr Asp Phe Thr Leu Asn Ile
65                  70                  75                  80

Ser Arg Val Glu Ala Glu Asp Val Gly Phe Tyr Tyr Cys Met Glu Gly
                85                  90                  95

Thr His Trp Pro Trp Thr Phe Gly Gln Gly Thr Lys Val Glu Leu Lys
            100                 105                 110

<210> SEQ ID NO 85
<211> LENGTH: 33
<212> TYPE: DNA
<213> ORGANISM: Artificial Sequence
<220> FEATURE:
<223> OTHER INFORMATION: synthetic

<400> SEQUENCE: 85

```
caaagcctcg tatacagtga tggaatcacc tac                                 33
```

<210> SEQ ID NO 86
<211> LENGTH: 11
<212> TYPE: PRT
<213> ORGANISM: Artificial Sequence
<220> FEATURE:
<223> OTHER INFORMATION: synthetic

<400> SEQUENCE: 86

Gln Ser Leu Val Tyr Ser Asp Gly Ile Thr Tyr
1               5                   10

<210> SEQ ID NO 87
<211> LENGTH: 9
<212> TYPE: DNA
<213> ORGANISM: Artificial Sequence
<220> FEATURE:
<223> OTHER INFORMATION: synthetic

<400> SEQUENCE: 87 caggtttct                                                                 9

<210> SEQ ID NO 88
<211> LENGTH: 3
<212> TYPE: PRT
<213> ORGANISM: Artificial Sequence
<220> FEATURE:
<223> OTHER INFORMATION: synthetic

<400> SEQUENCE: 88

Gln Val Ser
1

<210> SEQ ID NO 89
<211> LENGTH: 27
<212> TYPE: DNA
<213> ORGANISM: Artificial Sequence
<220> FEATURE:
<223> OTHER INFORMATION: synthetic

<400> SEQUENCE: 89
atggaaggaa cacactggcc gtggacg                                            27

<210> SEQ ID NO 90
<211> LENGTH: 9
<212> TYPE: PRT
<213> ORGANISM: Artificial Sequence
<220> FEATURE:
<223> OTHER INFORMATION: synthetic

<400> SEQUENCE: 90

Met Glu Gly Thr His Trp Pro Trp Thr
1               5

<210> SEQ ID NO 91
<211> LENGTH: 1332
<212> TYPE: DNA
<213> ORGANISM: Artificial Sequence
<220> FEATURE:
<223> OTHER INFORMATION: synthetic

<400> SEQUENCE: 91
gaaatacaac tggtagagtc tggggggtgac ttggtccagc ctggggggtc cctgaaactc        60
tcctgtgcag cctctggatt caccttcagt gactctgcta tgcactgggt ccgccaggct       120
tccgggaaag gctggagtg gttggccgt attagaaaca agctaacac ttacgcgaca          180 tcatacgctg cgtcggtgaa aggcaggttc accgtctcca cagatgattc aaagaccacg       240
gcgtatctgc agatgagata cctgaaaatc gaggacacgg ccatctatta ctgtactagt       300
gaccaatttg actactgggg ccagggaacc ctggtcaccg tctcctcagc ctccaccaag       360
ggcccatcgg tcttcccccct ggcgccctgc tccaggagca cctccgagag cacagccgcc     420

```
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cgaagaccta cacctgcaac      600
gtagatcaca agcccagcaa caccaaggtg gacaagagag ttgagtccaa atatggtccc      660
ccatgcccac cctgcccagc acctgagttc ctggggggac catcagtctt cctgttcccc      720
ccaaaaccca aggacactct catgatctcc cggacccctg aggtcacgtg cgtggtggtg      780
gacgtgagcc aggaagaccc cgaggtccag ttcaactggt acgtggatgg cgtggaggtg      840
cataatgcca agacaaagcc gcgggaggag cagttcaaca gcacgtaccg tgtggtcagc      900
gtcctcaccg tcctgcacca ggactggctg aacggcaagg agtacaagtg caaggtctcc      960
aacaaaggcc tcccgtcctc catcgagaaa accatctcca aagccaaagg gcagccccga     1020
gagccacagg tgtacaccct gcccccatcc caggaggaga tgaccaagaa ccaggtcagc     1080
ctgacctgcc tggtcaaagg cttctacccc agcgacatcg ccgtggagtg ggagagcaat     1140
gggcagccgg agaacaacta caagaccacg cctcccgtgc tggactccga cggctccttc     1200
ttcctctaca gcaggctcac cgtggacaag agcaggtggc aggaggggaa tgtcttctca     1260
tgctccgtga tgcatgaggc tctgcacaac cactacacac agaagtccct ctccctgtct     1320
ctgggtaaat ga                                                          1332
```

<210> SEQ ID NO 92
<211> LENGTH: 443
<212> TYPE: PRT
<213> ORGANISM: Artificial Sequence
<220> FEATURE:
<223> OTHER INFORMATION: synthetic

<400> SEQUENCE: 92

```
Glu Ile Gln Leu Val Glu Ser Gly Gly Asp Leu Val Gln Pro Gly Gly
1               5                   10                  15

Ser Leu Lys Leu Ser Cys Ala Ala Ser Gly Phe Thr Phe Ser Asp Ser
            20                  25                  30

Ala Met His Trp Val Arg Gln Ala Ser Gly Lys Gly Leu Glu Trp Val
        35                  40                  45

Gly Arg Ile Arg Asn Lys Ala Asn Thr Tyr Ala Thr Ser Tyr Ala Ala
    50                  55                  60

Ser Val Lys Gly Arg Phe Thr Val Ser Thr Asp Asp Ser Lys Thr Thr
65                  70                  75                  80

Ala Tyr Leu Gln Met Arg Tyr Leu Lys Ile Glu Asp Thr Ala Ile Tyr
                85                  90                  95

Tyr Cys Thr Ser Asp Gln Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
            435                 440

<210> SEQ ID NO 93
<211> LENGTH: 660
<212> TYPE: DNA
<213> ORGANISM: Artificial Sequence
<220> FEATURE:
<223> OTHER INFORMATION: synthetic

<400> SEQUENCE: 93
gatgttgtga tgactcagtc tccactctcc ctgtccgcca cccttggaca gccggcctcc      60
atctcctgca ggtctagtca aagcctcgta tacagtgatg gaatcaccta cttgacttgg     120
tttcaacaga ggccaggcca atctccaacg cgcctgattt atcaggtttc taaccgggac     180
tctggagtcc cagacagatt caacggcagt gggtcaggca ctgattttac actgaacatc     240
agcagggtgg aggctgaaga tgttggattt tattactgca tggaaggaac acactggccg     300
tggacgttcg gccaagggac caaggtggag ctcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

-continued

<210> SEQ ID NO 94
<211> LENGTH: 219
<212> TYPE: PRT
<213> ORGANISM: Artificial Sequence
<220> FEATURE:
<223> OTHER INFORMATION: synthetic

<400> SEQUENCE: 94

Asp Val Val Met Thr Gln Ser Pro Leu Ser Leu Ser Ala Thr Leu Gly
1               5                   10                  15

Gln Pro Ala Ser Ile Ser Cys Arg Ser Ser Gln Ser Leu Val Tyr Ser
            20                  25                  30

Asp Gly Ile Thr Tyr Leu Thr Trp Phe Gln Gln Arg Pro Gly Gln Ser
        35                  40                  45

Pro Thr Arg Leu Ile Tyr Gln Val Ser Asn Arg Asp Ser Gly Val Pro
    50                  55                  60

Asp Arg Phe Asn Gly Ser Gly Ser Gly Thr Asp Phe Thr Leu Asn Ile
65                  70                  75                  80

Ser Arg Val Glu Ala Glu Asp Val Gly Phe Tyr Tyr Cys Met Glu Gly
                85                  90                  95

Thr His Trp Pro Trp Thr Phe Gly Gln Gly Thr Lys Val Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 95
<211> LENGTH: 342
<212> TYPE: DNA
<213> ORGANISM: Artificial Sequence
<220> FEATURE:
<223> OTHER INFORMATION: synthetic

<400> SEQUENCE: 95
caggtgcagc tggtggagtc tgggggaggc ttggtcaagc ctggagggtc cctgagactc      60
tcctgtgcag cctctggatt caccttcagt gactactata tgagttggat ccgccaggct     120
ccagggaagg ggctggagtg gatttctttt attagtagaa ctggtagtac caaatactac     180
gcagactctg tgaagggccg attcaccatc tccagggaca acgccaagaa ttcactgaat     240
ctacaaatga gcagcctgag agccgaggac acggccgtgt atttctgtgc gagagagcca     300
ctacaacact ggggccaggg caccctggtt accgtctcct ca                         342

<210> SEQ ID NO 96
<211> LENGTH: 114
<212> TYPE: PRT
<213> ORGANISM: Artificial Sequence
<220> FEATURE:
<223> OTHER INFORMATION: synthetic

<400> SEQUENCE: 96

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Phe Ile Ser Arg Thr Gly Ser Thr Lys Tyr Tyr Ala Asp Ser Val
    50                  55                  60

Lys Gly Arg Phe Thr Ile Ser Arg Asp Asn Ala Lys Asn Ser Leu Asn
65                  70                  75                  80

Leu Gln Met Ser Ser Leu Arg Ala Glu Asp Thr Ala Val Tyr Phe Cys
                85                  90                  95

Ala Arg Glu Pro Leu Gln His Trp Gly Gln Gly Thr Leu Val Thr Val
            100                 105                 110

Ser Ser

<210> SEQ ID NO 97
<211> LENGTH: 24
<212> TYPE: DNA
<213> ORGANISM: Artificial Sequence
<220> FEATURE:
<223> OTHER INFORMATION: synthetic

<400> SEQUENCE: 97
ggattcacct tcagtgacta ctat                                          24

<210> SEQ ID NO 98
<211> LENGTH: 8
<212> TYPE: PRT
<213> ORGANISM: Artificial Sequence
<220> FEATURE:
<223> OTHER INFORMATION: synthetic

<400> SEQUENCE: 98

Gly Phe Thr Phe Ser Asp Tyr Tyr
1               5

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
attagtagaa ctggtagtac caaa                                          24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Ile Ser Arg Thr Gly Ser Thr Lys
1               5

<210> SEQ ID NO 101
<211> LENGTH: 21
<212> TYPE: DNA
<213> ORGANISM: Artificial Sequence
<220> FEATURE:
<223> OTHER INFORMATION: synthetic

<400> SEQUENCE: 101
gcgagagagc cactacaaca c                                       21

<210> SEQ ID NO 102
<211> LENGTH: 7
<212> TYPE: PRT
<213> ORGANISM: Artificial Sequence
<220> FEATURE:
<223> OTHER INFORMATION: synthetic

<400> SEQUENCE: 102

Ala Arg Glu Pro Leu Gln His
1               5

<210> SEQ ID NO 103
<211> LENGTH: 339
<212> TYPE: DNA
<213> ORGANISM: Artificial Sequence
<220> FEATURE:
<223> OTHER INFORMATION: synthetic

<400> SEQUENCE: 103
aatgttgtgc tgacccagac tccaatttcc tcacctgtca tccttggaca gccggcctcc    60
atctcctgca ggtctagtca aagcctcgta cacagtgatg agacaccta cttgagttgg   120 cttcatcaga ggccaggcca gcctccaaga ctcctaattt atacggtttc taaccgggtg   180
tctggggtcc cagacagatt cagtggcagt ggggcaggga cagatttcac actgaaaatc   240
agtagggtgg aagctgagga tgtcggggtt tattactgca tgcaaggaac acaatttccc   300
gcgctcactt tcggcggagg gaccaaggtg gagatcaaa                          339

<210> SEQ ID NO 104
<211> LENGTH: 113
<212> TYPE: PRT
<213> ORGANISM: Artificial Sequence
<220> FEATURE:
<223> OTHER INFORMATION: synthetic

<400> SEQUENCE: 104

Asn Val Val Leu Thr Gln Thr Pro Ile Ser Ser Pro Val Ile Leu Gly
1               5                   10                  15

Gln Pro Ala Ser Ile Ser Cys Arg Ser Ser Gln Ser Leu Val His Ser
            20                  25                  30

Asp Gly Asp Thr Tyr Leu Ser Trp Leu His Gln Arg Pro Gly Gln Pro
        35                  40                  45

Pro Arg Leu Leu Ile Tyr Thr Val Ser Asn Arg Val Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Gln Phe Pro Ala Leu Thr Phe Gly Gly Gly Thr Lys Val Glu Ile
            100                 105                 110

Lys

```
<210> SEQ ID NO 105
<211> LENGTH: 33
<212> TYPE: DNA
<213> ORGANISM: Artificial Sequence
<220> FEATURE:
<223> OTHER INFORMATION: synthetic

<400> SEQUENCE: 105
caaagcctcg tacacagtga tggagacacc tac                                    33

<210> SEQ ID NO 106
<211> LENGTH: 11
<212> TYPE: PRT
<213> ORGANISM: Artificial Sequence
<220> FEATURE:
<223> OTHER INFORMATION: synthetic

<400> SEQUENCE: 106

Gln Ser Leu Val His Ser Asp Gly Asp Thr Tyr
1               5                   10

<210> SEQ ID NO 107
<211> LENGTH: 9
<212> TYPE: DNA
<213> ORGANISM: Artificial Sequence
<220> FEATURE:
<223> OTHER INFORMATION: synthetic

<400> SEQUENCE: 107 acggtttct                                                               9

<210> SEQ ID NO 108
<211> LENGTH: 3
<212> TYPE: PRT
<213> ORGANISM: Artificial Sequence
<220> FEATURE:
<223> OTHER INFORMATION: synthetic

<400> SEQUENCE: 108

Thr Val Ser
1

<210> SEQ ID NO 109
<211> LENGTH: 30
<212> TYPE: DNA
<213> ORGANISM: Artificial Sequence
<220> FEATURE:
<223> OTHER INFORMATION: synthetic

<400> SEQUENCE: 109
atgcaaggaa cacaatttcc cgcgctcact                                        30

<210> SEQ ID NO 110
<211> LENGTH: 10
<212> TYPE: PRT
<213> ORGANISM: Artificial Sequence
<220> FEATURE:
<223> OTHER INFORMATION: synthetic

<400> SEQUENCE: 110

Met Gln Gly Thr Gln Phe Pro Ala Leu Thr
1               5                   10

<210> SEQ ID NO 111
<211> LENGTH: 1326
<212> TYPE: DNA
<213> ORGANISM: Artificial Sequence
```

```
<220> FEATURE:
<223> OTHER INFORMATION: synthetic

<400> SEQUENCE: 111
caggtgcagc tggtggagtc tgggggaggc ttggtcaagc ctggagggtc cctgagactc      60
tcctgtgcag cctctggatt caccttcagt gactactata tgagttggat ccgccaggct     120
ccagggaagg ggctggagtg gatttctttt attagtagaa ctggtagtac caaatactac     180
gcagactctg tgaagggccg attcaccatc tccaggaca acgccaagaa ttcactgaat      240
ctacaaatga gcagcctgag agccgaggac acggccgtgt atttctgtgc gagagagcca     300
ctacaacact ggggccaggg caccctggtt accgtctcct cagcctccac caagggccca     360
tcggtcttcc ccctggcgcc ctgctccagg agcacctccg agagcacagc cgccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc cagcagcttg ggcacgaaga cctacacctg caacgtagat     600
cacaagccca gcaacaccaa ggtggacaag agagttgagt ccaaatatgg tcccccatgc     660
ccaccctgcc cagcacctga gttcctgggg ggaccatcag tcttcctgtt ccccccaaaa     720
cccaaggaca ctctcatgat ctcccggacc cctgaggtca cgtgcgtggt ggtggacgtg     780
agccaggaag accccgaggt ccagttcaac tggtacgtgg atggcgtgga ggtgcataat     840
gccaagacaa agccgcggga ggagcagttc aacagcacgt accgtgtggt cagcgtcctc     900
accgtcctgc accaggactg gctgaacggc aaggagtaca agtgcaaggt ctccaacaaa     960
ggcctcccgt cctccatcga gaaaaccatc tccaaagcca agggcagccc cgagagcca    1020
caggtgtaca ccctgccccc atcccaggag gagatgacca gaaccaggt cagcctgacc    1080
tgcctggtca aaggcttcta ccccagcgac atcgccgtgg agtgggagag caatgggcag    1140
ccggagaaca actacaagac cacgcctccc gtgctggact ccgacggctc cttcttcctc    1200
tacagcaggc tcaccgtgga caagagcagg tggcaggagg ggaatgtctt ctcatgctcc    1260
gtgatgcatg aggctctgca caaccactac acacagaagt ccctctccct gtctctgggt    1320
aaatga                                                              1326

<210> SEQ ID NO 112
<211> LENGTH: 441
<212> TYPE: PRT
<213> ORGANISM: Artificial Sequence
<220> FEATURE:
<223> OTHER INFORMATION: synthetic

<400> SEQUENCE: 112

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Phe Ile Ser Arg Thr Gly Ser Thr Lys Tyr Tyr Ala Asp Ser Val
    50                  55                  60

Lys Gly Arg Phe Thr Ile Ser Arg Asp Asn Ala Lys Asn Ser Leu Asn
65                  70                  75                  80

Leu Gln Met Ser Ser Leu Arg Ala Glu Asp Thr Ala Val Tyr Phe Cys
                85                  90                  95
```

Ala Arg Glu Pro Leu Gln His Trp Gly Gln Gly Thr Leu Val Thr Val
                100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
210                 215                 220

Ala Pro Glu Phe Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys
        435                 440

<210> SEQ ID NO 113
<211> LENGTH: 663
<212> TYPE: DNA
<213> ORGANISM: Artificial Sequence
<220> FEATURE:
<223> OTHER INFORMATION: synthetic

<400> SEQUENCE: 113
aatgttgtgc tgacccagac tccaatttcc tcacctgtca tccttggaca gccggcctcc    60
atctcctgca ggtctagtca aagcctcgta cacagtgatg agacaccta cttgagttgg    120

```
cttcatcaga ggccaggcca gcctccaaga ctcctaattt atacggtttc taaccgggtg    180
tctggggtcc cagacagatt cagtggcagt ggggcaggga cagatttcac actgaaaatc    240
agtagggtgg aagctgagga tgtcggggtt tattactgca tgcaaggaac acaatttccc    300
gcgctcactt tcggcggagg gaccaaggtg gagatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tag                                                                  663
```

<210> SEQ ID NO 114
<211> LENGTH: 220
<212> TYPE: PRT
<213> ORGANISM: Artificial Sequence
<220> FEATURE:
<223> OTHER INFORMATION: synthetic

<400> SEQUENCE: 114

```
Asn Val Val Leu Thr Gln Thr Pro Ile Ser Ser Pro Val Ile Leu Gly
1               5                   10                  15

Gln Pro Ala Ser Ile Ser Cys Arg Ser Ser Gln Ser Leu Val His Ser
            20                  25                  30

Asp Gly Asp Thr Tyr Leu Ser Trp Leu His Gln Arg Pro Gly Gln Pro
        35                  40                  45

Pro Arg Leu Leu Ile Tyr Thr Val Ser Asn Arg Val Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Gln Phe Pro Ala Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 115
<211> LENGTH: 342
<212> TYPE: DNA
<213> ORGANISM: Artificial Sequence
<220> FEATURE:
<223> OTHER INFORMATION: synthetic

<400> SEQUENCE: 115

```
caggtgcagc tggttgagtc tgggggaggc ttggtcaagc ctggagggtc cctgagactc      60
tcctgtgcag cctctggatt caccttcagt gactactaca tgagctggat ccgccaggct     120
ccagggaagg gactggagtg gtttcatat attagtagaa ctggtagtac caaatattac     180
gcagactctg tgaagggccg attcaccatc tccagggaca acgccaaaaa ctcactgaat     240
ctacaaatga gcagcctgag agccgaggac acggccgtgt atttctgtgc gagagagcca     300
ctacaacact ggggccaggg caccctggtt accgtctcct ca                        342
```

<210> SEQ ID NO 116
<211> LENGTH: 114
<212> TYPE: PRT
<213> ORGANISM: Artificial Sequence
<220> FEATURE:
<223> OTHER INFORMATION: synthetic

<400> SEQUENCE: 116

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Thr Gly Ser Thr Lys Tyr Tyr Ala Asp Ser Val
    50                  55                  60

Lys Gly Arg Phe Thr Ile Ser Arg Asp Asn Ala Lys Asn Ser Leu Asn
65                  70                  75                  80

Leu Gln Met Ser Ser Leu Arg Ala Glu Asp Thr Ala Val Tyr Phe Cys
                85                  90                  95

Ala Arg Glu Pro Leu Gln His Trp Gly Gln Gly Thr Leu Val Thr Val
            100                 105                 110

Ser Ser
```

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117

```
ggattcacct tcagtgacta ctac                                             24
```

<210> SEQ ID NO 118
<211> LENGTH: 339
<212> TYPE: DNA
<213> ORGANISM: Artificial Sequence
<220> FEATURE:
<223> OTHER INFORMATION: synthetic

<400> SEQUENCE: 118

```
aaaattgtgc tgacccagac tccactctcc tcacctgtca cccttggaca gccggcctcc      60
atctcctgca ggtctagtca aagccttgta cacagtgatg agacacccta cttgagttgg     120
cttcaccaga ggccaggcca gcctccaaga ctcctaatat atacgatttc taaccggttg     180
tctggggtcc cagacagatt cagtggcagt ggggcaggga cagatttcac actgaaaatc     240
```

```
agtagggtgg aagctgagga tgtcggggtt tattactgca tgcaaggaac acaatttccc    300
gcgctcactt tcggcggagg gaccaaggtg gagatcaaa                            339
```

<210> SEQ ID NO 119
<211> LENGTH: 113
<212> TYPE: PRT
<213> ORGANISM: Artificial Sequence
<220> FEATURE:
<223> OTHER INFORMATION: synthetic

<400> SEQUENCE: 119

Lys Ile Val Leu Thr Gln Thr Pro Leu Ser Pro Val Thr Leu Gly
1               5                  10                  15

Gln Pro Ala Ser Ile Ser Cys Arg Ser Ser Gln Ser Leu Val His Ser
            20                  25                  30

Asp Gly Asp Thr Tyr Leu Ser Trp Leu His Gln Arg Pro Gly Gln Pro
        35                  40                  45

Pro Arg Leu Leu Ile Tyr Thr Ile Ser Asn Arg Leu Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Gln Phe Pro Ala Leu Thr Phe Gly Gly Gly Thr Lys Val Glu Ile
            100                 105                 110

Lys

<210> SEQ ID NO 120
<211> LENGTH: 33
<212> TYPE: DNA
<213> ORGANISM: Artificial Sequence
<220> FEATURE:
<223> OTHER INFORMATION: synthetic

<400> SEQUENCE: 120

```
caaagccttg tacacagtga tggagacacc tac                                  33
```

<210> SEQ ID NO 121
<211> LENGTH: 9
<212> TYPE: DNA
<213> ORGANISM: Artificial Sequence
<220> FEATURE:
<223> OTHER INFORMATION: synthetic

<400> SEQUENCE: 121

```
acgatttct                                                              9
```

<210> SEQ ID NO 122
<211> LENGTH: 3
<212> TYPE: PRT
<213> ORGANISM: Artificial Sequence
<220> FEATURE:
<223> OTHER INFORMATION: synthetic

<400> SEQUENCE: 122

Thr Ile Ser
1

<210> SEQ ID NO 123
<211> LENGTH: 1326
<212> TYPE: DNA
<213> ORGANISM: Artificial Sequence
<220> FEATURE:
<223> OTHER INFORMATION: synthetic

<400> SEQUENCE: 123

```
caggtgcagc tggttgagtc tgggggaggc ttggtcaagc ctggagggtc cctgagactc      60
tcctgtgcag cctctggatt caccttcagt gactactaca tgagctggat ccgccaggct     120
ccagggaagg gactggagtg ggtttcatat attagtagaa ctggtagtac caaatattac     180
gcagactctg tgaagggccg attcaccatc tccaggaca acgccaaaaa ctcactgaat      240
ctacaaatga gcagcctgag agccgaggac acggccgtgt atttctgtgc gagagagcca     300
ctacaacact ggggccaggg caccctggtt accgtctcct cagcctccac caagggccca     360
tcggtcttcc ccctggcgcc ctgctccagg agcacctccg agagcacagc cgccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc cagcagcttg ggcacgaaga cctacacctg caacgtagat     600
cacaagccca gcaacaccaa ggtggacaag agagttgagt ccaaatatgg tcccccatgc     660
ccaccctgcc cagcacctga gttcctgggg ggaccatcag tcttcctgtt ccccccaaaa     720
cccaaggaca ctctcatgat ctcccggacc cctgaggtca cgtgcgtggt ggtggacgtg     780
agccaggaag accccgaggt ccagttcaac tggtacgtgg atggcgtgga ggtgcataat     840
gccaagacaa agccgcggga ggagcagttc aacagcacgt accgtgtggt cagcgtcctc     900
accgtcctgc accaggactg gctgaacggc aaggagtaca agtgcaaggt ctccaacaaa     960
ggcctcccgt cctccatcga gaaaaccatc tccaaagcca agggcagcc cgagagcca    1020
caggtgtaca ccctgccccc atcccaggag gagatgacca gaaccaggt cagcctgacc    1080
tgcctggtca aaggcttcta ccccagcgac atcgccgtgg agtgggagag caatgggcag    1140
ccggagaaca actacaagac cacgcctccc gtgctggact ccgacggctc cttcttcctc    1200
tacagcaggc tcaccgtgga caagagcagg tggcaggagg ggaatgtctt ctcatgctcc    1260
gtgatgcatg aggctctgca caaccactac acacagaagt ccctctccct gtctctgggt    1320
aaatga                                                              1326
```

<210> SEQ ID NO 124
<211> LENGTH: 441
<212> TYPE: PRT
<213> ORGANISM: Artificial Sequence
<220> FEATURE:
<223> OTHER INFORMATION: synthetic

<400> SEQUENCE: 124

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Thr Gly Ser Thr Lys Tyr Tyr Ala Asp Ser Val
    50                  55                  60

Lys Gly Arg Phe Thr Ile Ser Arg Asp Asn Ala Lys Asn Ser Leu Asn
65                  70                  75                  80

Leu Gln Met Ser Ser Leu Arg Ala Glu Asp Thr Ala Val Tyr Phe Cys
                85                  90                  95
```

Ala Arg Glu Pro Leu Gln His Trp Gly Gln Gly Thr Leu Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Phe Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys
        435                 440

<210> SEQ ID NO 125
<211> LENGTH: 663
<212> TYPE: DNA
<213> ORGANISM: Artificial Sequence
<220> FEATURE:
<223> OTHER INFORMATION: synthetic

<400> SEQUENCE: 125
aaaattgtgc tgacccagac tccactctcc tcacctgtca cccttggaca gccggcctcc     60
atctcctgca ggtctagtca aagccttgta cacagtgatg agacaccta cttgagttgg    120

```
cttcaccaga ggccaggcca gcctccaaga ctcctaatat atacgatttc taaccggttg    180
tctggggtcc cagacagatt cagtggcagt ggggcaggga cagatttcac actgaaaatc    240
agtagggtgg aagctgagga tgtcggggtt tattactgca tgcaaggaac acaatttccc    300
gcgctcactt tcggcggagg gaccaaggtg gagatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tag                                                                   663
```

```
<210> SEQ ID NO 126
<211> LENGTH: 220
<212> TYPE: PRT
<213> ORGANISM: Artificial Sequence
<220> FEATURE:
<223> OTHER INFORMATION: synthetic

<400> SEQUENCE: 126
```

Lys Ile Val Leu Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asp Thr Tyr Leu Ser Trp Leu His Gln Arg Pro Gly Gln Pro
        35                  40                  45

Pro Arg Leu Leu Ile Tyr Thr Ile Ser Asn Arg Leu Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Gln Phe Pro Ala Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

```
<210> SEQ ID NO 127
<211> LENGTH: 345
<212> TYPE: DNA
<213> ORGANISM: Artificial Sequence
<220> FEATURE:
<223> OTHER INFORMATION: synthetic
```

<400> SEQUENCE: 127

```
gagatgcagc tggtggagtc tggggggaggc ttggtccagc ctggggggtc gctgaaagtc      60
tcctgtgcag cctctgggtt caccctcagt gactcttcta tacactgggt ccgccaggct     120
tccgggaaag gctggagtg gattggccgt atcagaagca aaccttacag ttacgcgaca      180
gcatatgctg cgtcggtgaa aggcaggttc accatttcta gagatgattc aaagaacacg     240
gcgtttctgc aaatgagcgg cctgaaaacc gaggacacgg ccgtctatta ttgtactggg     300
ggggatgact tctggggcca gggaaccctg gtcaccgtct cctca                     345
```

<210> SEQ ID NO 128
<211> LENGTH: 115
<212> TYPE: PRT
<213> ORGANISM: Artificial Sequence
<220> FEATURE:
<223> OTHER INFORMATION: synthetic

<400> SEQUENCE: 128

```
Glu Met Gln Leu Val Glu Ser Gly Gly Gly Leu Val Gln Pro Gly Gly
1               5                   10                  15

Ser Leu Lys Val Ser Cys Ala Ala Ser Gly Phe Thr Leu Ser Asp Ser
            20                  25                  30

Ser Ile His Trp Val Arg Gln Ala Ser Gly Lys Gly Leu Glu Trp Ile
        35                  40                  45

Gly Arg Ile Arg Ser Lys Pro Tyr Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Phe Leu Gln Met Ser Gly Leu Lys Thr Glu Asp Thr Ala Val Tyr
                85                  90                  95

Tyr Cys Thr Gly Gly Asp Asp Phe Trp Gly Gln Gly Thr Leu Val Thr
            100                 105                 110

Val Ser Ser
        115
```

<210> SEQ ID NO 129
<211> LENGTH: 24
<212> TYPE: DNA
<213> ORGANISM: Artificial Sequence
<220> FEATURE:
<223> OTHER INFORMATION: synthetic

<400> SEQUENCE: 129

```
gggttcaccc tcagtgactc ttct                                              24
```

<210> SEQ ID NO 130
<211> LENGTH: 8
<212> TYPE: PRT
<213> ORGANISM: Artificial Sequence
<220> FEATURE:
<223> OTHER INFORMATION: synthetic

<400> SEQUENCE: 130

```
Gly Phe Thr Leu Ser Asp Ser Ser
1               5
```

<210> SEQ ID NO 131
<211> LENGTH: 30
<212> TYPE: DNA
<213> ORGANISM: Artificial Sequence

```
<220> FEATURE:
<223> OTHER INFORMATION: synthetic

<400> SEQUENCE: 131
atcagaagca aaccttacag ttacgcgaca                                        30

<210> SEQ ID NO 132
<211> LENGTH: 10
<212> TYPE: PRT
<213> ORGANISM: Artificial Sequence
<220> FEATURE:
<223> OTHER INFORMATION: synthetic

<400> SEQUENCE: 132

Ile Arg Ser Lys Pro Tyr Ser Tyr Ala Thr
1               5                   10

<210> SEQ ID NO 133
<211> LENGTH: 18
<212> TYPE: DNA
<213> ORGANISM: Artificial Sequence
<220> FEATURE:
<223> OTHER INFORMATION: synthetic

<400> SEQUENCE: 133 actgggggggg atgacttc                                                    18

<210> SEQ ID NO 134
<211> LENGTH: 6
<212> TYPE: PRT
<213> ORGANISM: Artificial Sequence
<220> FEATURE:
<223> OTHER INFORMATION: synthetic

<400> SEQUENCE: 134

Thr Gly Gly Asp Asp Phe
1               5

<210> SEQ ID NO 135
<211> LENGTH: 318
<212> TYPE: DNA
<213> ORGANISM: Artificial Sequence
<220> FEATURE:
<223> OTHER INFORMATION: synthetic

<400> SEQUENCE: 135
gacatccaga tgacccagtc tccttccacc ctgtctgcat ctgttggaga cagaatcacc       60
atcacttgcc gggccagtca gagtattagt acttggttgg cctggtatca gcagaaacca     120
gggaaagccc ctaagctcct gatctataag gcgtctagtt tagaaggtgg ggtcccttca     180
aggttcagcg gcagtggatc tgggacagat ttcactctca ccatcagcag cctgcagcct     240
gatgattttg caacttatta ctgccaacaa tataatactt attggacgtt cggccaaggg     300
accaaggtgg aaatcaaa                                                   318

<210> SEQ ID NO 136
<211> LENGTH: 106
<212> TYPE: PRT
<213> ORGANISM: Artificial Sequence
<220> FEATURE:
<223> OTHER INFORMATION: synthetic

<400> SEQUENCE: 136

Asp Ile Gln Met Thr Gln Ser Pro Ser Thr Leu Ser Ala Ser Val Gly
1               5                   10                  15
```

```
Asp Arg Ile Thr Ile Thr Cys Arg Ala Ser Gln Ser Ile Ser Thr Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Gly Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Tyr Asn Thr Tyr Trp Thr
                 85                  90                  95

Phe Gly Gln Gly Thr Lys Val Glu Ile Lys
            100                 105

<210> SEQ ID NO 137
<211> LENGTH: 18
<212> TYPE: DNA
<213> ORGANISM: Artificial Sequence
<220> FEATURE:
<223> OTHER INFORMATION: synthetic

<400> SEQUENCE: 137
cagagtatta gtacttgg                                               18

<210> SEQ ID NO 138
<211> LENGTH: 6
<212> TYPE: PRT
<213> ORGANISM: Artificial Sequence
<220> FEATURE:
<223> OTHER INFORMATION: synthetic

<400> SEQUENCE: 138

Gln Ser Ile Ser Thr Trp
1               5

<210> SEQ ID NO 139
<211> LENGTH: 9
<212> TYPE: DNA
<213> ORGANISM: Artificial Sequence
<220> FEATURE:
<223> OTHER INFORMATION: synthetic

<400> SEQUENCE: 139 aaggcgtct                                                          9

<210> SEQ ID NO 140
<211> LENGTH: 3
<212> TYPE: PRT
<213> ORGANISM: Artificial Sequence
<220> FEATURE:
<223> OTHER INFORMATION: synthetic

<400> SEQUENCE: 140

Lys Ala Ser
1

<210> SEQ ID NO 141
<211> LENGTH: 24
<212> TYPE: DNA
<213> ORGANISM: Artificial Sequence
<220> FEATURE:
<223> OTHER INFORMATION: synthetic

<400> SEQUENCE: 141
caacaatata atacttattg gacg                                        24
```

<210> SEQ ID NO 142
<211> LENGTH: 8
<212> TYPE: PRT
<213> ORGANISM: Artificial Sequence
<220> FEATURE:
<223> OTHER INFORMATION: synthetic

<400> SEQUENCE: 142

Gln Gln Tyr Asn Thr Tyr Trp Thr
1               5

<210> SEQ ID NO 143
<211> LENGTH: 1329
<212> TYPE: DNA
<213> ORGANISM: Artificial Sequence
<220> FEATURE:
<223> OTHER INFORMATION: synthetic

<400> SEQUENCE: 143

```
gagatgcagc tggtggagtc tgggggaggc ttggtccagc ctggggggtc gctgaaagtc      60
tcctgtgcag cctctgggtt caccctcagt gactcttcta tacactgggt ccgccaggct     120
tccgggaaag gctggagtg gattggccgt atcagaagca aaccttacag ttacgcgaca      180
gcatatgctg cgtcggtgaa aggcaggttc accatttcta gagatgattc aaagaacacg     240
gcgtttctgc aaatgagcgg cctgaaaacc gaggacacgg ccgtctatta ttgtactggg     300
ggggatgact ctggggcca gggaaccctg gtcaccgtct cctcagcctc caccaagggc      360
ccatcggtct tccccctggc gccctgctcc aggagcacct ccgagagcac agccgccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcacga gacctacac ctgcaacgta      600
gatcacaagc ccagcaacac caaggtggac aagagagttg agtccaaata tggtccccca     660
tgcccaccct gcccagcacc tgagttcctg gggggaccat cagtcttcct gttccccca      720
aaacccaagg acactctcat gatctcccgg acccctgagg tcacgtgcgt ggtggtggac     780
gtgagccagg aagaccccga ggtccagttc aactggtacg tggatggcgt ggaggtgcat     840
aatgccaaga caaagccgcg ggaggagcag ttcaacagca cgtaccgtgt ggtcagcgtc     900
ctcaccgtcc tgcaccagga ctggctgaac ggcaaggagt acaagtgcaa ggtctccaac     960
aaaggcctcc cgtcctccat cgagaaaacc atctccaaag ccaaagggca gccccgagag    1020
ccacaggtgt acaccctgcc cccatcccag gaggagatga ccaagaacca ggtcagcctg    1080
acctgcctgg tcaaaggctt ctaccccagc gacatcgccg tggagtggga gagcaatggg    1140
cagccggaga caactacaa gaccacgcct cccgtgctgg actccgacgg ctccttcttc     1200
ctctacagca ggctcaccgt ggacaagagc aggtggcagg aggggaatgt cttctcatgc    1260
tccgtgatgc atgaggctct gcacaaccac tacacacaga gtccctctc cctgtctctg     1320
ggtaaatga                                                            1329
```

<210> SEQ ID NO 144
<211> LENGTH: 442
<212> TYPE: PRT
<213> ORGANISM: Artificial Sequence
<220> FEATURE:
<223> OTHER INFORMATION: synthetic

<400> SEQUENCE: 144

```
Glu Met Gln Leu Val Glu Ser Gly Gly Gly Leu Val Gln Pro Gly Gly
1               5                   10                  15

Ser Leu Lys Val Ser Cys Ala Ala Ser Gly Phe Thr Leu Ser Asp Ser
            20                  25                  30

Ser Ile His Trp Val Arg Gln Ala Ser Gly Lys Gly Leu Glu Trp Ile
        35                  40                  45

Gly Arg Ile Arg Ser Lys Pro Tyr Ser Tyr Ala Thr Ala Tyr Ala Ala
50                  55                  60

Ser Val Lys Gly Arg Phe Thr Ile Ser Arg Asp Asp Ser Lys Asn Thr
65                  70                  75                  80

Ala Phe Leu Gln Met Ser Gly Leu Lys Thr Glu Asp Thr Ala Val Tyr
                85                  90                  95

Tyr Cys Thr Gly Gly Asp Asp Phe Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415
```

```
Val Phe Ser Cys Ser Val Met His Glu Ala Leu His Asn His Tyr Thr
            420                 425                 430

Gln Lys Ser Leu Ser Leu Ser Leu Gly Lys
        435                 440
```

<210> SEQ ID NO 145
<211> LENGTH: 642
<212> TYPE: DNA
<213> ORGANISM: Artificial Sequence
<220> FEATURE:
<223> OTHER INFORMATION: synthetic

<400> SEQUENCE: 145

```
gacatccaga tgacccagtc tccttccacc ctgtctgcat ctgttggaga cagaatcacc    60
atcacttgcc gggccagtca gagtattagt acttggttgg cctggtatca gcagaaacca   120
gggaaagccc ctaagctcct gatctataag gcgtctagtt tagaaggtgg ggtcccttca   180
aggttcagcg gcagtggatc tgggacagat ttcactctca ccatcagcag cctgcagcct   240
gatgattttg caacttatta ctgccaacaa tataatactt attggacgtt cggccaaggg   300
accaaggtgg aaatcaaacg aactgtggct gcaccatctg tcttcatctt cccgccatct   360
gatgagcagt tgaaatctgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgtt ag                     642
```

<210> SEQ ID NO 146
<211> LENGTH: 213
<212> TYPE: PRT
<213> ORGANISM: Artificial Sequence
<220> FEATURE:
<223> OTHER INFORMATION: synthetic

<400> SEQUENCE: 146

```
Asp Ile Gln Met Thr Gln Ser Pro Ser Thr Leu Ser Ala Ser Val Gly
1               5                  10                  15

Asp Arg Ile Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
        165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 147
<211> LENGTH: 363
<212> TYPE: DNA
<213> ORGANISM: Artificial Sequence
<220> FEATURE:
<223> OTHER INFORMATION: synthetic

<400> SEQUENCE: 147
gaggtgcagc tggtggagtc tgggggaggc ttggtacagc ctgggggtc cctgagactc         60 tcctgtgcag cctctggatt cacctttagc agctatgcca tgagttgggt ccgccaggct        120
ccagggaagg gctggagtg gtctcagct attagtggta gtggtggtag cacatactac         180
gcagactccg tgaagggccg gttcaccatc tccagagaca attccaagaa cacgctgtat        240
ctgcaaatga acagcctgag agccgaggac acggccgtat attactgtgc gatcccgtat        300
aactggaact acggaggggc ttttgatatc tggggccaag ggacaatggt caccgtctct        360
tca                                                                      363

<210> SEQ ID NO 148
<211> LENGTH: 121
<212> TYPE: PRT
<213> ORGANISM: Artificial Sequence
<220> FEATURE:
<223> OTHER INFORMATION: synthetic

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Pro Tyr Asn Trp Asn Tyr Gly Gly Ala Phe Asp Ile Trp Gly
            100                 105                 110

Gln Gly Thr Met Val Thr Val Ser Ser
        115                 120

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
ggattcacct ttagcagcta tgcc                                                24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Gly Phe Thr Phe Ser Ser Tyr Ala
1               5

<210> SEQ ID NO 151
<211> LENGTH: 24
<212> TYPE: DNA
<213> ORGANISM: Artificial Sequence
<220> FEATURE:
<223> OTHER INFORMATION: synthetic

<400> SEQUENCE: 151
attagtggta gtggtggtag caca                                                24

<210> SEQ ID NO 152
<211> LENGTH: 8
<212> TYPE: PRT
<213> ORGANISM: Artificial Sequence
<220> FEATURE:
<223> OTHER INFORMATION: synthetic

<400> SEQUENCE: 152

Ile Ser Gly Ser Gly Gly Ser Thr
1               5

<210> SEQ ID NO 153
<211> LENGTH: 42
<212> TYPE: DNA
<213> ORGANISM: Artificial Sequence
<220> FEATURE:
<223> OTHER INFORMATION: synthetic

<400> SEQUENCE: 153
gcgatcccgt ataactggaa ctacggaggg gcttttgata tc                             42

<210> SEQ ID NO 154
<211> LENGTH: 14
<212> TYPE: PRT
<213> ORGANISM: Artificial Sequence
<220> FEATURE:
<223> OTHER INFORMATION: synthetic

<400> SEQUENCE: 154

Ala Ile Pro Tyr Asn Trp Asn Tyr Gly Gly Ala Phe Asp Ile
1               5                   10

<210> SEQ ID NO 155
<211> LENGTH: 324
<212> TYPE: DNA
<213> ORGANISM: Artificial Sequence
<220> FEATURE:
<223> OTHER INFORMATION: synthetic

<400> SEQUENCE: 155
gaaattgtga tgacgcagtc tccagccacc ctgtctgtgt ctccaggaa aagagccacc           60

```
ctctcctgca gggccagtca gagtgttagt agtaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcaacag tataataact ggcctccgta cacttttggc    300
caggggacca agctggagat caaa                                           324
```

```
<210> SEQ ID NO 156
<211> LENGTH: 108
<212> TYPE: PRT
<213> ORGANISM: Artificial Sequence
<220> FEATURE:
<223> OTHER INFORMATION: synthetic

<400> SEQUENCE: 156

Glu Ile Val Met Thr Gln Ser Pro Ala Thr Leu Ser Val Ser Pro Gly
1               5                   10                  15

Lys Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Tyr Thr Phe Gly Gln Gly Thr Lys Leu Glu Ile Lys
            100                 105
```

```
<210> SEQ ID NO 157
<211> LENGTH: 18
<212> TYPE: DNA
<213> ORGANISM: Artificial Sequence
<220> FEATURE:
<223> OTHER INFORMATION: synthetic

<400> SEQUENCE: 157
cagagtgtta gtagtaac                                                  18
```

```
<210> SEQ ID NO 158
<211> LENGTH: 6
<212> TYPE: PRT
<213> ORGANISM: Artificial Sequence
<220> FEATURE:
<223> OTHER INFORMATION: synthetic

<400> SEQUENCE: 158

Gln Ser Val Ser Ser Asn
1               5
```

```
<210> SEQ ID NO 159
<211> LENGTH: 30
<212> TYPE: DNA
<213> ORGANISM: Artificial Sequence
<220> FEATURE:
<223> OTHER INFORMATION: synthetic

<400> SEQUENCE: 159
caacagtata ataactggcc tccgtacact                                     30
```

-continued

<210> SEQ ID NO 160
<211> LENGTH: 10
<212> TYPE: PRT
<213> ORGANISM: Artificial Sequence
<220> FEATURE:
<223> OTHER INFORMATION: synthetic

<400> SEQUENCE: 160

Gln Gln Tyr Asn Asn Trp Pro Pro Tyr Thr
1               5                   10

<210> SEQ ID NO 161
<211> LENGTH: 1347
<212> TYPE: DNA
<213> ORGANISM: Artificial Sequence
<220> FEATURE:
<223> OTHER INFORMATION: synthetic

<400> SEQUENCE: 161
gaggtgcagc tggtggagtc tgggggaggc ttggtacagc ctggggggtc cctgagactc      60
tcctgtgcag cctctggatt cacctttagc agctatgcca tgagttgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gatcccgtat     300
aactggaact acggaggggc ttttgatatc tggggccaag ggacaatggt caccgtctct     360
tcagcctcca ccaagggccc atcggtcttc cccctggcgc cctgctccag gagcacctcc     420
gagagcacag ccgccctggg ctgcctggtc aaggactact ccccgaacc ggtgacggtg      480 tcgtggaact caggcgccct gaccagcggc gtgcacacct tcccggctgt cctacagtcc     540
tcaggactct actccctcag cagcgtggtg accgtgccct ccagcagctt gggcacgaag     600
acctacacct gcaacgtaga tcacaagccc agcaacacca aggtggacaa gagagttgag     660
tccaaatatg gtccccatg cccacccctgc ccagcacctg agttcctggg gggaccatca     720
gtcttcctgt tccccccaaa acccaaggac actctcatga tctcccggac ccctgaggtc     780
acgtgcgtgg tggtggacgt gagccaggaa gaccccgagg tccagttcaa ctggtacgtg     840
gatggcgtgg aggtgcataa tgccaagaca aagccgcggg aggagcagtt caacagcacg     900
taccgtgtgg tcagcgtcct caccgtcctg caccaggact ggctgaacgg caaggagtac     960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaga gcaatgggca gccggagaac aactacaaga ccacgcctcc cgtgctggac    1200
tccgacggct ccttcttcct ctacagcagg ctcaccgtgg acaagagcag gtggcaggag    1260
gggaatgtct tctcatgctc cgtgatgcat gaggctctgc acaaccacta cacacagaag    1320
tccctctccc tgtctctggg taaatga                                         1347

<210> SEQ ID NO 162
<211> LENGTH: 448
<212> TYPE: PRT
<213> ORGANISM: Artificial Sequence
<220> FEATURE:
<223> OTHER INFORMATION: synthetic

```
<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Pro Tyr Asn Trp Asn Tyr Gly Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
        435                 440                 445

<210> SEQ ID NO 163
<211> LENGTH: 648
<212> TYPE: DNA
<213> ORGANISM: Artificial Sequence
<220> FEATURE:
<223> OTHER INFORMATION: synthetic

<400> SEQUENCE: 163
gaaattgtga tgacgcagtc tccagccacc ctgtctgtgt ctccagggaa aagagccacc    60
ctctcctgca gggccagtca gagtgttagt agtaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcaacag tataataact ggcctccgta cacttttggc   300
caggggacca agctggagat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttag                648

<210> SEQ ID NO 164
<211> LENGTH: 215
<212> TYPE: PRT
<213> ORGANISM: Artificial Sequence
<220> FEATURE:
<223> OTHER INFORMATION: synthetic

<400> SEQUENCE: 164

Glu Ile Val Met Thr Gln Ser Pro Ala Thr Leu Ser Val Ser Pro Gly
1               5                   10                  15

Lys Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210             215
```

<210> SEQ ID NO 165
<211> LENGTH: 357
<212> TYPE: DNA
<213> ORGANISM: Artificial Sequence
<220> FEATURE:
<223> OTHER INFORMATION: synthetic

<400> SEQUENCE: 165

```
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccct acagtgttgg cacaaacttt    180
gcacagaagt tcagggcag gtcaccatg accagggaca cgtccatcag cacagcctac    240
atggaactga gcaggctgag atctgacgac acggccgtgt attactgtac gagagatggg   300
gcagcagctg gcctctttga ctactggggc cagggaaccc tggtcaccgt ctcctca      357
```

<210> SEQ ID NO 166
<211> LENGTH: 119
<212> TYPE: PRT
<213> ORGANISM: Artificial Sequence
<220> FEATURE:
<223> OTHER INFORMATION: synthetic

<400> SEQUENCE: 166

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Val Gly Thr Asn Phe Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Asp Gly Ala Ala Ala Gly Leu Phe Asp Tyr Trp Gly Gln Gly
            100                 105                 110

Thr Leu Val Thr Val Ser Ser
        115
```

<210> SEQ ID NO 167
<211> LENGTH: 24
<212> TYPE: DNA
<213> ORGANISM: Artificial Sequence
<220> FEATURE:
<223> OTHER INFORMATION: synthetic

<400> SEQUENCE: 167

```
ggatacacct tcaccggcta ctat                                            24
```

```
<210> SEQ ID NO 168
<211> LENGTH: 8
<212> TYPE: PRT
<213> ORGANISM: Artificial Sequence
<220> FEATURE:
<223> OTHER INFORMATION: synthetic

<400> SEQUENCE: 168

Gly Tyr Thr Phe Thr Gly Tyr Tyr
1               5

<210> SEQ ID NO 169
<211> LENGTH: 24
<212> TYPE: DNA
<213> ORGANISM: Artificial Sequence
<220> FEATURE:
<223> OTHER INFORMATION: synthetic

<400> SEQUENCE: 169
atcaacccta acagtgttgg caca                                          24

<210> SEQ ID NO 170
<211> LENGTH: 8
<212> TYPE: PRT
<213> ORGANISM: Artificial Sequence
<220> FEATURE:
<223> OTHER INFORMATION: synthetic

<400> SEQUENCE: 170

Ile Asn Pro Asn Ser Val Gly Thr
1               5

<210> SEQ ID NO 171
<211> LENGTH: 36
<212> TYPE: DNA
<213> ORGANISM: Artificial Sequence
<220> FEATURE:
<223> OTHER INFORMATION: synthetic

<400> SEQUENCE: 171
acgagagatg gggcagcagc tggcctcttt gactac                             36

<210> SEQ ID NO 172
<211> LENGTH: 12
<212> TYPE: PRT
<213> ORGANISM: Artificial Sequence
<220> FEATURE:
<223> OTHER INFORMATION: synthetic

<400> SEQUENCE: 172

Thr Arg Asp Gly Ala Ala Ala Gly Leu Phe Asp Tyr
1               5                   10

<210> SEQ ID NO 173
<211> LENGTH: 321
<212> TYPE: DNA
<213> ORGANISM: Artificial Sequence
<220> FEATURE:
<223> OTHER INFORMATION: synthetic

<400> SEQUENCE: 173
gacatccaga tgacccagtc tccatcctcc ctgtctgcat ctgtaggaga cagagtcacc    60
atcacttgcc gggcgagtca gggcattaac aattatttag cctggtatca gcagaaacca   120
gggaaagttc ctaagctcct gatctatgct gcatccactt tgcaatcagg ggtcccatct   180
cggttcagtg gcagtggatc tgggacagat ttcactctca ccatcagcag cctgcagcct   240
```

```
gaagatgttg caacttatta ctgtcaaaag tttaacagtg ccccgctcac tttcggcgga    300
gggaccaagg tggagatcaa a                                              321
```

<210> SEQ ID NO 174
<211> LENGTH: 107
<212> TYPE: PRT
<213> ORGANISM: Artificial Sequence
<220> FEATURE:
<223> OTHER INFORMATION: synthetic

<400> SEQUENCE: 174

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Phe Asn Ser Ala Pro Leu
                85                  90                  95

Thr Phe Gly Gly Gly Thr Lys Val Glu Ile Lys
            100                 105
```

<210> SEQ ID NO 175
<211> LENGTH: 18
<212> TYPE: DNA
<213> ORGANISM: Artificial Sequence
<220> FEATURE:
<223> OTHER INFORMATION: synthetic

<400> SEQUENCE: 175

```
cagggcatta acaattat                                                  18
```

<210> SEQ ID NO 176
<211> LENGTH: 6
<212> TYPE: PRT
<213> ORGANISM: Artificial Sequence
<220> FEATURE:
<223> OTHER INFORMATION: synthetic

<400> SEQUENCE: 176

```
Gln Gly Ile Asn Asn Tyr
1               5
```

<210> SEQ ID NO 177
<211> LENGTH: 9
<212> TYPE: DNA
<213> ORGANISM: Artificial Sequence
<220> FEATURE:
<223> OTHER INFORMATION: synthetic

<400> SEQUENCE: 177

```
gctgcatcc                                                             9
```

<210> SEQ ID NO 178
<211> LENGTH: 3
<212> TYPE: PRT
<213> ORGANISM: Artificial Sequence
<220> FEATURE:
<223> OTHER INFORMATION: synthetic

<400> SEQUENCE: 178

Ala Ala Ser
1

<210> SEQ ID NO 179
<211> LENGTH: 27
<212> TYPE: DNA
<213> ORGANISM: Artificial Sequence
<220> FEATURE:
<223> OTHER INFORMATION: synthetic

<400> SEQUENCE: 179
caaaagttta acagtgcccc gctcact                                          27

<210> SEQ ID NO 180
<211> LENGTH: 9
<212> TYPE: PRT
<213> ORGANISM: Artificial Sequence
<220> FEATURE:
<223> OTHER INFORMATION: synthetic

<400> SEQUENCE: 180

Gln Lys Phe Asn Ser Ala Pro Leu Thr
1               5

<210> SEQ ID NO 181
<211> LENGTH: 1341
<212> TYPE: DNA
<213> ORGANISM: Artificial Sequence
<220> FEATURE:
<223> OTHER INFORMATION: synthetic

<400> SEQUENCE: 181
caggtgcagc tggtgcagtc tggggctgag gtgaagaagc ctggggcctc agtgaaggtc      60
tcctgcaagg cttctggata caccttcacc ggctactata tgcactgggt gcgacaggcc    120
cctggacaag gcttgagtg gatgggatgg atcaaccta acagtgttgg cacaaacttt      180
gcacagaagt ttcagggcag ggtcaccatg accaggggaca cgtccatcag cacagcctac    240
atggaactga gcaggctgag atctgacgac acggccgtgt attactgtac gagagatggg    300
gcagcagctg gcctctttga ctactgggggc cagggaaccc tggtcaccgt ctcctcagcc    360
tccaccaagg gcccatcggt cttccccctg gcgccctgct ccaggagcac ctccgagagc    420
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac gaagacctac    600
acctgcaacg tagatcacaa gcccagcaac accaaggtgg acaagagagt tgagtccaaa    660
tatggtcccc catgcccacc ctgcccagca cctgagttcc tggggggacc atcagtcttc    720
ctgttccccc caaaacccaa ggacactctc atgatctccc ggacccctga ggtcacgtgc    780
gtggtggtgg acgtgagcca ggaagacccc gaggtccagt tcaactggta cgtggatggc    840
gtggaggtgc ataatgccaa gacaaagccg cgggaggagc agttcaacag cacgtaccgt    900
gtggtcagcg tcctcaccgt cctgcaccag gactggctga acggcaagga gtacaagtgc    960
aaggtctcca acaaaggcct cccgtcctcc atcgagaaaa ccatctccaa agccaaaggg   1020
cagccccgag agccacaggt gtacaccctg cccccatccc aggaggagat gaccaagaac   1080

```
caggtcagcc tgacctgcct ggtcaaaggc ttctacccca gcgacatcgc cgtggagtgg    1140
gagagcaatg ggcagccgga gaacaactac aagaccacgc ctcccgtgct ggactccgac    1200
ggctccttct tcctctacag caggctcacc gtggacaaga gcaggtggca ggaggggaat    1260
gtcttctcat gctccgtgat gcatgaggct ctgcacaacc actacacaca gaagtccctc    1320
tccctgtctc tgggtaaatg a                                              1341
```

<210> SEQ ID NO 182
<211> LENGTH: 446
<212> TYPE: PRT
<213> ORGANISM: Artificial Sequence
<220> FEATURE:
<223> OTHER INFORMATION: synthetic

<400> SEQUENCE: 182

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Val Gly Thr Asn Phe Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Asp Gly Ala Ala Gly Leu Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

Lys Val Ser Asn Lys Gly Leu Pro Ser Ser Ile Glu Lys Thr Ile Ser
              325                 330                 335

Lys Ala Lys Gly Gln Pro Arg Glu Pro Gln Val Tyr Thr Leu Pro Pro
              340                 345                 350

Ser Gln Glu Glu Met Thr Lys Asn Gln Val Ser Leu Thr Cys Leu Val
              355                 360                 365

Lys Gly Phe Tyr Pro Ser Asp Ile Ala Val Glu Trp Glu Ser Asn Gly
              370                 375                 380

Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
              405                 410                 415

Gln Glu Gly Asn Val Phe Ser Cys Ser Val Met His Glu Ala Leu His
              420                 425                 430

Asn His Tyr Thr Gln Lys Ser Leu Ser Leu Ser Leu Gly Lys
              435                 440                 445

<210> SEQ ID NO 183
<211> LENGTH: 645
<212> TYPE: DNA
<213> ORGANISM: Artificial Sequence
<220> FEATURE:
<223> OTHER INFORMATION: synthetic

<400> SEQUENCE: 183
gacatccaga tgacccagtc tccatcctcc ctgtctgcat ctgtaggaga cagagtcacc      60
atcacttgcc gggcgagtca gggcattaac aattatttag cctggtatca gcagaaacca     120
gggaaagttc ctaagctcct gatctatgct gcatccactt tgcaatcagg ggtcccatct     180
cggttcagtg gcagtggatc tgggacagat ttcactctca ccatcagcag cctgcagcct     240
gaagatgttg caacttatta ctgtcaaaag tttaacagtg ccccgctcac tttcggcgga     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645

<210> SEQ ID NO 184
<211> LENGTH: 214
<212> TYPE: PRT
<213> ORGANISM: Artificial Sequence
<220> FEATURE:
<223> OTHER INFORMATION: synthetic

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
              20                  25                  30

Leu Ala Trp Tyr Gln Gln Lys Pro Gly Lys Val Pro Lys Leu Leu Ile
              35                  40                  45

Tyr Ala Ala Ser Thr Leu Gln Ser Gly Val Pro Ser Arg Phe Ser Gly
          50                  55                  60

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Phe Asn Ser Ala Pro Leu
             85                  90                  95

Thr Phe Gly Gly Gly Thr Lys Val Glu Ile Lys Arg Thr Val Ala Ala
         100                 105                 110

Pro Ser Val Phe Ile Phe Pro Pro Ser Asp Glu Gln Leu Lys Ser Gly
     115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
             165                 170                 175

Ser Thr Leu Thr Leu Ser Lys Ala Asp Tyr Glu Lys His Lys Val Tyr
         180                 185                 190

Ala Cys Glu Val Thr His Gln Gly Leu Ser Ser Pro Val Thr Lys Ser
     195                 200                 205

Phe Asn Arg Gly Glu Cys
    210
```

<210> SEQ ID NO 185
<211> LENGTH: 348
<212> TYPE: DNA
<213> ORGANISM: Artificial Sequence
<220> FEATURE:
<223> OTHER INFORMATION: synthetic

<400> SEQUENCE: 185

```
gaggtgcagc tggtggagtc tgggggaggc ttggtacagc ctggggggtc cctgagactc    60
tcctgtgcag cctctggatt cacctttagc acctatgcca tgagctgggt ccgccaggct   120
ccagggaagg gctggagtg gtctcagct attagtggta gtggtggtag tacatactac    180
gcagactccg tgaagggccg gttcaccatc tccagagaca attccaagaa cacgctgtat   240
ctgcaaatga gagcctgag agtcgaggac acggccgtat attactgtgc gaattcccca   300
tcctggttcg accctgggg ccagggaacc ctggtcaccg tctcctca                348
```

<210> SEQ ID NO 186
<211> LENGTH: 116
<212> TYPE: PRT
<213> ORGANISM: Artificial Sequence
<220> FEATURE:
<223> OTHER INFORMATION: synthetic

<400> SEQUENCE: 186

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Val Glu Asp Thr Ala Val Tyr Tyr Cys
             85                  90                  95
```

Ala Asn Ser Pro Ser Trp Phe Asp Pro Trp Gly Gln Gly Thr Leu Val
            100                 105                 110

Thr Val Ser Ser
        115

<210> SEQ ID NO 187
<211> LENGTH: 24
<212> TYPE: DNA
<213> ORGANISM: Artificial Sequence
<220> FEATURE:
<223> OTHER INFORMATION: synthetic

<400> SEQUENCE: 187
ggattcacct ttagcaccta tgcc                                          24

<210> SEQ ID NO 188
<211> LENGTH: 8
<212> TYPE: PRT
<213> ORGANISM: Artificial Sequence
<220> FEATURE:
<223> OTHER INFORMATION: synthetic

<400> SEQUENCE: 188

Gly Phe Thr Phe Ser Thr Tyr Ala
1               5

<210> SEQ ID NO 189
<211> LENGTH: 24
<212> TYPE: DNA
<213> ORGANISM: Artificial Sequence
<220> FEATURE:
<223> OTHER INFORMATION: synthetic

<400> SEQUENCE: 189
attagtggta gtggtggtag taca                                          24

<210> SEQ ID NO 190
<211> LENGTH: 27
<212> TYPE: DNA
<213> ORGANISM: Artificial Sequence
<220> FEATURE:
<223> OTHER INFORMATION: synthetic

<400> SEQUENCE: 190
gcgaattccc catcctggtt cgacccc                                       27

<210> SEQ ID NO 191
<211> LENGTH: 9
<212> TYPE: PRT
<213> ORGANISM: Artificial Sequence
<220> FEATURE:
<223> OTHER INFORMATION: synthetic

<400> SEQUENCE: 191

Ala Asn Ser Pro Ser Trp Phe Asp Pro
1               5

<210> SEQ ID NO 192
<211> LENGTH: 324
<212> TYPE: DNA
<213> ORGANISM: Artificial Sequence
<220> FEATURE:
<223> OTHER INFORMATION: synthetic

<400> SEQUENCE: 192
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

<210> SEQ ID NO 193
<211> LENGTH: 108
<212> TYPE: PRT
<213> ORGANISM: Artificial Sequence
<220> FEATURE:
<223> OTHER INFORMATION: synthetic

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 194
<211> LENGTH: 18
<212> TYPE: DNA
<213> ORGANISM: Artificial Sequence
<220> FEATURE:
<223> OTHER INFORMATION: synthetic

<400> SEQUENCE: 194
cagagcatta gcagctat                                                   18

<210> SEQ ID NO 195
<211> LENGTH: 6
<212> TYPE: PRT
<213> ORGANISM: Artificial Sequence
<220> FEATURE:
<223> OTHER INFORMATION: synthetic

<400> SEQUENCE: 195

Gln Ser Ile Ser Ser Tyr
1               5

<210> SEQ ID NO 196
<211> LENGTH: 30
<212> TYPE: DNA
<213> ORGANISM: Artificial Sequence
<220> FEATURE:
<223> OTHER INFORMATION: synthetic

<400> SEQUENCE: 196
caacagagtt acagtacccc tccgatcacc                                      30

<210> SEQ ID NO 197
<211> LENGTH: 10
<212> TYPE: PRT
<213> ORGANISM: Artificial Sequence
<220> FEATURE:
<223> OTHER INFORMATION: synthetic

<400> SEQUENCE: 197

Gln Gln Ser Tyr Ser Thr Pro Pro Ile Thr
1               5                   10

<210> SEQ ID NO 198
<211> LENGTH: 1332
<212> TYPE: DNA
<213> ORGANISM: Artificial Sequence
<220> FEATURE:
<223> OTHER INFORMATION: synthetic

<400> SEQUENCE: 198

| | | | | | |
|---|---|---|---|---|---|
| gaggtgcagc | tggtggagtc | tgggggaggc | ttggtacagc | ctggggggtc | cctgagactc | 60 |
| tcctgtgcag | cctctggatt | cacctttagc | acctatgcca | tgagctgggt | ccgccaggct | 120 |
| ccagggaagg | ggctggagtg | ggtctcagct | attagtggta | gtggtggtag | tacatactac | 180 |
| gcagactccg | tgaagggccg | gttcaccatc | tccagagaca | attccaagaa | cacgctgtat | 240 |
| ctgcaaatga | agagcctgag | agtcgaggac | acggccgtat | attactgtgc | gaattcccca | 300 |
| tcctggttcg | accccggggg | ccagggaacc | ctggtcaccg | tctcctcagc | ctccaccaag | 360 |
| ggcccatcgg | tcttcccct | ggcgccctgc | tccaggagca | cctccgagag | cacagccgcc | 420 |
| ctgggctgcc | tggtcaagga | ctacttcccc | gaaccggtga | cggtgtcgtg | gaactcaggc | 480 |
| gccctgacca | gcggcgtgca | caccttcccg | gctgtcctac | agtcctcagg | actctactcc | 540 |
| ctcagcagcg | tggtgaccgt | gccctccagc | agcttgggca | cgaagaccta | cacctgcaac | 600 |
| gtagatcaca | agcccagcaa | caccaaggtg | gacaagagag | ttgagtccaa | atatggtccc | 660 |
| ccatgcccac | cctgcccagc | acctgagttc | ctggggggac | catcagtctt | cctgttcccc | 720 |
| ccaaaaccca | aggacactct | catgatctcc | cggacccctg | aggtcacgtg | cgtggtggtg | 780 |
| gacgtgagcc | aggaagaccc | cgaggtccag | ttcaactggt | acgtggatgg | cgtggaggtg | 840 |
| cataatgcca | agacaaagcc | gcgggaggag | cagttcaaca | gcacgtaccg | tgtggtcagc | 900 |
| gtcctcaccg | tcctgcacca | ggactggctg | aacggcaagg | agtacaagtg | caaggtctcc | 960 |
| aacaaaggcc | tcccgtcctc | catcgagaaa | accatctcca | aagccaaagg | gcagccccga | 1020 |
| gagccacagg | tgtacaccct | gcccccatcc | caggaggaga | tgaccaagaa | ccaggtcagc | 1080 |
| ctgacctgcc | tggtcaaagg | cttctacccc | agcgacatcg | ccgtggagtg | ggagagcaat | 1140 |
| gggcagccgg | agaacaacta | caagaccacg | cctcccgtgc | tggactccga | cggctccttc | 1200 |
| ttcctctaca | gcaggctcac | cgtggacaag | agcaggtggc | aggaggggaa | tgtcttctca | 1260 |
| tgctccgtga | tgcatgaggc | tctgcacaac | cactacacac | agaagtccct | ctccctgtct | 1320 |
| ctgggtaaat | ga | | | | | 1332 |

<210> SEQ ID NO 199
<211> LENGTH: 443
<212> TYPE: PRT
<213> ORGANISM: Artificial Sequence
<220> FEATURE:
<223> OTHER INFORMATION: synthetic

<400> SEQUENCE: 199

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Val Glu Asp Thr Ala Val Tyr Tyr Cys
                85                  90                  95

Ala Asn Ser Pro Ser Trp Phe Asp Pro Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415
```

Asn Val Phe Ser Cys Ser Val Met His Glu Ala Leu His Asn His Tyr
        420                 425                 430

Thr Gln Lys Ser Leu Ser Leu Ser Leu Gly Lys
        435                 440

<210> SEQ ID NO 200
<211> LENGTH: 648
<212> TYPE: DNA
<213> ORGANISM: Artificial Sequence
<220> FEATURE:
<223> OTHER INFORMATION: synthetic

<400> SEQUENCE: 200

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttag                  648
```

<210> SEQ ID NO 201
<211> LENGTH: 215
<212> TYPE: PRT
<213> ORGANISM: Artificial Sequence
<220> FEATURE:
<223> OTHER INFORMATION: synthetic

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 202
<211> LENGTH: 357
<212> TYPE: DNA
<213> ORGANISM: Artificial Sequence
<220> FEATURE:
<223> OTHER INFORMATION: synthetic

<400> SEQUENCE: 202
gaagtgcagc tggtggagtc tgggggaggc ttggtacagc ctggcaggtc cctgagactc        60
tcctgtgcag cctctggatt cacctttgat gattatggca tgcactgggt ccgacaagct       120
ccagggaagg gcctggagtg ggtctcagtt attagttgga atagtgctac catagactat       180
gcggactctg tgaagggccg attcaccatc tccagagaca acgccaagaa ttccctgttt       240
ctgcaaatga acagtctgag acctgaggac acggccttgt attactgtgc aaagaaaaat       300
agccttggct ggttctttga ctactggggc cagggaaccc tggtcactgt ctcctca         357

<210> SEQ ID NO 203
<211> LENGTH: 119
<212> TYPE: PRT
<213> ORGANISM: Artificial Sequence
<220> FEATURE:
<223> OTHER INFORMATION: synthetic

<400> SEQUENCE: 203

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Gly Met His Trp Val Arg Gln Ala Pro Gly Lys Gly Leu Glu Trp Val
        35                  40                  45

Ser Val Ile Ser Trp Asn Ser Ala Thr Ile Asp Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Leu Tyr Tyr Cys
            85                  90                  95

Ala Lys Lys Asn Ser Leu Gly Trp Phe Phe Asp Tyr Trp Gly Gln Gly
            100                 105                 110

Thr Leu Val Thr Val Ser Ser
        115

<210> SEQ ID NO 204
<211> LENGTH: 24
<212> TYPE: DNA
<213> ORGANISM: Artificial Sequence
<220> FEATURE:
<223> OTHER INFORMATION: synthetic

<400> SEQUENCE: 204
ggattcacct ttgatgatta tggc                                              24

```
<210> SEQ ID NO 205
<211> LENGTH: 8
<212> TYPE: PRT
<213> ORGANISM: Artificial Sequence
<220> FEATURE:
<223> OTHER INFORMATION: synthetic

<400> SEQUENCE: 205

Gly Phe Thr Phe Asp Asp Tyr Gly
1               5

<210> SEQ ID NO 206
<211> LENGTH: 24
<212> TYPE: DNA
<213> ORGANISM: Artificial Sequence
<220> FEATURE:
<223> OTHER INFORMATION: synthetic

<400> SEQUENCE: 206
attagttgga atagtgctac cata                                             24

<210> SEQ ID NO 207
<211> LENGTH: 8
<212> TYPE: PRT
<213> ORGANISM: Artificial Sequence
<220> FEATURE:
<223> OTHER INFORMATION: synthetic

<400> SEQUENCE: 207

Ile Ser Trp Asn Ser Ala Thr Ile
1               5

<210> SEQ ID NO 208
<211> LENGTH: 36
<212> TYPE: DNA
<213> ORGANISM: Artificial Sequence
<220> FEATURE:
<223> OTHER INFORMATION: synthetic

<400> SEQUENCE: 208
gcaaagaaaa atagccttgg ctggttcttt gactac                                36

<210> SEQ ID NO 209
<211> LENGTH: 12
<212> TYPE: PRT
<213> ORGANISM: Artificial Sequence
<220> FEATURE:
<223> OTHER INFORMATION: synthetic

<400> SEQUENCE: 209

Ala Lys Lys Asn Ser Leu Gly Trp Phe Phe Asp Tyr
1               5                   10

<210> SEQ ID NO 210
<211> LENGTH: 339
<212> TYPE: DNA
<213> ORGANISM: Artificial Sequence
<220> FEATURE:
<223> OTHER INFORMATION: synthetic

<400> SEQUENCE: 210
gacatcgtga tgacccagtc tccagactcc ctggctgtgt ctctgggcga gagggccacc      60
atcaactgca gtccagcca gagtgtttta tacagctcca cgataacaa ctacttagct       120 tggtaccagc agaaaccagg acagcctcct aaactactca tttactgggc atctacccgg    180
```

```
gaatccgggg tccctgaccg attcagtggc agcgggtctg ggacagattt cactctcacc    240
atcagcagcc tgcaggctga agatgtggca gtttattact gtcagcaata ttatagtact    300
cccctcactt tcggcggagg gaccaaggtg gagatcaaa                           339
```

<210> SEQ ID NO 211
<211> LENGTH: 113
<212> TYPE: PRT
<213> ORGANISM: Artificial Sequence
<220> FEATURE:
<223> OTHER INFORMATION: synthetic

<400> SEQUENCE: 211

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asp Asn Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 212
<211> LENGTH: 36
<212> TYPE: DNA
<213> ORGANISM: Artificial Sequence
<220> FEATURE:
<223> OTHER INFORMATION: synthetic

<400> SEQUENCE: 212

```
cagagtgttt tatacagctc caacgataac aactac                              36
```

<210> SEQ ID NO 213
<211> LENGTH: 12
<212> TYPE: PRT
<213> ORGANISM: Artificial Sequence
<220> FEATURE:
<223> OTHER INFORMATION: synthetic

<400> SEQUENCE: 213

Gln Ser Val Leu Tyr Ser Ser Asn Asp Asn Asn Tyr
1               5                   10

<210> SEQ ID NO 214
<211> LENGTH: 9
<212> TYPE: DNA
<213> ORGANISM: Artificial Sequence
<220> FEATURE:
<223> OTHER INFORMATION: synthetic

<400> SEQUENCE: 214

```
tgggcatct                                                            9
```

```
<210> SEQ ID NO 215
<211> LENGTH: 3
<212> TYPE: PRT
<213> ORGANISM: Artificial Sequence
<220> FEATURE:
<223> OTHER INFORMATION: 215

<400> SEQUENCE: 215

Trp Ala Ser
1

<210> SEQ ID NO 216
<211> LENGTH: 27
<212> TYPE: DNA
<213> ORGANISM: Artificial Sequence
<220> FEATURE:
<223> OTHER INFORMATION: synthetic

<400> SEQUENCE: 216
cagcaatatt atagtactcc cctcact                                        27

<210> SEQ ID NO 217
<211> LENGTH: 9
<212> TYPE: PRT
<213> ORGANISM: Artificial Sequence
<220> FEATURE:
<223> OTHER INFORMATION: synthetic

<400> SEQUENCE: 217

Gln Gln Tyr Tyr Ser Thr Pro Leu Thr
1               5

<210> SEQ ID NO 218
<211> LENGTH: 1341
<212> TYPE: DNA
<213> ORGANISM: Artificial Sequence
<220> FEATURE:
<223> OTHER INFORMATION: synthetic

<400> SEQUENCE: 218
gaagtgcagc tggtggagtc tgggggaggc ttggtacagc ctggcaggtc cctgagactc     60
tcctgtgcag cctctggatt caccttttgat gattatggca tgcactgggt ccgacaagct   120
ccagggaagg gcctggagtg ggtctcagtt attagttgga atagtgctac catagactat   180
gcggactctg tgaagggccg attcaccatc tccagagaca cgccaagaa ttccctgttt    240 ctgcaaatga acagtctgag acctgaggac acggccttgt attactgtgc aaagaaaaat   300
agccttggct ggttctttga ctactggggc cagggaaccc tggtcactgt ctcctcagcc   360
tccaccaagg gcccatcggt cttccccctg gcgccctgct ccaggagcac ctccgagagc   420
acagccgccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac gaagacctac   600
acctgcaacg tagatcacaa gcccagcaac accaaggtgg acaagagagt tgagtccaaa   660
tatggtcccc catgcccacc ctgcccagca cctgagttcc tggggggacc atcagtcttc   720
ctgttccccc caaaacccaa ggacactctc atgatctccc ggacccctga ggtcacgtgc   780
gtggtggtgg acgtgagcca ggaagacccc gaggtccagt tcaactggta cgtggatggc   840
gtggaggtgc ataatgccaa gacaaagccg cgggaggagc agttcaacag cacgtaccgt   900
gtggtcagcg tcctcaccgt cctgcaccag gactggctga acggcaagga gtacaagtgc   960
```

-continued

```
aaggtctcca acaaaggcct cccgtcctcc atcgagaaaa ccatctccaa agccaaaggg    1020 cagcccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccgtgct ggactccgac    1200
ggctccttct tcctctacag caggctcacc gtggacaaga gcaggtggca ggaggggaat    1260
gtcttctcat gctccgtgat gcatgaggct ctgcacaacc actacacaca gaagtccctc    1320
tccctgtctc tgggtaaatg a                                              1341
```

<210> SEQ ID NO 219
<211> LENGTH: 446
<212> TYPE: PRT
<213> ORGANISM: Artificial Sequence
<220> FEATURE:
<223> OTHER INFORMATION: synthetic

<400> SEQUENCE: 219

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Gly Met His Trp Val Arg Gln Ala Pro Gly Lys Gly Leu Glu Trp Val
        35                  40                  45

Ser Val Ile Ser Trp Asn Ser Ala Thr Ile Asp Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Leu Tyr Tyr Cys
                85                  90                  95

Ala Lys Lys Asn Ser Leu Gly Trp Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285
```

```
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
        435                 440                 445

<210> SEQ ID NO 220
<211> LENGTH: 663
<212> TYPE: DNA
<213> ORGANISM: Artificial Sequence
<220> FEATURE:
<223> OTHER INFORMATION: synthetic

<400> SEQUENCE: 220
gacatcgtga tgacccagtc tccagactcc ctggctgtgt ctctgggcga gagggccacc      60
atcaactgca agtccagcca gagtgtttta tacagctcca acgataacaa ctacttagct     120
tggtaccagc agaaaccagg acagcctcct aaactactca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cccctcactt tcggcggagg gaccaaggtg gagatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaaagt ctacgcctgc     600
gaagtcaccc atcagggcct gagctcgccc gtcacaaaga gcttcaacag gggagagtgt     660
tag                                                                   663

<210> SEQ ID NO 221
<211> LENGTH: 220
<212> TYPE: PRT
<213> ORGANISM: Artificial Sequence
<220> FEATURE:
<223> OTHER INFORMATION: synthetic

<400> SEQUENCE: 221

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
```

Ser Asn Asp Asn Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 222
<211> LENGTH: 351
<212> TYPE: DNA
<213> ORGANISM: Artificial Sequence
<220> FEATURE:
<223> OTHER INFORMATION: synthetic

<400> SEQUENCE: 222
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaatctat   180
gcacagaagt tccagggcag agtcaccatg accacagaca catccacgag cacagcctac   240
atggagctga ggagcctgag atctgacgac acggccgtgt attactgtgc gagagatata   300
aactggtact cgatctctg ggccgtggc accctggtca ctgtctcctc a             351

<210> SEQ ID NO 223
<211> LENGTH: 117
<212> TYPE: PRT
<213> ORGANISM: Artificial Sequence
<220> FEATURE:
<223> OTHER INFORMATION: synthetic

<400> SEQUENCE: 223

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Ile Tyr Ala Gln Lys Phe
 50                  55                  60

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ile Asn Trp Tyr Phe Asp Leu Trp Gly Arg Gly Thr Leu
            100                 105                 110

Val Thr Val Ser Ser
        115

<210> SEQ ID NO 224
<211> LENGTH: 24
<212> TYPE: DNA
<213> ORGANISM: Artificial Sequence
<220> FEATURE:
<223> OTHER INFORMATION: synthetic

<400> SEQUENCE: 224
ggttacacct ttaccagcta tggt                                          24

<210> SEQ ID NO 225
<211> LENGTH: 8
<212> TYPE: PRT
<213> ORGANISM: Artificial Sequence
<220> FEATURE:
<223> OTHER INFORMATION: synthetic

<400> SEQUENCE: 225

Gly Tyr Thr Phe Thr Ser Tyr Gly
1               5

<210> SEQ ID NO 226
<211> LENGTH: 24
<212> TYPE: DNA
<213> ORGANISM: Artificial Sequence
<220> FEATURE:
<223> OTHER INFORMATION: synthetic

<400> SEQUENCE: 226
atcagcgctt acaatggtaa caca                                          24

<210> SEQ ID NO 227
<211> LENGTH: 8
<212> TYPE: PRT
<213> ORGANISM: Artificial Sequence
<220> FEATURE:
<223> OTHER INFORMATION: synthetic

<400> SEQUENCE: 227

Ile Ser Ala Tyr Asn Gly Asn Thr
1               5

<210> SEQ ID NO 228
<211> LENGTH: 30
<212> TYPE: DNA
<213> ORGANISM: Artificial Sequence
<220> FEATURE:
<223> OTHER INFORMATION: synthetic

<400> SEQUENCE: 228
gcgagagata taaactggta cttcgatctc                                    30

<210> SEQ ID NO 229
<211> LENGTH: 10
<212> TYPE: PRT
<213> ORGANISM: Artificial Sequence
<220> FEATURE:
<223> OTHER INFORMATION: synthetic

<400> SEQUENCE: 229

Ala Arg Asp Ile Asn Trp Tyr Phe Asp Leu
1               5                   10

<210> SEQ ID NO 230
<211> LENGTH: 321
<212> TYPE: DNA
<213> ORGANISM: Artificial Sequence
<220> FEATURE:
<223> OTHER INFORMATION: synthetic

<400> SEQUENCE: 230
gacatccaga tgacccagtc tccatcctcc ctgtctgcat ctgtaggaga cagagtcacc      60
atcacttgcc gggcaagtca gggcattaga aatgatttag gctggtttca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgtggac gttcggccaa     300
gggaccaagg tggaaatcaa a                                               321

<210> SEQ ID NO 231
<211> LENGTH: 107
<212> TYPE: PRT
<213> ORGANISM: Artificial Sequence
<220> FEATURE:
<223> OTHER INFORMATION: synthetic

<400> SEQUENCE: 231

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Phe Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 232
<211> LENGTH: 18
<212> TYPE: DNA
<213> ORGANISM: Artificial Sequence
<220> FEATURE:
<223> OTHER INFORMATION: synthetic

<400> SEQUENCE: 232
cagggcatta gaaatgat                                                    18

<210> SEQ ID NO 233
<211> LENGTH: 6
<212> TYPE: PRT
<213> ORGANISM: Artificial Sequence

```
<220> FEATURE:
<223> OTHER INFORMATION: synthetic

<400> SEQUENCE: 233

Gln Gly Ile Arg Asn Asp
1               5

<210> SEQ ID NO 234
<211> LENGTH: 27
<212> TYPE: DNA
<213> ORGANISM: Artificial Sequence
<220> FEATURE:
<223> OTHER INFORMATION: synthetic

<400> SEQUENCE: 234
ctacagcata atagttaccc gtggacg                                              27

<210> SEQ ID NO 235
<211> LENGTH: 9
<212> TYPE: PRT
<213> ORGANISM: Artificial Sequence
<220> FEATURE:
<223> OTHER INFORMATION: synthetic

<400> SEQUENCE: 235

Leu Gln His Asn Ser Tyr Pro Trp Thr
1               5

<210> SEQ ID NO 236
<211> LENGTH: 1335
<212> TYPE: DNA
<213> ORGANISM: Artificial Sequence
<220> FEATURE:
<223> OTHER INFORMATION: synthetic

<400> SEQUENCE: 236
caggttcagc tggtgcagtc tggagctgag gtgaagaagc ctggggcctc agtgaaggtc        60
tcctgcaagg cttctggtta cacctttacc agctatggta tcagctgggt gcgacaggcc       120
cctggacaag gcttgagtg gatgggatgg atcagcgctt acaatggtaa cacaatctat        180
gcacagaagt tccagggcag agtcaccatg accacagaca catccacgag cacagcctac       240
atggagctga ggagcctgag atctgacgac acggccgtgt attactgtgc gagagatata       300
aactggtact cgatctctg gggccgtggc accctggtca ctgtctcctc agcctccacc        360
aagggcccat cggtcttccc cctggcgccc tgctccagga gcacctccga gagcacagcc       420
gccctgggct gcctggtcaa ggactacttc cccgaaccgg tgacggtgtc gtggaactca       480
ggcgccctga ccagcggcgt gcacaccttc ccggctgtcc tacagtcctc aggactctac       540
tccctcagca gcgtggtgac cgtgccctcc agcagcttgg gcacgaagac ctacacctgc       600
aacgtagatc acaagcccag caacaccaag gtggacaaga gagttgagtc caaatatggt       660
cccccatgcc caccctgccc agcacctgag ttcctggggg gaccatcagt cttcctgttc       720
cccccaaaac ccaaggacac tctcatgatc tcccggaccc ctgaggtcac gtgcgtggtg       780
gtggacgtga gccaggaaga ccccgaggtc cagttcaact ggtacgtgga tggcgtggag       840
gtgcataatg ccaagacaaa gccgcgggag gagcagttca acagcacgta ccgtgtggtc       900
agcgtcctca ccgtcctgca ccaggactgg ctgaacggca aggagtacaa gtgcaaggtc       960
tccaacaaag gcctcccgtc ctccatcgag aaaaccatct ccaaagccaa agggcagccc      1020
cgagagccac aggtgtacac cctgccccca tcccaggagg agatgaccaa gaaccaggtc      1080
```

-continued

```
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct caccgtggac aagagcaggt ggcaggaggg gaatgtcttc    1260
tcatgctccg tgatgcatga ggctctgcac aaccactaca cacagaagtc cctctccctg    1320
tctctgggta aatga                                                     1335
```

<210> SEQ ID NO 237
<211> LENGTH: 444
<212> TYPE: PRT
<213> ORGANISM: Artificial Sequence
<220> FEATURE:
<223> OTHER INFORMATION: synthetic

<400> SEQUENCE: 237

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Ile Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ile Asn Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 238
<211> LENGTH: 645
<212> TYPE: DNA
<213> ORGANISM: Artificial Sequence
<220> FEATURE:
<223> OTHER INFORMATION: synthetic

<400> SEQUENCE: 238
gacatccaga tgacccagtc tccatcctcc ctgtctgcat ctgtaggaga cagagtcacc      60
atcacttgcc gggcaagtca gggcattaga aatgatttag ctggtttca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 239
<211> LENGTH: 214
<212> TYPE: PRT
<213> ORGANISM: Artificial Sequence
<220> FEATURE:
<223> OTHER INFORMATION: synthetic

<400> SEQUENCE: 239

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 240
<211> LENGTH: 357
<212> TYPE: DNA
<213> ORGANISM: Artificial Sequence
<220> FEATURE:
<223> OTHER INFORMATION: synthetic

<400> SEQUENCE: 240

```
gaagtgcagc tggtggagtc tgggggaggc ttggtacagc ctggcaggtc cctgagactc      60
tcctgtgcag cctctggatt cacctttgat gattatggca tgcactgggt ccgacaagct     120
ccagggaagg gcctggagtg ggtctcagtt attagttgga atggtgccac catagactat     180
gcggactctg tgaagggccg attcaccatc tccagagaca acgccaagaa ttccctgttt     240
ctgcaaatga acagtctgag acctgaggac acggccttgt attactgtgc aaagaaaaat     300
agccttggct ggttctttga ctactggggc cagggaaccc tggtcaccgt ctcctca        357
```

<210> SEQ ID NO 241
<211> LENGTH: 119
<212> TYPE: PRT
<213> ORGANISM: Artificial Sequence
<220> FEATURE:
<223> OTHER INFORMATION: synthetic

<400> SEQUENCE: 241

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Gly Met His Trp Val Arg Gln Ala Pro Gly Lys Gly Leu Glu Trp Val
         35                  40                  45

Ser Val Ile Ser Trp Asn Gly Ala Thr Ile Asp Tyr Ala Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Pro Glu Asp Thr Ala Leu Tyr Tyr Cys
                 85                  90                  95
```

Ala Lys Lys Asn Ser Leu Gly Trp Phe Phe Asp Tyr Trp Gly Gln Gly
            100                 105                 110

Thr Leu Val Thr Val Ser Ser
        115

<210> SEQ ID NO 242
<211> LENGTH: 24
<212> TYPE: DNA
<213> ORGANISM: Artificial Sequence
<220> FEATURE:
<223> OTHER INFORMATION: synthetic

<400> SEQUENCE: 242
attagttgga atggtgccac cata                                          24

<210> SEQ ID NO 243
<211> LENGTH: 8
<212> TYPE: PRT
<213> ORGANISM: Artificial Sequence
<220> FEATURE:
<223> OTHER INFORMATION: synthetic

<400> SEQUENCE: 243

Ile Ser Trp Asn Gly Ala Thr Ile
1               5

<210> SEQ ID NO 244
<211> LENGTH: 321
<212> TYPE: DNA
<213> ORGANISM: Artificial Sequence
<220> FEATURE:
<223> OTHER INFORMATION: synthetic

<400> SEQUENCE: 244
gacatccaga tgacccagtc tccatcctcc ctgtctgcat ttgtaggaga cagagtcact     60
atcacttgcc gggcaagtca gggcattaga aatgatttag ctggtatca gcagaaacca    120 gggaaaaccc ctaagcgcct gatctatact gcatccagtt tgcgaagtgg ggtcccatcg   180
aggttcagcg gcagtggatc tgggacagac ttcactctca caatcagcag cctgcagcct   240
gaagattttg caacttatta ctgtctgcag cataataatt acccgtacac ttttggccag   300
gggaccaagc tggagatcaa a                                             321

<210> SEQ ID NO 245
<211> LENGTH: 107
<212> TYPE: PRT
<213> ORGANISM: Artificial Sequence
<220> FEATURE:
<223> OTHER INFORMATION: synthetic

<400> SEQUENCE: 245

Asp Ile Gln Met Thr Gln Ser Pro Ser Ser Leu Ser Ala Phe Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Thr Pro Lys Arg Leu Ile
        35                  40                  45

Tyr Thr Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Asn Tyr Pro Tyr
            85                  90                  95

Thr Phe Gly Gln Gly Thr Lys Leu Glu Ile Lys
        100                 105

<210> SEQ ID NO 246
<211> LENGTH: 9
<212> TYPE: DNA
<213> ORGANISM: Artificial Sequence
<220> FEATURE:
<223> OTHER INFORMATION: synthetic

<400> SEQUENCE: 246 actgcatcc                                                              9

<210> SEQ ID NO 247
<211> LENGTH: 3
<212> TYPE: PRT
<213> ORGANISM: Artificial Sequence
<220> FEATURE:
<223> OTHER INFORMATION: synthetic

<400> SEQUENCE: 247

Thr Ala Ser
1

<210> SEQ ID NO 248
<211> LENGTH: 27
<212> TYPE: DNA
<213> ORGANISM: Artificial Sequence
<220> FEATURE:
<223> OTHER INFORMATION: synthetic

<400> SEQUENCE: 248
ctgcagcata ataattaccc gtacact                                          27

<210> SEQ ID NO 249
<211> LENGTH: 9
<212> TYPE: PRT
<213> ORGANISM: Artificial Sequence
<220> FEATURE:
<223> OTHER INFORMATION: synthetic

<400> SEQUENCE: 249

Leu Gln His Asn Asn Tyr Pro Tyr Thr
1               5

<210> SEQ ID NO 250
<211> LENGTH: 1341
<212> TYPE: DNA
<213> ORGANISM: Artificial Sequence
<220> FEATURE:
<223> OTHER INFORMATION: synthetic

<400> SEQUENCE: 250
gaagtgcagc tggtggagtc tgggggaggc ttggtacagc ctggcaggtc cctgagactc      60
tcctgtgcag cctctggatt cacctttgat gattatggca tgcactgggt ccgacaagct     120
ccagggaagg gcctggagtg ggtctcagtt attagttgga atggtggcac catagactat     180
gcggactctg tgaagggccg attcaccatc tccagagaca cgccaagaa ttccctgttt      240 ctgcaaatga acagtctgag acctgaggac acggccttgt attactgtgc aaagaaaaat     300
agccttggct ggttctttga ctactggggc cagggaaccc tggtcaccgt ctcctcagcc     360
tccaccaagg gcccatcggt cttccccctg gcgccctgct ccaggagcac ctccgagagc     420

```
acagccgccc tgggctgcct ggtcaaggac tacttcccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac gaagacctac    600
acctgcaacg tagatcacaa gcccagcaac accaaggtgg acaagagagt tgagtccaaa    660
tatggtcccc catgcccacc ctgcccagca cctgagttcc tggggggacc atcagtcttc    720
ctgttccccc caaaacccaa ggacactctc atgatctccc ggaccccctga ggtcacgtgc    780 gtggtggtgg acgtgagcca ggaagacccc gaggtccagt tcaactggta cgtggatggc    840
gtggaggtgc ataatgccaa gacaaagccg cgggaggagc agttcaacag cacgtaccgt    900
gtggtcagcg tcctcaccgt cctgcaccag gactggctga acggcaagga gtacaagtgc    960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc tcccgtgct ggactccgac    1200 ggctccttct tcctctacag caggctcacc gtggacaaga gcaggtggca ggaggggaat    1260
gtcttctcat gctccgtgat gcatgaggct ctgcacaacc actacacaca gaagtccctc    1320
tccctgtctc tgggtaaatg a                                              1341
```

<210> SEQ ID NO 251
<211> LENGTH: 446
<212> TYPE: PRT
<213> ORGANISM: Artificial Sequence
<220> FEATURE:
<223> OTHER INFORMATION: synthetic

<400> SEQUENCE: 251

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Gly Met His Trp Val Arg Gln Ala Pro Gly Lys Gly Leu Glu Trp Val
        35                  40                  45

Ser Val Ile Ser Trp Asn Gly Ala Thr Ile Asp Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Leu Tyr Tyr Cys
                85                  90                  95

Ala Lys Lys Asn Ser Leu Gly Trp Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 252
<211> LENGTH: 645
<212> TYPE: DNA
<213> ORGANISM: Artificial Sequence
<220> FEATURE:
<223> OTHER INFORMATION: synthetic

<400> SEQUENCE: 252

```
gacatccaga tgacccagtc tccatcctcc ctgtctgcat ttgtaggaga cagagtcact    60
atcacttgcc gggcaagtca gggcattaga aatgatttag ctggtatca  gcagaaacca   120 gggaaaaccc ctaagcgcct gatctatact gcatccagtt tgcgaagtgg ggtcccatcg   180
aggttcagcg gcagtggatc tgggacagac ttcactctca caatcagcag cctgcagcct   240
gaagattttg caacttatta ctgtctgcag cataataatt acccgtacac ttttggccag   300
gggaccaagc tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg ataacgccc  tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 253
<211> LENGTH: 214
<212> TYPE: PRT
<213> ORGANISM: Artificial Sequence
<220> FEATURE:
<223> OTHER INFORMATION: synthetic

<400> SEQUENCE: 253

```
Asp Ile Gln Met Thr Gln Ser Pro Ser Ser Leu Ser Ala Phe Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Thr Pro Lys Arg Leu Ile
        35                  40                  45

Tyr Thr Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 254
<211> LENGTH: 366
<212> TYPE: DNA
<213> ORGANISM: Artificial Sequence
<220> FEATURE:
<223> OTHER INFORMATION: synthetic

<400> SEQUENCE: 254

| | | | | | |
|---|---|---|---|---|---|
| gaggtgcagc | tggtggagtc | tgggggaaac | ttggtacagc | cggggggggtc | cctgagactc | 60 |
| tcctgtgcag | cctctggatt | cacctttagc | aattatgcca | tgagttgggt | ccgccaggct | 120 |
| ccagggaagg | ggctggagtg | ggtctcaggt | atcactggta | atggtgttaa | cacatattat | 180 |
| tcagtctccg | tgaagggccg | gttcaccatc | tccagagaca | attccaagaa | cacgctgttt | 240 |
| ctggaaatga | acagcctgag | agccgaggac | acggccatat | attactgtgt | gaaagaaagg | 300 |
| ggccacagct | ggttcgggga | ctggttcgac | ccctgggggcc | aggaaccct | ggtcaccgtc | 360 |
| tcctca | | | | | | 366 |

<210> SEQ ID NO 255
<211> LENGTH: 122
<212> TYPE: PRT

<213> ORGANISM: Artificial Sequence
<220> FEATURE:
<223> OTHER INFORMATION: synthetic

<400> SEQUENCE: 255

```
Glu Val Gln Leu Val Glu Ser Gly Gly Asn Leu Val Gln Pro Gly Gly
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
Ser Gly Ile Thr Gly Asn Gly Val Asn Thr Tyr Tyr Ser Val Ser Val
    50                  55                  60
Lys Gly Arg Phe Thr Ile Ser Arg Asp Asn Ser Lys Asn Thr Leu Phe
65                  70                  75                  80
Leu Glu Met Asn Ser Leu Arg Ala Glu Asp Thr Ala Ile Tyr Tyr Cys
                85                  90                  95
Val Lys Glu Arg Gly His Ser Trp Phe Gly Asp Trp Phe Asp Pro Trp
            100                 105                 110
Gly Gln Gly Thr Leu Val Thr Val Ser Ser
        115                 120
```

<210> SEQ ID NO 256
<211> LENGTH: 24
<212> TYPE: DNA
<213> ORGANISM: Artificial Sequence
<220> FEATURE:
<223> OTHER INFORMATION: synthetic

<400> SEQUENCE: 256
ggattcacct ttagcaatta tgcc                                    24

<210> SEQ ID NO 257
<211> LENGTH: 8
<212> TYPE: PRT
<213> ORGANISM: Artificial Sequence
<220> FEATURE:
<223> OTHER INFORMATION: synthetic

<400> SEQUENCE: 257

```
Gly Phe Thr Phe Ser Asn Tyr Ala
1               5
```

<210> SEQ ID NO 258
<211> LENGTH: 24
<212> TYPE: DNA
<213> ORGANISM: Artificial Sequence
<220> FEATURE:
<223> OTHER INFORMATION: synthetic

<400> SEQUENCE: 258
atcactggta atggtgttaa caca                                    24

<210> SEQ ID NO 259
<211> LENGTH: 8
<212> TYPE: PRT
<213> ORGANISM: Artificial Sequence
<220> FEATURE:
<223> OTHER INFORMATION: synthetic

<400> SEQUENCE: 259

```
Ile Thr Gly Asn Gly Val Asn Thr
1               5
```

<210> SEQ ID NO 260
<211> LENGTH: 45
<212> TYPE: DNA
<213> ORGANISM: Artificial Sequence
<220> FEATURE:
<223> OTHER INFORMATION: synthetic

<400> SEQUENCE: 260
gtgaaagaaa ggggccacag ctggttcggg gactggttcg acccc          45

<210> SEQ ID NO 261
<211> LENGTH: 15
<212> TYPE: PRT
<213> ORGANISM: Artificial Sequence
<220> FEATURE:
<223> OTHER INFORMATION: synthetic

<400> SEQUENCE: 261

Val Lys Glu Arg Gly His Ser Trp Phe Gly Asp Trp Phe Asp Pro
1               5                   10                  15

<210> SEQ ID NO 262
<211> LENGTH: 321
<212> TYPE: DNA
<213> ORGANISM: Artificial Sequence
<220> FEATURE:
<223> OTHER INFORMATION: synthetic

<400> SEQUENCE: 262
gacatccaga tgacccagtc tccatcctcc ctgtctgcat ctgtaggaga cagagtcacc      60
atcacttgtc ggtcaagtca gagtgttatc agctatctaa attggtatca gcagaaacca    120
ggaaaagccc ctaaactcct gatatttggt gcatccagtt taataagtgg ggtcccatca    180
aggttcagtg gcagtggatc tgggacagat tcactctcac ccatcgtcag tctgcagcct    240
gaagatttcg cagtttactt ctgtcaacag aattaccttc ccccgctcac tttcggcgga    300
gggaccaagg tggagatcaa a                                               321

<210> SEQ ID NO 263
<211> LENGTH: 107
<212> TYPE: PRT
<213> ORGANISM: Artificial Sequence
<220> FEATURE:
<223> OTHER INFORMATION: synthetic

<400> SEQUENCE: 263

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Ile Ser Tyr
            20                  25                  30

Leu Asn Trp Tyr Gln Gln Lys Pro Gly Lys Ala Pro Lys Leu Leu Ile
        35                  40                  45

Phe Gly Ala Ser Ser Leu Ile Ser Gly Val Pro Ser Arg Phe Ser Gly
    50                  55                  60

Ser Gly Ser Gly Thr Asp Phe Thr Leu Thr Ile Val Ser Leu Gln Pro
65                  70                  75                  80

Glu Asp Phe Ala Val Tyr Phe Cys Gln Gln Asn Tyr Leu Pro Pro Leu
                85                  90                  95

Thr Phe Gly Gly Gly Thr Lys Val Glu Ile Lys
            100                 105

<210> SEQ ID NO 264
<211> LENGTH: 18
<212> TYPE: DNA
<213> ORGANISM: Artificial Sequence
<220> FEATURE:
<223> OTHER INFORMATION: synthetic

<400> SEQUENCE: 264
cagagtgtta tcagctat               18

<210> SEQ ID NO 265
<211> LENGTH: 6
<212> TYPE: PRT
<213> ORGANISM: Artificial Sequence
<220> FEATURE:
<223> OTHER INFORMATION: synthetic

<400> SEQUENCE: 265

Gln Ser Val Ile Ser Tyr
1               5

<210> SEQ ID NO 266
<211> LENGTH: 27
<212> TYPE: DNA
<213> ORGANISM: Artificial Sequence
<220> FEATURE:
<223> OTHER INFORMATION: synthetic

<400> SEQUENCE: 266
caacagaatt accttccccc gctcact               27

<210> SEQ ID NO 267
<211> LENGTH: 9
<212> TYPE: PRT
<213> ORGANISM: Artificial Sequence
<220> FEATURE:
<223> OTHER INFORMATION: synthetic

<400> SEQUENCE: 267

Gln Gln Asn Tyr Leu Pro Pro Leu Thr
1               5

<210> SEQ ID NO 268
<211> LENGTH: 1350
<212> TYPE: DNA
<213> ORGANISM: Artificial Sequence
<220> FEATURE:
<223> OTHER INFORMATION: synthetic

<400> SEQUENCE: 268
gaggtgcagc tggtggagtc tgggggaaac ttggtacagc cggggggttc cctgagactc      60
tcctgtgcag cctctggatt cacctttagc aattatgcca tgagttgggt ccgccaggct     120
ccagggaagg ggctggagtg ggtctcaggt atcactggta atggtgttaa cacatattat     180
tcagtctccg tgaagggccg gttcaccatc tccagagaca attccaagaa cacgctgttt     240
ctggaaatga acagcctgag agccgaggac acggccatat attactgtgt gaaagaaagg     300
ggccacagct ggttcgggga ctggttcgac cctgggggcc agggaacccct ggtcaccgtc     360 tcctcagcct ccaccaaggg cccatcggtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600

-continued

```
aagacctaca cctgcaacgt agatcacaag cccagcaaca ccaaggtgga caagagagtt    660
gagtccaaat atggtccccc atgcccaccc tgcccagcac ctgagttcct ggggggacca    720
tcagtcttcc tgttcccccc aaaacccaag gacactctca tgatctcccg gaccctgag    780
gtcacgtgcg tggtggtgga cgtgagccag gaagacccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc   1140
gtggagtggg agagcaatgg gcagccggag aacaactaca agaccacgcc tcccgtgctg   1200
gactccgacg gctccttctt cctctacagc aggctcaccg tggacaagag caggtggcag   1260
gaggggaatg tcttctcatg ctccgtgatg catgaggctc tgcacaacca ctacacacag   1320
aagtccctct ccctgtctct gggtaaatga                                    1350
```

<210> SEQ ID NO 269
<211> LENGTH: 449
<212> TYPE: PRT
<213> ORGANISM: Artificial Sequence
<220> FEATURE:
<223> OTHER INFORMATION: synthetic

<400> SEQUENCE: 269

```
Glu Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Thr Gly Asn Gly Val Asn Thr Tyr Tyr Ser Val Ser Val
    50                  55                  60

Lys Gly Arg Phe Thr Ile Ser Arg Asp Asn Ser Lys Asn Thr Leu Phe
65                  70                  75                  80

Leu Glu Met Asn Ser Leu Arg Ala Glu Asp Thr Ala Ile Tyr Tyr Cys
                85                  90                  95

Val Lys Glu Arg Gly His Ser Trp Phe Gly Asp Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220
```

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 270
<211> LENGTH: 645
<212> TYPE: DNA
<213> ORGANISM: Artificial Sequence
<220> FEATURE:
<223> OTHER INFORMATION: synthetic

<400> SEQUENCE: 270
gacatccaga tgacccagtc tccatcctcc ctgtctgcat ctgtaggaga cagagtcacc    60
atcacttgtc ggtcaagtca gagtgttatc agctatctaa attggtatca gcagaaacca   120
ggaaaagccc ctaaactcct gatatttggt gcatccagtt taataagtgg ggtcccatca   180
aggttcagtg gcagtggatc tgggacagat ttcactctca ccatcgtcag tctgcagcct   240
gaagatttcg cagtttactt ctgtcaacag aattaccttc cccgctcac tttcggcgga   300 gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                  645

<210> SEQ ID NO 271
<211> LENGTH: 214

<212> TYPE: PRT
<213> ORGANISM: Artificial Sequence
<220> FEATURE:
<223> OTHER INFORMATION: synthetic

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Ile Ser Tyr
            20                  25                  30

Leu Asn Trp Tyr Gln Gln Lys Pro Gly Lys Ala Pro Lys Leu Leu Ile
        35                  40                  45

Phe Gly Ala Ser Ser Leu Ile Ser Gly Val Pro Ser Arg Phe Ser Gly
    50                  55                  60

Ser Gly Ser Gly Thr Asp Phe Thr Leu Thr Ile Val Ser Leu Gln Pro
65                  70                  75                  80

Glu Asp Phe Ala Val Tyr Phe Cys Gln Gln Asn Tyr Leu Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 272
<211> LENGTH: 366
<212> TYPE: DNA
<213> ORGANISM: Artificial Sequence
<220> FEATURE:
<223> OTHER INFORMATION: synthetic

<400> SEQUENCE: 272
gaggtgcagc tggtggagtc tgggggaaac ttggtacagc cggggggtc cctgagactc      60 tcctgtgcag cctctggatt cacctttagc aattatgcca tgagttgggt ccgccaggct    120
ccagggaagg gctggagtg gtctcaggt atcactggta atggtattaa aacctactac      180
tcagtctccg cgaagggccg gttcaccatc tccagagaca attccaagaa cacgctgttt    240
ctgcaaatga acagcctgag agccgaggac acggccatat attactgtgt gaaagaaagg    300
ggccacagct ggttcgggga ctggttcgac ccctggggcc agggaaccct ggtcaccgtc    360
tcctca                                                                366

<210> SEQ ID NO 273
<211> LENGTH: 122
<212> TYPE: PRT
<213> ORGANISM: Artificial Sequence
<220> FEATURE:
<223> OTHER INFORMATION: synthetic

<400> SEQUENCE: 273

Glu Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Thr Gly Asn Gly Ile Lys Thr Tyr Tyr Ser Val Ser Ala
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Ile Tyr Tyr Cys
                85                  90                  95

Val Lys Glu Arg Gly His Ser Trp Phe Gly Asp Trp Phe Asp Pro Trp
            100                 105                 110

Gly Gln Gly Thr Leu Val Thr Val Ser Ser
        115                 120

<210> SEQ ID NO 274
<211> LENGTH: 24
<212> TYPE: DNA
<213> ORGANISM: Artificial Sequence
<220> FEATURE:
<223> OTHER INFORMATION: synthetic

<400> SEQUENCE: 274
atcactggta atggtattaa aacc                                          24

<210> SEQ ID NO 275
<211> LENGTH: 8
<212> TYPE: PRT
<213> ORGANISM: Artificial Sequence
<220> FEATURE:
<223> OTHER INFORMATION: synthetic

<400> SEQUENCE: 275

Ile Thr Gly Asn Gly Ile Lys Thr
1               5

<210> SEQ ID NO 276
<211> LENGTH: 336
<212> TYPE: DNA
<213> ORGANISM: Artificial Sequence
<220> FEATURE:
<223> OTHER INFORMATION: synthetic

<400> SEQUENCE: 276
gatattgtga tgacccagac tccactctct tcacctgtca cccttggaca gccggcctcc     60
atctcctgca ggtctagtca aggcctcgta aacagtgatg gaaacaccta tttgagttgg    120
cttcaccaga ggccaggcca gcctccaaga ctcctaattt atgagatttc taaccgtttc    180
tctggagtcc cagacagatt cagtggcagt ggggctggga cagatttcac actgaaaatc    240
agtagggtgg aagctgagga tgtcggattt tattactgta tgcaatctac acaatttcct    300
ctcactttcg gcggagggac caaggtggag atcaaa                             336

<210> SEQ ID NO 277
<211> LENGTH: 112

```
<212> TYPE: PRT
<213> ORGANISM: Artificial Sequence
<220> FEATURE:
<223> OTHER INFORMATION: synthetic

<400> SEQUENCE: 277

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Gly Leu Val Asn Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Glu Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Phe Tyr Tyr Cys Met Gln Ser
                85                  90                  95

Thr Gln Phe Pro Leu Thr Phe Gly Gly Thr Lys Val Glu Ile Lys
            100                 105                 110

<210> SEQ ID NO 278
<211> LENGTH: 33
<212> TYPE: DNA
<213> ORGANISM: Artificial Sequence
<220> FEATURE:
<223> OTHER INFORMATION: synthetic

<400> SEQUENCE: 278
caaggcctcg taaacagtga tggaaacacc tat                         33

<210> SEQ ID NO 279
<211> LENGTH: 11
<212> TYPE: PRT
<213> ORGANISM: Artificial Sequence
<220> FEATURE:
<223> OTHER INFORMATION: synthetic

<400> SEQUENCE: 279

Gln Gly Leu Val Asn Ser Asp Gly Asn Thr Tyr
1               5                   10

<210> SEQ ID NO 280
<211> LENGTH: 9
<212> TYPE: DNA
<213> ORGANISM: Artificial Sequence
<220> FEATURE:
<223> OTHER INFORMATION: synthetic

<400> SEQUENCE: 280 gagatttct                                                    9

<210> SEQ ID NO 281
<211> LENGTH: 3
<212> TYPE: PRT
<213> ORGANISM: Artificial Sequence
<220> FEATURE:
<223> OTHER INFORMATION: synthetic

<400> SEQUENCE: 281

Glu Ile Ser
1
```

<210> SEQ ID NO 282
<211> LENGTH: 27
<212> TYPE: DNA
<213> ORGANISM: Artificial Sequence
<220> FEATURE:
<223> OTHER INFORMATION: synthetic

<400> SEQUENCE: 282
atgcaatcta cacaatttcc tctcact                                27

<210> SEQ ID NO 283
<211> LENGTH: 9
<212> TYPE: PRT
<213> ORGANISM: Artificial Sequence
<220> FEATURE:
<223> OTHER INFORMATION: synthetic

<400> SEQUENCE: 283

Met Gln Ser Thr Gln Phe Pro Leu Thr
1               5

<210> SEQ ID NO 284
<211> LENGTH: 1350
<212> TYPE: DNA
<213> ORGANISM: Artificial Sequence
<220> FEATURE:
<223> OTHER INFORMATION: synthetic

<400> SEQUENCE: 284

| | |
|---|---|
| gaggtgcagc tggtggagtc tgggggaaac ttggtacagc cggggggtc cctgagactc | 60 |
| tcctgtgcag cctctggatt caccttagc aattatgcca tgagttgggt ccgccaggct | 120 |
| ccagggaagg gctggagtg gtctcaggt atcactggta atggtattaa aacctactac | 180 |
| tcagtctccg cgaagggccg gttcaccatc tccagagaca attccaagaa cacgctgttt | 240 |
| ctgcaaatga acagcctgag agccgaggac acggccatat attactgtgt gaaagaaagg | 300 |
| ggccacagct ggttcgggga ctggttcgac cctgggggcc aggaaccct ggtcaccgtc | 360 |
| tcctcagcct ccaccaaggg cccatcggtc ttcccctgg cgccctgctc caggagcacc | 420 |
| tccgagagca cagccgccct gggctgcctg gtcaaggact acttcccga accggtgacg | 480 |
| gtgtcgtgga actcaggcgc cctgaccagc ggcgtgcaca ccttcccggc tgtcctacag | 540 |
| tcctcaggac tctactccct cagcagcgtg gtgaccgtgc cctccagcag cttgggcacg | 600 |
| aagacctaca cctgcaacgt agatcacaag cccagcaaca ccaaggtgga caagagagtt | 660 |
| gagtccaaat atggtccccc atgcccaccc tgcccagcac ctgagttcct ggggggacca | 720 |
| tcagtcttcc tgttcccccc aaaacccaag gacactctca tgatctcccg gacccctgag | 780 |
| gtcacgtgcg tggtggtgga cgtgagccag gaagaccccg aggtccagtt caactggtac | 840 |
| gtggatggcg tggaggtgca taatgccaag acaaagccgc gggaggagca gttcaacagc | 900 |
| acgtaccgtg tggtcagcgt cctcaccgtc ctgcaccagg actggctgaa cggcaaggag | 960 |
| tacaagtgca aggtctccaa caaaggcctc ccgtcctcca tcgagaaaac catctccaaa | 1020 |
| gccaaagggc agccccgaga gccacaggtg tacaccctgc cccatcccag gaggagatg | 1080 |
| accaagaacc aggtcagcct gacctgcctg gtcaaaggct tctacccag cgacatcgcc | 1140 |
| gtggagtggg agagcaatgg gcagccggag aacaactaca gaccacgcc tcccgtgctg | 1200 |
| gactccgacg gctccttctt cctctacagc aggctcaccg tggacaagag caggtggcag | 1260 |
| gagggggaatg tcttctcatg ctccgtgatg catgaggctc tgcacaacca ctacacacag | 1320 |
| aagtccctct ccctgtctct gggtaaatga | 1350 |

<210> SEQ ID NO 285
<211> LENGTH: 449
<212> TYPE: PRT
<213> ORGANISM: Artificial Sequence
<220> FEATURE:
<223> OTHER INFORMATION: synthetic

<400> SEQUENCE: 285

```
Glu Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Thr Gly Asn Gly Ile Lys Thr Tyr Tyr Ser Val Ser Ala
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Ile Tyr Tyr Cys
                85                  90                  95

Val Lys Glu Arg Gly His Ser Trp Phe Gly Asp Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 286
<211> LENGTH: 660
<212> TYPE: DNA
<213> ORGANISM: Artificial Sequence
<220> FEATURE:
<223> OTHER INFORMATION: synthetic

<400> SEQUENCE: 286
gatattgtga tgacccagac tccactctct tcacctgtca cccttggaca gccggcctcc    60
atctcctgca ggtctagtca aggcctcgta acagtgatg gaaacaccta tttgagttgg   120
cttcaccaga ggccaggcca gcctccaaga ctcctaattt atgagatttc taaccgtttc   180
tctggagtcc cagacagatt cagtggcagt ggggctggga cagatttcac actgaaaatc   240
agtagggtgg aagctgagga tgtcggattt tattactgta tgcaatctac acaatttcct   300 ctcacttttcg gcggagggac caaggtggag atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

<210> SEQ ID NO 287
<211> LENGTH: 219
<212> TYPE: PRT
<213> ORGANISM: Artificial Sequence
<220> FEATURE:
<223> OTHER INFORMATION: synthetic

<400> SEQUENCE: 287

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Gly Leu Val Asn Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Glu Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Phe Tyr Tyr Cys Met Gln Ser
                85                  90                  95

Thr Gln Phe Pro Leu Thr Phe Gly Gly Gly Thr Lys Val Glu Ile Lys
            100                 105                 110
```

```
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 288
<211> LENGTH: 366
<212> TYPE: DNA
<213> ORGANISM: Artificial Sequence
<220> FEATURE:
<223> OTHER INFORMATION: synthetic

<400> SEQUENCE: 288

```
gaggtgcagc tggtggagtc tgggggaaac ttggtacagc cggggggtc cctgagactc      60 tcctgtgcag cctctggatt cacctttagc aattatgcca tgagttgggt ccgccaggct     120
ccagggaagg gactggagtg gtctcaggt atcactggca atggtattaa tacatattac     180
tcagtctccg tgaagggccg cttcaccatc tccagagaca attccaagaa cacggtgttt     240
ctacaaatga acagcctgag agccgaggac acggccatat attactgtgt gaaagaaagg     300
ggccacagct ggttcgggga ctggttcgac ccctggggcc agggaaccct ggtcaccgtc     360
tcctca                                                                366
```

<210> SEQ ID NO 289
<211> LENGTH: 122
<212> TYPE: PRT
<213> ORGANISM: Artificial Sequence
<220> FEATURE:
<223> OTHER INFORMATION: synthetic

<400> SEQUENCE: 289

```
Glu Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Thr Gly Asn Gly Ile Asn Thr Tyr Tyr Ser Val Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Ala Glu Asp Thr Ala Ile Tyr Tyr Cys
                85                  90                  95

Val Lys Glu Arg Gly His Ser Trp Phe Gly Asp Trp Phe Asp Pro Trp
            100                 105                 110

Gly Gln Gly Thr Leu Val Thr Val Ser Ser
        115                 120
```

```
<210> SEQ ID NO 290
<211> LENGTH: 24
<212> TYPE: DNA
<213> ORGANISM: Artificial Sequence
<220> FEATURE:
<223> OTHER INFORMATION: synthetic

<400> SEQUENCE: 290
atcactggca atggtattaa taca                                              24

<210> SEQ ID NO 291
<211> LENGTH: 8
<212> TYPE: PRT
<213> ORGANISM: Artificial Sequence
<220> FEATURE:
<223> OTHER INFORMATION: synthetic

<400> SEQUENCE: 291

Ile Thr Gly Asn Gly Ile Asn Thr
1               5

<210> SEQ ID NO 292
<211> LENGTH: 321
<212> TYPE: DNA
<213> ORGANISM: Artificial Sequence
<220> FEATURE:
<223> OTHER INFORMATION: synthetic

<400> SEQUENCE: 292
gacatccaga tgacccagtc tccatcctcc ctgtctgcat ctgtaggaga cagagtcacc        60
atcacttgcc gggcaagtca gggcattaga aatgatttag gctggtatca gcagaaacca      120
gggaaagccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatagtt acccgtggac tttcggccaa      300
gggaccaagg tggaaatcaa a                                                321

<210> SEQ ID NO 293
<211> LENGTH: 107
<212> TYPE: PRT
<213> ORGANISM: Artificial Sequence
<220> FEATURE:
<223> OTHER INFORMATION: synthetic

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 294
<211> LENGTH: 27
```

```
<212> TYPE: DNA
<213> ORGANISM: Artificial Sequence
<220> FEATURE:
<223> OTHER INFORMATION: synthetic

<400> SEQUENCE: 294
ctacagcata atagttaccc gtggact                                            27

<210> SEQ ID NO 295
<211> LENGTH: 1350
<212> TYPE: DNA
<213> ORGANISM: Artificial Sequence
<220> FEATURE:
<223> OTHER INFORMATION: synthetic

<400> SEQUENCE: 295
gaggtgcagc tggtggagtc tgggggaaac ttggtacagc cggggggggtc cctgagactc          60 tcctgtgcag cctctggatt cacctttagc aattatgcca tgagttgggt ccgccaggct         120
ccagggaagg gactggagtg gtctcaggt atcactggca atggtattaa tacatattac          180
tcagtctccg tgaagggccg cttcaccatc tccagagaca attccaagaa cacggtgttt         240
ctacaaatga acagcctgag agccgaggac acggccatat attactgtgt gaaagaaagg         300
ggccacagct ggttcgggga ctggttcgac ccctggggcc agggaaccct ggtcaccgtc         360
tcctcagcct ccaccaaggg cccatcggtc ttcccctgg cgccctgctc caggagcacc          420
tccgagagca cagccgccct gggctgcctg gtcaaggact acttccccga accggtgacg         480
gtgtcgtgga actcaggcgc cctgaccagc ggcgtgcaca ccttcccggc tgtcctacag         540
tcctcaggac tctactccct cagcagcgtg gtgaccgtgc cctccagcag cttgggcacg         600
aagacctaca cctgcaacgt agatcacaag cccagcaaca ccaaggtgga caagagagtt         660
gagtccaaat atggtccccc atgcccaccc tgcccagcac ctgagttcct ggggggacca         720
tcagtcttcc tgttcccccc aaaacccaag gacactctca tgatctcccg gacccctgag         780
gtcacgtgcg tggtggtgga cgtgagccag gaagacccg aggtccagtt caactggtac          840
gtggatggcg tggaggtgca taatgccaag acaaagccgc gggaggagca gttcaacagc         900
acgtaccgtg tggtcagcgt cctcaccgtc ctgcaccagg actggctgaa cggcaaggag         960
tacaagtgca aggtctccaa caaaggcctc ccgtcctcca tcgagaaaac catctccaaa        1020
gccaaagggc agccccgaga gccacaggtg tacaccctgc ccccatccca ggaggagatg        1080
accaagaacc aggtcagcct gacctgcctg gtcaaaggct tctaccccag cgacatcgcc        1140
gtggagtggg agagcaatgg gcagccggag aacaactaca agaccacgcc tcccgtgctg        1200
gactccgacg gctccttctt cctctacagc aggctcaccg tggacaagag caggtggcag        1260 gagggggaatg tcttctcatg ctccgtgatg catgaggctc tgcacaacca ctacacacag        1320
aagtccctct ccctgtctct gggtaaatga                                         1350

<210> SEQ ID NO 296
<211> LENGTH: 449
<212> TYPE: PRT
<213> ORGANISM: Artificial Sequence
<220> FEATURE:
<223> OTHER INFORMATION: synthetic

<400> SEQUENCE: 296

Glu Val Gln Leu Val Glu Ser Gly Gly Asn Leu Val Gln Pro Gly Gly
 1               5                  10                  15
```

```
Ser Leu Arg Leu Ser Cys Ala Ala Ser Gly Phe Thr Phe Ser Asn Tyr
         20                  25                  30

Ala Met Ser Trp Val Arg Gln Ala Pro Gly Lys Gly Leu Glu Trp Val
         35                  40                  45

Ser Gly Ile Thr Gly Asn Gly Ile Asn Thr Tyr Tyr Ser Val Ser Val
         50                  55                  60

Lys Gly Arg Phe Thr Ile Ser Arg Asp Asn Ser Lys Asn Thr Val Phe
 65                  70                  75                  80

Leu Gln Met Asn Ser Leu Arg Ala Glu Asp Thr Ala Ile Tyr Tyr Cys
                 85                  90                  95

Val Lys Glu Arg Gly His Ser Trp Phe Gly Asp Trp Phe Asp Pro Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430
```

Ala Leu His Asn His Tyr Thr Gln Lys Ser Leu Ser Leu Ser Leu Gly
        435                 440                 445

Lys

<210> SEQ ID NO 297
<211> LENGTH: 645
<212> TYPE: DNA
<213> ORGANISM: Artificial Sequence
<220> FEATURE:
<223> OTHER INFORMATION: synthetic

<400> SEQUENCE: 297
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgtggac tttcggccaa     300
gggaccaagg tggaaatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645

<210> SEQ ID NO 298
<211> LENGTH: 214
<212> TYPE: PRT
<213> ORGANISM: Artificial Sequence
<220> FEATURE:
<223> OTHER INFORMATION: synthetic

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 299
<211> LENGTH: 369
<212> TYPE: DNA
<213> ORGANISM: Artificial Sequence
<220> FEATURE:
<223> OTHER INFORMATION: synthetic

<400> SEQUENCE: 299
caggtgcagc tggtggagtc tgggggaggc gtggtccagc ctggggaggtc cctgagactc      60 tcctgtgaag tctctggatt cacatttagt aattatggca tgcactgggt ccgccaggct     120
ccaggcaagg ggctggagtg gtggcagtt gtatcatatg atggaagtaa taaatactat     180
acagactccg tgaagggccg attcaccatc tccagagaca attccaagaa cacgctgtct     240
ctgcaaatga atagcctgag agctgaagac acggctgtgt attactgtgc gaaagatcgg     300
ggtatcactg gcacctcggg cggtgttttt gatatctggg gccaagggac aatggtcacc     360
gtctcttca                                                              369

<210> SEQ ID NO 300
<211> LENGTH: 123
<212> TYPE: PRT
<213> ORGANISM: Artificial Sequence
<220> FEATURE:
<223> OTHER INFORMATION: synthetic

<400> SEQUENCE: 300

Gln Val Gln Leu Val Glu Ser Gly Gly Gly Val Val Gln Pro Gly Arg
1               5                   10                  15

Ser Leu Arg Leu Ser Cys Glu Val Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Val Ser Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Arg Gly Ile Thr Gly Thr Ser Gly Gly Val Phe Asp Ile
            100                 105                 110

Trp Gly Gln Gly Thr Met Val Thr Val Ser Ser
        115                 120

<210> SEQ ID NO 301
<211> LENGTH: 24
<212> TYPE: DNA
<213> ORGANISM: Artificial Sequence
<220> FEATURE:
<223> OTHER INFORMATION: synthetic

<400> SEQUENCE: 301
ggattcacat ttagtaatta tggc                                              24

```
<210> SEQ ID NO 302
<211> LENGTH: 24
<212> TYPE: DNA
<213> ORGANISM: Artificial Sequence
<220> FEATURE:
<223> OTHER INFORMATION: synthetic

<400> SEQUENCE: 302
gtatcatatg atggaagtaa taaa                                            24

<210> SEQ ID NO 303
<211> LENGTH: 8
<212> TYPE: PRT
<213> ORGANISM: Artificial Sequence
<220> FEATURE:
<223> OTHER INFORMATION: synthetic

<400> SEQUENCE: 303

Val Ser Tyr Asp Gly Ser Asn Lys
1               5

<210> SEQ ID NO 304
<211> LENGTH: 48
<212> TYPE: DNA
<213> ORGANISM: Artificial Sequence
<220> FEATURE:
<223> OTHER INFORMATION: synthetic

<400> SEQUENCE: 304
gcgaaagatc ggggtatcac tggcacctcg gcggtgtttt tgatatc                   48

<210> SEQ ID NO 305
<211> LENGTH: 15
<212> TYPE: PRT
<213> ORGANISM: Artificial Sequence
<220> FEATURE:
<223> OTHER INFORMATION: synthetic

<400> SEQUENCE: 305

Ala Lys Asp Arg Gly Ile Thr Gly Thr Ser Gly Gly Val Phe Asp
1               5                   10                  15

<210> SEQ ID NO 306
<211> LENGTH: 321
<212> TYPE: DNA
<213> ORGANISM: Artificial Sequence
<220> FEATURE:
<223> OTHER INFORMATION: synthetic

<400> SEQUENCE: 306
gccatccgga tgacccagtc tccatcctca ttctctgcaa ctacaggaga cagagtcacc     60
atcacttgtc gggcgagtca gggtattagc agtcatttag cctggtatca gcaaaaacca    120
gggaaagccc ctaagttcct gatctatgtt gcatccactt tgcaaagtgg ggtcccatca    180
aggttcagcg gcagtggatc tgggacagat ttcactctca ccatcagcag cctgcagtct    240
gaagattttg caacttatta ctgtcaacag tattatagtt accctccgac gttcggccaa    300
gggaccaagg tggaaatcaa a                                              321

<210> SEQ ID NO 307
<211> LENGTH: 107
<212> TYPE: PRT
<213> ORGANISM: Artificial Sequence
<220> FEATURE:
<223> OTHER INFORMATION: synthetic
```

<400> SEQUENCE: 307

Ala Ile Arg Met Thr Gln Ser Pro Ser Phe Ser Ala Thr Thr Gly
1               5                   10                  15

Asp Arg Val Thr Ile Thr Cys Arg Ala Ser Gln Gly Ile Ser Ser His
            20                  25                  30

Leu Ala Trp Tyr Gln Gln Lys Pro Gly Lys Ala Pro Lys Phe Leu Ile
        35                  40                  45

Tyr Val Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Tyr Tyr Ser Tyr Pro Pro
                85                  90                  95

Thr Phe Gly Gln Gly Thr Lys Val Glu Ile Lys
            100                 105

<210> SEQ ID NO 308
<211> LENGTH: 18
<212> TYPE: DNA
<213> ORGANISM: Artificial Sequence
<220> FEATURE:
<223> OTHER INFORMATION: synthetic

<400> SEQUENCE: 308
cagggtatta gcagtcat                                                18

<210> SEQ ID NO 309
<211> LENGTH: 6
<212> TYPE: PRT
<213> ORGANISM: Artificial Sequence
<220> FEATURE:
<223> OTHER INFORMATION: synthetic

<400> SEQUENCE: 309

Gln Gly Ile Ser Ser His
1               5

<210> SEQ ID NO 310
<211> LENGTH: 9
<212> TYPE: DNA
<213> ORGANISM: Artificial Sequence
<220> FEATURE:
<223> OTHER INFORMATION: synthetic

<400> SEQUENCE: 310 gttgcatcc                                                           9

<210> SEQ ID NO 311
<211> LENGTH: 3
<212> TYPE: PRT
<213> ORGANISM: Artificial Sequence
<220> FEATURE:
<223> OTHER INFORMATION: synthetic

<400> SEQUENCE: 311

Val Ala Ser
1

<210> SEQ ID NO 312
<211> LENGTH: 27
<212> TYPE: DNA
<213> ORGANISM: Artificial Sequence

```
<220> FEATURE:
<223> OTHER INFORMATION: synthetic

<400> SEQUENCE: 312
caacagtatt atagttaccc tccgacg                                        27

<210> SEQ ID NO 313
<211> LENGTH: 9
<212> TYPE: PRT
<213> ORGANISM: Artificial Sequence
<220> FEATURE:
<223> OTHER INFORMATION: synthetic

<400> SEQUENCE: 313

Gln Gln Tyr Tyr Ser Tyr Pro Pro Thr
1               5

<210> SEQ ID NO 314
<211> LENGTH: 1353
<212> TYPE: DNA
<213> ORGANISM: Artificial Sequence
<220> FEATURE:
<223> OTHER INFORMATION: synthetic

<400> SEQUENCE: 314
caggtgcagc tggtggagtc tgggggaggc gtggtccagc ctggaggtc cctgagactc      60
tcctgtgaag tctctggatt cacatttagt aattatggca tgcactgggt ccgccaggct    120
ccaggcaagg ggctggagtg ggtggcagtt gtatcatatg atggaagtaa taaatactat    180
acagactccg tgaagggccg attcaccatc tccagagaca attccaagaa cacgctgtct    240
ctgcaaatga atagcctgag agctgaagac acggctgtgt attactgtgc gaaagatcgg    300
ggtatcactg gcacctcggg cggtgttttt gatatctggg ccaagggac aatggtcacc     360
gtctcttcag cctccaccaa gggcccatcg gtcttccccc tggcgccctg ctccaggagc    420
acctccgaga gcacagccgc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acgaagacct acacctgcaa cgtagatcac aagcccagca caccaaggt ggacaagaga     660
gttgagtcca aatatggtcc cccatgccca cctgcccag cacctgagtt cctggggga     720
ccatcagtct tcctgttccc cccaaaaccc aaggacactc tcatgatctc ccggacccct    780
gaggtcacgt gcgtggtggt ggacgtgagc caggaagacc ccgaggtcca gttcaactgg    840
tacgtggatg gcgtggaggt gcataatgcc aagacaaagc cgcgggagga gcagttcaac    900
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc   1020
aaagccaaag gcagccccg agagccacag gtgtacaccc tgcccccatc ccaggaggag    1080
atgaccaaga accaggtcag cctgacctgc ctggtcaaag gcttctaccc cagcgacatc    1140
gccgtggagt gggagagcaa tgggcagccg gagaacaact acaagaccac gcctcccgtg   1200
ctggactccg acggctcctt cttcctctac agcaggctca ccgtggacaa gagcaggtgg   1260
caggagggga atgtcttctc atgctccgtg atgcatgagg ctctgcacaa ccactacaca   1320
cagaagtccc tctccctgtc tctgggtaaa tga                                1353

<210> SEQ ID NO 315
<211> LENGTH: 450
```

```
<212> TYPE: PRT
<213> ORGANISM: Artificial Sequence
<220> FEATURE:
<223> OTHER INFORMATION: synthetic

<400> SEQUENCE: 315
```

| | | | | | | | | | | | | | | |
|---|---|---|---|---|---|---|---|---|---|---|---|---|---|---|
| Gln | Val | Gln | Leu | Val | Glu | Ser | Gly | Gly | Gly | Val | Val | Gln | Pro | Gly | Arg |
| 1 | | | | 5 | | | | | 10 | | | | | 15 | |
| Ser | Leu | Arg | Leu | Ser | Cys | Glu | Val | Ser | Gly | Phe | Thr | Phe | Ser | Asn | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | | 35 | | | | 40 | | | | | 45 | | | |
| Ala | Val | Val | Ser | Tyr | Asp | Gly | Ser | Asn | Lys | Tyr | Tyr | Thr | Asp | Ser | Val |
| 50 | | | | | 55 | | | | | 60 | | | | | |
| Lys | Gly | Arg | Phe | Thr | Ile | Ser | Arg | Asp | Asn | Ser | Lys | Asn | Thr | Leu | Ser |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Asp | Arg | Gly | Ile | Thr | Gly | Thr | Ser | Gly | Gly | Val | Phe | Asp | Ile |
| | | | 100 | | | | | 105 | | | | | 110 | | |
| Trp | Gly | Gln | Gly | Thr | Met | Val | Thr | Val | Ser | Ser | Ala | Ser | Thr | Lys | Gly |
| | | | 115 | | | | | 120 | | | | | 125 | | |
| Pro | Ser | Val | Phe | Pro | Leu | Ala | Pro | Cys | Ser | Arg | Ser | Thr | Ser | Glu | Ser |
| 130 | | | | | 135 | | | | | 140 | | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Lys | Thr | Tyr | Thr | Cys | Asn | Val |
| | | | 195 | | | | | 200 | | | | | 205 | | |
| Asp | His | Lys | Pro | Ser | Asn | Thr | Lys | Val | Asp | Lys | Arg | Val | Glu | Ser | Lys |
| 210 | | | | | 215 | | | | | 220 | | | | | |
| Tyr | Gly | Pro | Pro | Cys | Pro | Pro | Cys | Pro | Ala | Pro | Glu | Phe | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | Gln | Glu |
| | | | 260 | | | | | 265 | | | | | 270 | | |
| Asp | Pro | Glu | Val | Gln | Phe | Asn | Trp | Tyr | Val | Asp | Gly | Val | Glu | Val | His |
| | | | 275 | | | | | 280 | | | | | 285 | | |
| Asn | Ala | Lys | Thr | Lys | Pro | Arg | Glu | Glu | Gln | Phe | Asn | Ser | Thr | Tyr | Arg |
| 290 | | | | | 295 | | | | | 300 | | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Gly | Leu | Pro | Ser | Ser | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Gln | Glu | Glu | Met | Thr | Lys | Asn | Gln | Val | Ser | Leu |
| | | | 355 | | | | | 360 | | | | | 365 | | |
| Thr | Cys | Leu | Val | Lys | Gly | Phe | Tyr | Pro | Ser | Asp | Ile | Ala | Val | Glu | Trp |
| 370 | | | | | 375 | | | | | 380 | | | | | |

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
        435                 440                 445

Gly Lys
    450

<210> SEQ ID NO 316
<211> LENGTH: 645
<212> TYPE: DNA
<213> ORGANISM: Artificial Sequence
<220> FEATURE:
<223> OTHER INFORMATION: synthetic

<400> SEQUENCE: 316
gccatccgga tgacccagtc tccatcctca ttctctgcaa ctacaggaga cagagtcacc        60
atcacttgtc gggcgagtca gggtattagc agtcatttag cctggtatca gcaaaaacca       120
gggaaagccc ctaagttcct gatctatgtt gcatccactt tgcaaagtgg ggtcccatca       180
aggttcagcg gcagtggatc tgggacagat ttcactctca ccatcagcag cctgcagtct       240
gaagattttg caacttatta ctgtcaacag tattatagtt accctccgac gttcggccaa       300
gggaccaagg tggaaatcaa acgaactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gttag                      645

<210> SEQ ID NO 317
<211> LENGTH: 214
<212> TYPE: PRT
<213> ORGANISM: Artificial Sequence
<220> FEATURE:
<223> OTHER INFORMATION: synthetic

<400> SEQUENCE: 317

Ala Ile Arg Met Thr Gln Ser Pro Ser Ser Phe Ser Ala Thr Thr Gly
1               5                   10                  15

Asp Arg Val Thr Ile Thr Cys Arg Ala Ser Gln Gly Ile Ser Ser His
            20                  25                  30

Leu Ala Trp Tyr Gln Gln Lys Pro Gly Lys Ala Pro Lys Phe Leu Ile
        35                  40                  45

Tyr Val Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Tyr Tyr Ser Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 318
<211> LENGTH: 342
<212> TYPE: DNA
<213> ORGANISM: Artificial Sequence
<220> FEATURE:
<223> OTHER INFORMATION: synthetic

<400> SEQUENCE: 318

```
gaggtgcagc tggtggagtc ggggggaggc ttggtccagc ctggggggtc cctgagactc    60
tcctgtgcag cctctggatt cacgtctagt agatattgga tgagttgggt ccgccaggct   120
ccagggaagg ggctggagtg gctggccaac ataaatcaag acggaagtga aaaatactat   180
ctggagtctc tgaggggccg attcaccatc tccagagaca acgccaagaa ctcactgtat   240
ctgcaaatga acaacctgag agccgaggac acggctgtgt attactgtgc gagggatgag   300
gaaggttact ggggccaggg aaccctggtc accgtctcct ca                      342
```

<210> SEQ ID NO 319
<211> LENGTH: 114
<212> TYPE: PRT
<213> ORGANISM: Artificial Sequence
<220> FEATURE:
<223> OTHER INFORMATION: synthetic

<400> SEQUENCE: 319

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Ser Ser Arg Tyr
            20                  25                  30
Trp Met Ser Trp Val Arg Gln Ala Pro Gly Lys Gly Leu Glu Trp Leu
        35                  40                  45
Ala Asn Ile Asn Gln Asp Gly Ser Glu Lys Tyr Tyr Leu Glu Ser Leu
    50                  55                  60
Arg Gly Arg Phe Thr Ile Ser Arg Asp Asn Ala Lys Asn Ser Leu Tyr
65                  70                  75                  80
Leu Gln Met Asn Asn Leu Arg Ala Glu Asp Thr Ala Val Tyr Tyr Cys
                85                  90                  95
Ala Arg Asp Glu Glu Gly Tyr Trp Gly Gln Gly Thr Leu Val Thr Val
            100                 105                 110
Ser Ser
```

<210> SEQ ID NO 320
<211> LENGTH: 24
<212> TYPE: DNA
<213> ORGANISM: Artificial Sequence

```
<220> FEATURE:
<223> OTHER INFORMATION: synthetic

<400> SEQUENCE: 320
ggattcacgt ctagtagata ttgg                                              24

<210> SEQ ID NO 321
<211> LENGTH: 8
<212> TYPE: PRT
<213> ORGANISM: Artificial Sequence
<220> FEATURE:
<223> OTHER INFORMATION: synthetic

<400> SEQUENCE: 321

Gly Phe Thr Ser Ser Arg Tyr Trp
1               5

<210> SEQ ID NO 322
<211> LENGTH: 24
<212> TYPE: DNA
<213> ORGANISM: Artificial Sequence
<220> FEATURE:
<223> OTHER INFORMATION: synthetic

<400> SEQUENCE: 322
ataaatcaag acggaagtga gaaa                                              24

<210> SEQ ID NO 323
<211> LENGTH: 8
<212> TYPE: PRT
<213> ORGANISM: Artificial Sequence
<220> FEATURE:
<223> OTHER INFORMATION: synthetic

<400> SEQUENCE: 323

Ile Asn Gln Asp Gly Ser Glu Lys
1               5

<210> SEQ ID NO 324
<211> LENGTH: 21
<212> TYPE: DNA
<213> ORGANISM: Artificial Sequence
<220> FEATURE:
<223> OTHER INFORMATION: synthetic

<400> SEQUENCE: 324
gcgagggatg aggaaggtta c                                                 21

<210> SEQ ID NO 325
<211> LENGTH: 7
<212> TYPE: PRT
<213> ORGANISM: Artificial Sequence
<220> FEATURE:
<223> OTHER INFORMATION: synthetic

<400> SEQUENCE: 325

Ala Arg Asp Glu Glu Gly Tyr
1               5

<210> SEQ ID NO 326
<211> LENGTH: 336
<212> TYPE: DNA
<213> ORGANISM: Artificial Sequence
<220> FEATURE:
<223> OTHER INFORMATION: synthetic
```

-continued

```
<400> SEQUENCE: 326
gatgttgtga tgactcagtc tctactctcc ctgtccgtca cccttggaca gccggcctcc    60
atctcctgca ggtctagtca aagcctcgta tacagtgatg gggacaccta cttgagttgg   120
tttcagcaga ggccaggcca atctccacgg cgcctaattt ataaggtttc tcaccgggac   180
tctggggtcc cagacagatt cagaggcagt ggttcaggca ctgatttcac actgaaaatc   240
agcagggtgg aggctgagga tgttgggatt tattactgca tgcaaggtac acactggcct   300
ccgacgttcg gccaagggac caaggtggaa atcaaa                             336

<210> SEQ ID NO 327
<211> LENGTH: 112
<212> TYPE: PRT
<213> ORGANISM: Artificial Sequence
<220> FEATURE:
<223> OTHER INFORMATION: synthetic

<400> SEQUENCE: 327

Asp Val Val Met Thr Gln Ser Leu Leu Ser Leu Ser Val Thr Leu Gly
1               5                   10                  15

Gln Pro Ala Ser Ile Ser Cys Arg Ser Ser Gln Ser Leu Val Tyr Ser
            20                  25                  30

Asp Gly Asp Thr Tyr Leu Ser Trp Phe Gln Gln Arg Pro Gly Gln Ser
        35                  40                  45

Pro Arg Arg Leu Ile Tyr Lys Val Ser His Arg Asp Ser Gly Val Pro
    50                  55                  60

Asp Arg Phe Arg Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Pro Thr Phe Gly Gln Gly Thr Lys Val Glu Ile Lys
            100                 105                 110

<210> SEQ ID NO 328
<211> LENGTH: 33
<212> TYPE: DNA
<213> ORGANISM: Artificial Sequence
<220> FEATURE:
<223> OTHER INFORMATION: synthetic

<400> SEQUENCE: 328
caaagcctcg tatacagtga tggggacacc tac                                 33

<210> SEQ ID NO 329
<211> LENGTH: 11
<212> TYPE: PRT
<213> ORGANISM: Artificial Sequence
<220> FEATURE:
<223> OTHER INFORMATION: synthetic

<400> SEQUENCE: 329

Gln Ser Leu Val Tyr Ser Asp Gly Asp Thr Tyr
1               5                   10

<210> SEQ ID NO 330
<211> LENGTH: 9
<212> TYPE: DNA
<213> ORGANISM: Artificial Sequence
<220> FEATURE:
<223> OTHER INFORMATION: synthetic
```

```
<400> SEQUENCE: 330 aaggtttct                                                                              9

<210> SEQ ID NO 331
<211> LENGTH: 3
<212> TYPE: PRT
<213> ORGANISM: Artificial Sequence
<220> FEATURE:
<223> OTHER INFORMATION: synthetic

<400> SEQUENCE: 331

Lys Val Ser
1

<210> SEQ ID NO 332
<211> LENGTH: 27
<212> TYPE: DNA
<213> ORGANISM: Artificial Sequence
<220> FEATURE:
<223> OTHER INFORMATION: synthetic

<400> SEQUENCE: 332
atgcaaggta cacactggcc tccgacg                                                         27

<210> SEQ ID NO 333
<211> LENGTH: 9
<212> TYPE: PRT
<213> ORGANISM: Artificial Sequence
<220> FEATURE:
<223> OTHER INFORMATION: synthetic

<400> SEQUENCE: 333

Met Gln Gly Thr His Trp Pro Pro Thr
1               5

<210> SEQ ID NO 334
<211> LENGTH: 1326
<212> TYPE: DNA
<213> ORGANISM: Artificial Sequence
<220> FEATURE:
<223> OTHER INFORMATION: synthetic

<400> SEQUENCE: 334
gaggtgcagc tggtggagtc ggggggaggc ttggtccagc ctgggggtc cctgagactc            60 tcctgtgcag cctctggatt cacgtctagt agatattgga tgagttgggt ccgccaggct          120
ccagggaagg gctggagtg gctggccaac ataaatcaag acggaagtga gaaatactat           180
ctggagtctc tgaggggccg attcaccatc tccagagaca acgccaagaa ctcactgtat          240
ctgcaaatga acaacctgag agccgaggac acggctgtgt attactgtgc gagggatgag          300
gaaggttact ggggccaggg aaccctggtc accgtctcct cagcctccac caagggccca          360
tcggtcttcc ccctggcgcc ctgctccagg agcacctccg agagcacagc cgccctgggc          420
tgcctggtca aggactactt ccccgaaccg gtgacggtgt cgtggaactc aggcgccctg          480
accagcggcg tgcacacctt cccggctgtc ctacagtcct caggactcta ctccctcagc          540
agcgtggtga ccgtgccctc cagcagcttg ggcacgaaga cctacacctg caacgtagat          600
cacaagccca gcaacaccaa ggtggacaag agagttgagt ccaaatatgg tcccccatgc          660
ccaccctgcc cagcacctga gttcctgggg ggaccatcag tcttcctgtt ccccccaaaa          720
cccaaggaca ctctcatgat ctcccggacc cctgaggtca cgtgcgtggt ggtggacgtg          780
agccaggaag accccgaggt ccagttcaac tggtacgtgg atggcgtgga ggtgcataat          840
```

-continued

```
gccaagacaa agccgcggga ggagcagttc aacagcacgt accgtgtggt cagcgtcctc      900
accgtcctgc accaggactg gctgaacggc aaggagtaca agtgcaaggt ctccaacaaa      960
ggcctcccgt cctccatcga gaaaaccatc tccaaagcca agggcagcc ccgagagcca      1020 caggtgtaca ccctgccccc atcccaggag gagatgacca gaaccaggt cagcctgacc      1080 tgcctggtca aaggcttcta ccccagcgac atcgccgtgg agtgggagag caatgggcag      1140
ccggagaaca actacaagac cacgcctccc gtgctggact ccgacggctc cttcttcctc      1200
tacagcaggc tcaccgtgga caagagcagg tggcaggagg ggaatgtctt ctcatgctcc      1260
gtgatgcatg aggctctgca caaccactac acacagaagt ccctctccct gtctctgggt      1320
aaatga                                                                1326
```

<210> SEQ ID NO 335
<211> LENGTH: 441
<212> TYPE: PRT
<213> ORGANISM: Artificial Sequence
<220> FEATURE:
<223> OTHER INFORMATION: synthetic

<400> SEQUENCE: 335

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Arg Tyr
            20                  25                  30

Trp Met Ser Trp Val Arg Gln Ala Pro Gly Lys Gly Leu Glu Trp Leu
        35                  40                  45

Ala Asn Ile Asn Gln Asp Gly Ser Glu Lys Tyr Tyr Leu Glu Ser Leu
    50                  55                  60

Arg Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr Tyr Cys
                85                  90                  95

Ala Arg Asp Glu Glu Gly Tyr Trp Gly Gln Gly Thr Leu Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Phe Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270
```

Val Asp Gly Val Glu Val His Asn Ala Lys Thr Lys Pro Arg Glu Glu
            275                 280                 285

Gln Phe Asn Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys
        435                 440

<210> SEQ ID NO 336
<211> LENGTH: 660
<212> TYPE: DNA
<213> ORGANISM: Artificial Sequence
<220> FEATURE:
<223> OTHER INFORMATION: synthetic

<400> SEQUENCE: 336
gatgttgtga tgactcagtc tctactctcc ctgtccgtca cccttggaca gccggcctcc      60
atctcctgca ggtctagtca agcctcgta tacagtgatg ggacaccta cttgagttgg      120 tttcagcaga ggccaggcca atctccacgg cgcctaattt ataaggtttc taccgggac      180 tctggggtcc cagacagatt cagaggcagt ggttcaggca ctgatttcac actgaaaatc      240
agcagggtgg aggctgagga tgttggaatt tattactgca tgcaaggtac acactggcct      300
ccgacgttcg gccaagggac caaggtggaa atcaaacgaa ctgtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgttag      660

<210> SEQ ID NO 337
<211> LENGTH: 219
<212> TYPE: PRT
<213> ORGANISM: Artificial Sequence
<220> FEATURE:
<223> OTHER INFORMATION: synthetic

<400> SEQUENCE: 337

Asp Val Val Met Thr Gln Ser Leu Leu Ser Leu Ser Val Thr Leu Gly
1               5                   10                  15

```
Gln Pro Ala Ser Ile Ser Cys Arg Ser Ser Gln Ser Leu Val Tyr Ser
            20                  25                  30

Asp Gly Asp Thr Tyr Leu Ser Trp Phe Gln Gln Arg Pro Gly Gln Ser
        35                  40                  45

Pro Arg Arg Leu Ile Tyr Lys Val Ser His Arg Asp Ser Gly Val Pro
    50                  55                  60

Asp Arg Phe Arg Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Pro Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 338
<211> LENGTH: 131
<212> TYPE: PRT
<213> ORGANISM: Artificial Sequence
<220> FEATURE:
<223> OTHER INFORMATION: Amino acids 1-103: Human ACVR1 extracellular
      domain (21-123 of accession number Q04771) Amino acids 104-131:
      Myc-myc-hexahistidine tag

<400> SEQUENCE: 338

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Glu Gln Lys Leu Ile Ser Glu Glu Asp
            100                 105                 110

Leu Gly Gly Glu Gln Lys Leu Ile Ser Glu Glu Asp Leu His His His
        115                 120                 125

His His His
    130
```

<210> SEQ ID NO 339
<211> LENGTH: 336
<212> TYPE: PRT
<213> ORGANISM: Artificial Sequence
<220> FEATURE:
<223> OTHER INFORMATION: Amino acids 1-103: Human ACVR1 extracellular
      domain (21-123 of accession number Q04771) Amino acids 104-336:
      mFc

<400> SEQUENCE: 339

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
                20                  25                  30

Cys Phe Ser Ser Leu Ser Ile Asn Asp Gly Phe His Val Tyr Gln Lys
            35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Glu Pro Arg Gly Pro Thr Ile Lys Pro
            100                 105                 110

Cys Pro Pro Cys Lys Cys Pro Ala Pro Asn Leu Leu Gly Gly Pro Ser
        115                 120                 125

Val Phe Ile Phe Pro Pro Lys Ile Lys Asp Val Leu Met Ile Ser Leu
    130                 135                 140

Ser Pro Ile Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Leu Arg Val Val
            180                 185                 190

Ser Ala Leu Pro Ile Gln His Gln Asp Trp Met Ser Gly Lys Glu Phe
        195                 200                 205

Lys Cys Lys Val Asn Asn Lys Asp Leu Pro Ala Pro Ile Glu Arg Thr
    210                 215                 220

Ile Ser Lys Pro Lys Gly Ser Val Arg Ala Pro Gln Val Tyr Val Leu
225                 230                 235                 240

Pro Pro Pro Glu Glu Glu Met Thr Lys Lys Gln Val Thr Leu Thr Cys
                245                 250                 255

Met Val Thr Asp Phe Met Pro Glu Asp Ile Tyr Val Glu Trp Thr Asn
            260                 265                 270

Asn Gly Lys Thr Glu Leu Asn Tyr Lys Asn Thr Glu Pro Val Leu Asp
        275                 280                 285

Ser Asp Gly Ser Tyr Phe Met Tyr Ser Lys Leu Arg Val Glu Lys Lys
    290                 295                 300

Asn Trp Val Glu Arg Asn Ser Tyr Ser Cys Ser Val Val His Glu Gly
305                 310                 315                 320

Leu His Asn His His Thr Thr Lys Ser Phe Ser Arg Thr Pro Gly Lys
                325                 330                 335

<210> SEQ ID NO 340
<211> LENGTH: 131
<212> TYPE: PRT
<213> ORGANISM: Artificial Sequence -continued

```
<220> FEATURE:
<223> OTHER INFORMATION: Amino acids 1-103: Mouse ACVR1 extracellular
      domain (21-123 of accession number P37172) Amino acids 104-131:
      Myc-myc-hexahistidine tag

<400> SEQUENCE: 340

Val Glu Asp Glu Lys Pro Lys Val Asn Gln Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Glu Gln Lys Leu Ile Ser Glu Glu Asp
            100                 105                 110

Leu Gly Gly Glu Gln Lys Leu Ile Ser Glu Glu Asp Leu His His His
        115                 120                 125

His His His
    130

<210> SEQ ID NO 341
<211> LENGTH: 509
<212> TYPE: PRT
<213> ORGANISM: Artificial Sequence
<220> FEATURE:
<223> OTHER INFORMATION: Human ACVR1 Accession Q04771

<400> SEQUENCE: 341

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190
```

Gly Ser Gly Leu Pro Phe Leu Val Gln Arg Thr Val Ala Arg Gln Ile
            195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 342
<211> LENGTH: 509
<212> TYPE: PRT
<213> ORGANISM: Artificial Sequence
<220> FEATURE:
<223> OTHER INFORMATION: Mouse ACVR1 Accession P37172

<400> SEQUENCE: 342

Met Val Asp Gly Val Met Ile Leu Pro Val Leu Met Met Ala Phe
1               5                   10                  15

Pro Ser Pro Ser Val Glu Asp Glu Lys Pro Lys Val Asn Gln Lys Leu
            20                  25                  30

Tyr Met Cys Val Cys Glu Gly Leu Ser Cys Gly Asn Glu Asp His Cys
        35                  40                  45

```
Glu Gly Gln Gln Cys Phe Ser Ser Leu Ser Ile Asn Asp Gly Phe His
    50              55                  60
Val Tyr Gln Lys Gly Cys Phe Gln Val Tyr Glu Gln Gly Lys Met Thr
65              70              75                  80
Cys Lys Thr Pro Pro Ser Pro Gly Gln Ala Val Glu Cys Cys Gln Gly
                85              90                  95
Asp Trp Cys Asn Arg Asn Ile Thr Ala Gln Leu Pro Thr Lys Gly Lys
            100             105             110
Ser Phe Pro Gly Thr Gln Asn Phe His Leu Glu Val Gly Leu Ile Ile
        115             120             125
Leu Ser Val Val Phe Ala Val Cys Leu Leu Ala Cys Ile Leu Gly Val
130             135             140
Ala Leu Arg Lys Phe Lys Arg Arg Asn Gln Glu Arg Leu Asn Pro Arg
145             150             155             160
Asp Val Glu Tyr Gly Thr Ile Glu Gly Leu Ile Thr Thr Asn Val Gly
                165             170             175
Asp Ser Thr Leu Ala Glu Leu Leu Asp His Ser Cys Thr Ser Gly Ser
            180             185             190
Gly Ser Gly Leu Pro Phe Leu Val Gln Arg Thr Val Ala Arg Gln Ile
        195             200             205
Thr Leu Leu Glu Cys Val Gly Lys Gly Arg Tyr Gly Glu Val Trp Arg
210             215             220
Gly Ser Trp Gln Gly Glu Asn Val Ala Val Lys Ile Phe Ser Ser Arg
225             230             235             240
Asp Glu Lys Ser Trp Phe Arg Glu Thr Glu Leu Tyr Asn Thr Val Met
                245             250             255
Leu Arg His Glu Asn Ile Leu Gly Phe Ile Ala Ser Asp Met Thr Ser
            260             265             270
Arg His Ser Ser Thr Gln Leu Trp Leu Ile Thr His Tyr His Glu Met
        275             280             285
Gly Ser Leu Tyr Asp Tyr Leu Gln Leu Thr Thr Leu Asp Thr Val Ser
    290             295             300
Cys Leu Arg Ile Val Leu Ser Ile Ala Ser Gly Leu Ala His Leu His
305             310             315             320
Ile Glu Ile Phe Gly Thr Gln Gly Lys Ser Ala Ile Ala His Arg Asp
                325             330             335
Leu Lys Ser Lys Asn Ile Leu Val Lys Lys Asn Gly Gln Cys Cys Ile
            340             345             350
Ala Asp Leu Gly Leu Ala Val Met His Ser Gln Ser Thr Asn Gln Leu
        355             360             365
Asp Val Gly Asn Asn Pro Arg Val Gly Thr Lys Arg Tyr Met Ala Pro
    370             375             380
Glu Val Leu Asp Glu Thr Ile Gln Val Asp Cys Phe Asp Ser Tyr Lys
385             390             395             400
Arg Val Asp Ile Trp Ala Phe Gly Leu Val Leu Trp Glu Val Ala Arg
                405             410             415
Arg Met Val Ser Asn Gly Ile Val Glu Asp Tyr Lys Pro Pro Phe Tyr
            420             425             430
Asp Val Val Pro Asn Asp Pro Ser Phe Glu Asp Met Arg Lys Val Val
        435             440             445
Cys Val Asp Gln Gln Arg Pro Asn Ile Pro Asn Arg Trp Phe Ser Asp
    450             455             460
```

| | | | | | | | | | | | | | | |
|---|---|---|---|---|---|---|---|---|---|---|---|---|---|---|
| Pro | Thr | Leu | Thr | Ser | Leu | Ala | Lys | Leu | Met | Lys | Glu | Cys | Trp | Tyr | Gln |
| 465 | | | | | 470 | | | | 475 | | | | | 480 |
| Asn | Pro | Ser | Ala | Arg | Leu | Thr | Ala | Leu | Arg | Ile | Lys | Lys | Thr | Leu | Thr |
| | | | | 485 | | | | | 490 | | | | | 495 |
| Lys | Ile | Asp | Asn | Ser | Leu | Asp | Lys | Leu | Lys | Thr | Asp | Cys |
| | | | | 500 | | | | | 505 |

ANTI-ACVR1 ANTIBODIES AND USES THEREOF

CROSS REFERENCES TO RELATED APPLICATIONS

This application claims the benefit under 35 U.S.C. § 119(e) of U.S. provisional application No. 62/975,047, filed Feb. 11, 2020, and U.S. provisional application No. 63/030,131, filed May 26, 2020, the entire contents of each of which are incorporated herein by reference.

SEQUENCE LISTING

The instant application includes a Sequence Listing which has been submitted electronically in ASCI format and is hereby incorporated by reference in its entirety. Said ASCI copy, created on Feb. 10, 2021 is named Sequence-Listing-40848-0101USU1 and is 274 kilobytes (KB) in size.

FIELD OF THE INVENTION

The present invention is related to antibodies and antigen-binding fragments of antibodies that specifically bind to Activin A receptor type 1 (ACVR1) and/or ACVR1 mutant proteins, and therapeutic and diagnostic methods of using those antibodies.

BACKGROUND OF THE INVENTION

Activin A receptor type 1 (ACVR1; also known as ActR1; or Activin receptor-like kinase 2; ALK2) is a single-pass transmembrane receptor, and a member of the type I Bone Morphogenic Protein (BMP) receptor of the TGF-β receptor super family. Upon ligand binding, ACVR1 together with a type II receptor initiates a downstream signaling cascade leading to activation of receptor specific R-SMAD protein (SMAD1, SMAD5, or SMAD8) which then associates with SMAD4, leading to transcriptional regulation of genes (Massague 1998, Massaque et al. 2005).

Mutations in ACVR1 gene which encodes the BMP type I receptor ALK2, also known as ACVR1 protein, may cause fibroplasia ossificans progressiva (FOP), a rare disorder leading to progressive ectopic bone formation in soft tissues with severe impairment of body movements because of extraskeletal bone bridges. ACVR1 mutations responsible for FOP cause dysregulation of SMAD-dependent downstream signaling and confer to the mutated receptor the ability to respond to noncanonical ligand, Activin A, triggering ectopic bone formation. Gain of function mutations in the gene encoding ACVR1 lead to debilitating disorders of extra-skeletal (heterotopic) ossification in humans such as FOP. For example, the typical FOP patient may have the amino acid arginine substituted for the amino acid histidine at position 206 of ACVR1 protein. This causes a change in glycine-serine activation domain of the protein, which converts an Acvr1:Activin A:Acvr2 non-signaling complex into a signaling complex. The result of the Activin neo-function is that Fibro-adipogenic progenitor (FAP) cells initiate endochondral ossification. Atypical mutations involving other residues may work similarly, resulting in the ACVR1 protein to be stuck in its active conformation despite no BMP being present. Mutations in the ACVR1 gene may also be linked to diffuse intrinsic pontine glioma (DIPG).

The liver expression of the key iron regulator hepcidin is controlled by the bone morphogenic protein (BMP)/SMAD pathway. BMP signaling requires the ligand (e.g., BMP7, BMP6, or BMP2), type I (e.g., ACVR1), type II receptors (e.g., ACVR2 or BMPR2), and coreceptor hemojuvelin (HJV) to phosphorylate SMAD proteins. BMP6 mediated activation of ACVR1 directly activates transcription of Hamp, the gene that encodes hepcidin. Hepcidin is a negative regulator of iron levels by causing internalization of ferroportin (slc40a1), the only known iron exporter. Inhibition of the BMP6-ACVR1 signaling cascade leads to decreased Hamp transcription, resulting in decreased circulating levels of hepcidin. A reduction of circulating hepcidin results in increased ferroportin levels, which allows increased uptake of iron from the small intestines, thereby increasing circulating iron levels.

Monoclonal antibodies to ACVR1 are described in Katagiri et al., US Patent/Publication Nos. 10428148, 20180118835, and in WO 2019172165.

Fully human antibodies that specifically bind to ACVR1 protein, a fragment thereof, or a mutant thereof with high affinity and that inhibit ACVR1-mediated bone morphogenetic protein (BMP) signal transduction could be important in the prevention and treatment of, e.g., heterotopic ossification, ectopic ossification, bone dysplasia, anemia, or diffuse intrinsic pontine glioma.

BRIEF SUMMARY OF THE INVENTION

The present invention provides antibodies and antigen-binding fragments thereof that specifically bind to an Activin A receptor type 1 (ACVR1) protein and inhibit ACVR1-mediated BMP signal transduction. In certain embodiments, the anti-ACVR1 antibodies are fully human antibodies that bind to ACVR1 with high affinity and block ACVR1 or destabilize the activated conformation. The antibodies of the present invention are useful, inter alia, for deactivating or decreasing the activity of ACVR1 protein. In certain embodiments, the antibodies are useful in preventing, treating or ameliorating at least one symptom or indication of a ACVR1-associated disease or disorder in a subject. In certain embodiments, the antibodies may be administered prophylactically or therapeutically to a subject having or at risk of having a ACVR1-associated disease or disorder. In specific embodiments, the antibodies are used in the prevention and treatment of heterotopic ossification, ectopic ossification, bone dysplasia, anemia, or certain cancers, including brain tumors when administered to a subject in need thereof.

In some embodiments, the antibodies of the invention bind to an ACVR1 protein and/or a mutant thereof. Further, the antibodies disclosed herein bind to an ACVR1 protein or a mutant thereof with high affinity. ACVR1 proteins used in the present invention include ACVR1 proteins which may be derived from a mammal such as a human or a mouse. For example, the full-length amino acid sequence of human ACVR1 is available with reference to UniProtKB Accession No. Q04771 (SEQ ID NO: 341).

The ACVR1 protein may include a signal peptide occurring at positions 1-20 of ACVR1 protein, for example, of accession number Q04771 (SEQ ID NO: 341). The mature ACVR1 protein may include amino acids 21-509, for example, of accession number Q04771 (SEQ ID NO: 341). The ACVR1 protein may include an extracellular domain at amino acids 21-123 of, for example, accession number Q04771 (SEQ ID NO: 341). The ACVR1 protein may include a transmembrane domain at amino acids 124-146 of, for example, accession number Q04771 (SEQ ID NO: 341). The ACVR1 protein may include a protein kinase domain within positions 208-502, for example, of accession number Q04771 (SEQ ID NO: 341). The ACVR protein may include glycosylation at amino acid position 102 comprising an N-linked (GlcNAc . . . ) asparagine, for example, of accession number Q04771 (SEQ ID NO: 341). The ACVR protein may include a modified residue for example, such as phosphoserine at position 501, for example, of accession number Q04771 (SEQ ID NO: 341).

Mutations in the ACVR1 gene may be a responsible for various diseases including FOP. The ACVR1 protein may be a mutant ACVR1 protein having amino acid substitutions which may be found in various familial and sporadic FOP cases. The human ACVR1 protein may comprise various mutations, including but not limited to L196P (mutation that substitutes leucine at position 196 by proline), delP197_F198insL (mutation that deletes proline at position 197 and phenylalanine at position 198 and inserts leucine), R202I (mutation that substitutes arginine at position 202 by isoleucine), R206H (mutation that substitutes arginine at position 206 by histidine), Q207E (mutation that substitutes glutamine at position 207 by glutamic acid), R258S (mutation that substitutes arginine at position 258 by serine), R258G (mutation that substitutes arginine at position 258 by glycine), G325A (mutation that substitutes glycine at position 325 by alanine), G328E (mutation that substitutes glycine at position 328 by glutamic acid), G328R (mutation that substitutes glycine at position 328 by arginine), G328W (mutation that substitutes glycine at position 328 by tryptophan), G356D (mutation that substitutes glycine at position 356 by aspartic acid), and R375P (mutation that substitutes arginine at position 375 by proline) of SEQ ID NO: 341.

As another example, the full-length amino acid sequence of mouse ACVR1 protein is available with reference to Accession No. P37172 (SEQ ID NO: 342).

The antibodies of the invention can be full-length (for example, an IgG1 or IgG4 antibody) or may comprise only an antigen-binding portion (for example, a Fab, F(ab') 2 or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to an ACVR1 protein. In some embodiments, the antibodies are fully human monoclonal antibodies.

Exemplary anti-ACVR1 antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDRs) (HCDR1, HCDR2 and HCDR3), and light chain complementarity determining regions (LCDRs) (LCDR1, LCDR2 and LCDR3) of exemplary antibodies. Table 2 sets forth the nucleic acid sequence identifiers of the HCVRs, LCVRs, HCDR1, HCDR2 HCDR3, LCDR1, LCDR2 and LCDR3 of the exemplary antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-ACVR1 antibodies listed in Table 1. In certain embodiments, the anti-ACVR1 antibodies of the invention comprise an HCVR/LCVR amino acid sequence pair selected from one of SEQ ID NOs: 2/10 (e.g., mAb27396), 22/30 (e.g., mAb27241), 22/72 (e.g., mAb27245), 42/48 (e.g., mAb27242), 58/62 (e.g., mAb27243), 76/84 (e.g., mAb27247), 96/104 (e.g., mAb27404), 116/119 (e.g., mAb27405), 128/136 (e.g., mAb27400), 203/211 (e.g., mAb29226), 273/277 (e.g., mAb29257), and 300/307 (e.g., mAb29266).

The present invention also provides antibodies, or antigen-binding fragments thereof, comprising a HCVR and a LCVR, said HCVR comprising an amino acid sequence listed in Table 1 having no more than twelve amino acid substitutions, and/or said LCVR comprising an amino acid sequence listed in Table 1 having no more than ten amino acid substitutions. For example, the present invention provides antibodies or antigen-binding fragments thereof comprising a HCVR and a LCVR, said HCVR comprising an amino acid sequence listed in Table 1, said amino acid sequence having one, two, three, four, five, six, seven, eight, nine, ten, eleven or twelve amino acid substitutions. In another example, the present invention provides antibodies or antigen-binding fragments thereof comprising a HCVR and a LCVR, said LCVR comprising an amino acid sequence listed in Table 1, said amino acid sequence having one, two, three, four, five, six, seven, eight, nine or ten amino acid substitutions. In one embodiment, the present invention provides anti-ACVR1 antibodies or antigen-binding fragments thereof comprising a HCVR and a LCVR, said HCVR comprising an amino acid sequence listed in Table 1, said amino acid sequence having at least one amino acid substitution, and/or said LCVR comprising an amino acid sequence listed in Table 1, said amino acid sequence having at least one amino acid substitution.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-ACVR1 antibodies listed in Table 1. In certain embodiments, the HCDR3/LCDR3 amino acid sequence pair is selected from the group consisting of SEQ ID NOs:28/36 (e.g., mAb27242), 60/66 (e.g., mAb27243), 82/90 (e.g., mAb27247), 8/16 (e.g., mAb27396), 102/110 (e.g., mAb27405), 28/66 (e.g., mAb27245), 134/142 (e.g., mAb27400), 209/217 (e.g., mAb29226), 261/283 (e.g., mAb29257), and 305/313 (e.g., mAb29266).

The present invention also provides antibodies, or antigen-binding fragments thereof, comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present invention provides antibodies, or antigen-binding fragments thereof, comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present invention provides antibodies, or antigen-binding fragments thereof, comprising a HCVR and a LCVR, said HCVR comprising HCDR1 comprising an amino acid sequence of SEQ ID NO: 24 or 44 or an amino acid sequence differing from SEQ ID NO: 24 or 44 by 1 amino acid, HCDR2 comprising an amino acid sequence of SEQ ID NO: 46 or an amino acid sequence differing from SEQ ID NO: 46 by 1 amino acid, and HCDR3 comprising an amino acid sequence of SEQ ID NO: 28 or 60 or an amino acid sequence differing from SEQ ID NO: 28 or 60 by 1 amino acid. In another exemplary embodiment, the present invention provides antibodies, or antigen-binding fragments thereof, comprising a HCVR and a LCVR, said LCVR comprising LCDR1 comprising an amino acid sequence of SEQ ID NO: 50 or an amino acid sequence differing from SEQ ID NO: 50 by 1 amino acid, LCDR2 comprising an amino acid sequence of SEQ ID NO: 52 or 64 or an amino acid sequence differing from SEQ ID NO: 52 or 64 by 1 amino acid, and LCDR3 comprising an amino acid sequence of SEQ ID NO: 36 or 66 or an amino acid sequence differing from SEQ ID NO: 36 or 66 by 1 amino acid.

The present invention also provides antibodies, or antigen-binding fragments thereof, comprising a set of six CDRs HCDR1-HCDR2-HCDR3-LCDR1-LCDR2-LCDR3) contained within any of the exemplary antibodies listed in Table 1. In certain embodiments, the HCDR1-HCDR2-HCDR3-LCDR1-LCDR2-LCDR3 amino acid sequence set is selected from the group consisting of SEQ ID NOs: 44-46-28-50-52-36 (e.g., mAb27242), 24-46-60-50-64-66 (e.g., mAb27243), 78-80-82-86-88-90 (e.g., mAb27247), 4-6-8-12-14-16 (e.g., mAb27396), 98-100-102-106-122-110 (e.g., mAb27405), 98-100-102-106-108-110 (e.g., mAb27404), 24-26-28-50-64-66 (e.g., mAb27245), 24-26-28-32-34-36 (e.g., mAb27241), 130-132-134-138-140-142 (e.g., mAb27400), 205-207-209-213-215-217 (e.g., mAb29226), 257-275-261-279-281-283 (e.g., mAb29257), and 4-303-305-309-311-313 (e.g., mAb29266).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., mAb27396), 22/30 (e.g., mAb27241), 22/72 (e.g., mAb27245), 42/48 (e.g., mAb27242), 58/62 (e.g., mAb27243), 76/84 (e.g., mAb27247), 96/104 (e.g., mAb27404), 116/119 (e.g., mAb27405), 128/136 (e.g., mAb27400), 203/211 (e.g., mAb29226), 273/277 (e.g., mAb29257), and 300/307 (e.g., mAb29266).

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., Proc. Natl. Acad. Sci. USA 86:9268-9272 (1989). Public databases are also available for identifying CDR sequences within an antibody.

In certain embodiments, the present invention includes an antibody or antigen-binding fragment thereof that binds specifically to ACVR1, wherein the antibody or antigen-binding fragment thereof comprises three heavy chain complementarity determining regions (CDRs) (HCDR1, HCDR2 and HCDR3) contained within a heavy chain variable region (HCVR) and three light chain CDRs (LCDR1, LCDR2 and LCDR3) contained within a light chain variable region (LCVR), wherein the HCVR comprises: (i) an amino acid sequence selected from the group consisting of SEQ ID NOs: 2, 22, 42, 58, 76, 96, 116, 128, 148, 166, 186, 203, 223, 241, 255, 273, 289, 300, and 319; (ii) an amino acid sequence having at least 90% identity to the amino acid sequence selected from the group consisting of SEQ ID NOs: 2, 22, 42, 58, 76, 96, 116, 128, 148, 166, 186, 203, 223, 241, 255, 273, 289, 300, and 319; (iii) an amino acid sequence having at least 95% identity to the amino acid sequence selected from the group consisting of SEQ ID NOs: 2, 22, 42, 58, 76, 96, 116, 128, 148, 166, 186, 203, 223, 241, 255, 273, 289, 300, and 319; or (iv) an amino acid sequence selected from the group consisting of SEQ ID NOs: 2, 22, 42, 58, 76, 96, 116, 128, 148, 166, 186, 203, 223, 241, 255, 273, 289, 300, and 319, said amino acid sequence having no more than 12 amino acid substitutions; and the LCVR comprises: (a) an amino acid sequence selected from the group consisting of SEQ ID NOs: 10, 30, 48, 62, 72, 84, 104, 119, 136, 156, 174, 193, 211, 231, 245, 263, 277, 293, 307, and 327; (b) an amino acid sequence having at least 90% identity to the amino acid sequence selected from the group consisting of SEQ ID NOs: 10, 30, 48, 62, 72, 84, 104, 119, 136, 156, 174, 193, 211, 231, 245, 263, 277, 293, 307, and 327; (c) an amino acid sequence having at least 95% identity to the amino acid sequence selected from the group consisting of SEQ ID NOs: 30, 48, 62, 72, 84, 104, 119, 136, 156, 174, 193, 211, 231, 245, 263, 277, 293, 307, and 327; or (d) an amino acid sequence selected from the group consisting of SEQ ID NOs: 10, 30, 48, 62, 72, 84, 104, 119, 136, 156, 174, 193, 211, 231, 245, 263, 277, 293, 307, and 327, said amino acid sequence having no more than 10 amino acid substitutions.

In certain preferred embodiments, the present invention includes antibodies that bind specifically to ACVR1 in an antagonist manner, i.e., decrease or block ACVR1 binding and/or activity.

The present invention includes anti-ACVR1 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In certain embodiments, the present invention provides antibodies and antigen-binding fragments thereof that exhibit pH-dependent binding to ACVR1. For example, the present invention includes antibodies and antigen-binding fragment thereof that bind ACVR1 with higher affinity at neutral pH than at acidic pH (i.e., reduced binding at acidic pH).

The present invention also provides for antibodies and antigen-binding fragments thereof that compete for specific binding to ACVR1 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that cross-compete for binding to ACVR1 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1. The present invention also provides antibodies and antigen-binding fragments thereof that bind to the same epitope as a reference antibody or antigen-binding fragment thereof comprising three CDRs of a HCVR and three CDRs of a LCVR, wherein the HCVR and LCVR each has an amino acid sequence selected from the HCVR and LCVR sequences listed in Table 1.

The present invention also provides isolated antibodies and antigen-binding fragments thereof that inhibit ligand-induced signaling by BMP7, Activin A or other TGFBeta family ligand forming a signaling complex with an Activin type II receptor. In some embodiments, the antibody or antigen-binding fragment thereof prevents ACVR1 from forming signaling complex with an Activin type II receptor. The present invention provides isolated antibodies and antigen-binding fragments thereof that may bind to the same epitope on ACVR1 as BMP7 or Activin A or an Activin type II receptor or may bind to a different epitope on ACVR1 as BMP7 or Activin A or an Activin type II receptor.

In certain embodiments, the antibodies or antigen-binding fragments of the present invention are bispecific comprising a first binding specificity to a first epitope of ACVR1 and a second binding specificity to a second epitope of ACVR1 wherein the first and second epitopes are distinct and non-overlapping.

In certain embodiments, the present invention provides an isolated antibody or antigen-binding fragment thereof that has one or more of the following characteristics:

(a) is a fully human monoclonal antibody;
(b) binds to human ACVR1 extracellular domain fused to an Fc (e.g., SEQ ID NO: 339) at 25° C. with a dissociation constant ($K_D$) of less than 60 nM, less than 12 nM, less than less than 2 nM, less than 1 nM, or less than 0.5 nM as measured in a surface plasmon resonance assay;
(c) binds to human ACVR1 extracellular domain fused to mFc (SEQ ID NO: 339) at 37° C. with a dissociation constant ($K_D$) of less than 150 nM, less than 15 nM, less than less than 5 nM, less than 1.5 nM, or less than 1 nM as measured in a surface plasmon resonance assay;
(d) binds to human ACVR1 extracellular domain fused to myc-myc-hexahistag (e.g., SEQ ID NO: 338) at 25° C. with a $K_D$ of less than 300 nM, less than 150 nM, less than 25 nM, less than 10 nM, less than 5 nM, less than 3 nM or less than 2 nM as measured in a surface plasmon resonance assay;
(e) binds to human ACVR1 extracellular domain fused to myc-myc-hexahistag (e.g., SEQ ID NO: 338) at 37° C. with a $K_D$ of less than 500 nM, less than 50 nM, less than 25 nM, less than 10 nM, as measured in a surface plasmon resonance assay; (f) does not bind mouse ACVR1 or binds to mouse ACVR1 extracellular domain fused to myc-myc-hexahistag (e.g., SEQ ID NO: 340) at 25° C. with a $K_D$ of greater than 500 nM, as measured in a surface plasmon resonance assay; (g) does not bind mouse ACVR1 or binds to mouse ACVR1 extracellular domain fused to myc-myc-hexahistag (e.g., SEQ ID NO: 340) at 37° C. with a $K_D$ of greater than 500 nM, as measured in a surface plasmon resonance assay;
(k) binds to cells expressing human ACVR1 protein or human ACVR (R206H) protein; (l) inhibits activation of cells expressing human ACVR1(R206H) by human Activin A with a IC$_{50}$ of less than as measured in a cell-based bioassay;

(m) inhibits activation of cells expressing human ACVR1 (R206H) by human BMP7 with a IC$_{50}$ of less than 20 nM, less than 5 nM, less than 3 nM, or less than 1 nM, or less than as measured in a cell-based bioassay;

(m) significantly decreases serum hepcidin when administered to mice expressing human ACVR1 in place of mouse allele; (n) significantly increases serum iron levels when administered to mice expressing human ACVR1 in place of mouse allele; and/or (o) inhibits wild-type ACVR1 signaling when administered to mice expressing human ACVR1 in place of mouse allele; and (o) comprises a HCVR comprising an amino acid sequence selected from the group consisting of HCVR sequence listed in Table 1 and a LCVR comprising an amino acid sequence selected from the group consisting of LCVR sequences listed in Table 1.

In a second aspect, the present invention provides nucleic acid molecules encoding anti-ACVR1 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs HCDR1-HCDR2-HCDR3), wherein the HCDR1-HCDR2-HCDR3 amino acid sequence set is as defined by any of the exemplary antibodies listed in Table 1.

The present invention also provides nucleic acid molecules encoding an LCVR, wherein the LCVR comprises a set of three CDRs LCDR1-LCDR2-LCDR3), wherein the LCDR1-LCDR2-LCDR3 amino acid sequence set is as defined by any of the exemplary antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 1, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-ACVR1 antibody listed in Table 1.

In a related aspect, the present invention provides recombinant expression vectors capable of expressing a polypeptide comprising a heavy and/or light chain variable region of an antibody. For example, the present invention includes recombinant expression vectors comprising any of the nucleic acid molecules mentioned above, i.e., nucleic acid molecules encoding any of the HCVR, LCVR, and/or CDR sequences as set forth in Table 2. In certain embodiments, the present invention provides expression vectors comprising: (a) a nucleic acid molecule comprising a nucleic acid sequence encoding a HCVR of an antibody that binds ACVR1, wherein the HCVR comprises an amino acid sequence selected from the group consisting of sequences listed in Table 1; and/or (b) a nucleic acid molecule comprising a nucleic acid sequence encoding a LCVR of an antibody that binds ACVR1, wherein the LCVR comprises an amino acid sequence selected from the group consisting of sequences listed in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced. In certain embodiments, the host cells comprise a mammalian cell or a prokaryotic cell. In certain embodiments, the host cell is a Chinese Hamster Ovary (CHO) cell or an *Escherichia coli* (*E. coli*) cell. In certain embodiments, the present invention provides methods of producing an antibody or antigen-binding fragment thereof of the invention, the methods comprising introducing into a host cell an expression vector comprising a nucleic acid sequence encoding a HCVR and/or LCVR of an antibody or antigen-binding fragment thereof of the invention operably linked to a promoter; culturing the host cell under conditions favorable for expression of the nucleic acid sequence; and isolating the antibody or antigen-binding fragment thereof from the culture medium and/or host cell. The isolated antibody or antigen-binding fragment thereof may be purified using any of the methods known in prior art.

In a third aspect, the invention provides a pharmaceutical composition comprising a therapeutically effective amount of at least one recombinant monoclonal antibody or antigen-binding fragment thereof which specifically binds ACVR1 and a pharmaceutically acceptable carrier. In a related aspect, the invention features a composition which is a combination of an anti-ACVR1 antibody and a second therapeutic agent. In one embodiment, the second therapeutic agent is any agent that is advantageously combined with an anti-ACVR1 antibody.

Exemplary agents that may be advantageously combined with an anti-ACVR1 antibody include, without limitation, other agents that bind and/or activate ACVR1 activity (including other antibodies or antigen-binding fragments thereof, etc.) and/or agents which do not directly bind ACVR1 but nonetheless treat or ameliorate at least one symptom or indication of a ACVR1-associated disease or disorder (disclosed elsewhere herein). Additional combination therapies and co-formulations involving the anti-ACVR1 antibodies of the present invention are disclosed elsewhere herein.

In a fourth aspect, the invention provides therapeutic methods for treating a disease or disorder associated with ACVR1 in a subject using an anti-ACVR1 antibody or antigen-binding portion of an antibody of the invention, wherein the therapeutic methods comprise administering a therapeutically effective amount of a pharmaceutical composition comprising an antibody or antigen-binding fragment of an antibody of the invention to the subject in need thereof. The disorder treated is any disease or condition which is improved, ameliorated, inhibited or prevented by potentiation of ACVR1 activity (e.g., anemia, heterotopic ossification, ectopic ossification, bone dysplasia, or diffuse intrinsic pontine glioma). In certain embodiments, the invention provides methods to prevent, or treat a ACVR1-associated disease or disorder comprising administering a therapeutically effective amount of an anti-ACVR1 antibody or antigen-binding fragment thereof of the invention to a subject in need thereof. In some embodiments, the antibody or antigen-binding fragment thereof may be administered prophylactically or therapeutically to a subject having or at risk of having a ACVR1-associated disease or disorder. In certain embodiments, the antibody or antigen-binding fragment thereof the invention is administered in combination with a second therapeutic agent to the subject in need thereof.

The second therapeutic agent may be selected from the group consisting of an anti-Activin A antibody or antigen-binding fragment thereof, anti-BMP7 antibody or antigen binding fragment thereof, anti-ACVR2 antibody or antigen-binding fragment thereof, anti-inflammatory drugs, steroids, bisphosphonates, muscle relaxants, or retinoic acid receptor (RAR) gamma agonists, a lifestyle modification, a dietary supplement and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur. The antibody or fragment thereof may be administered subcutaneously, intravenously, intradermally, intraperitoneally, orally, intramuscularly, or intracerebroventricularly. The antibody or fragment thereof may be administered at a dose of about 0.1 mg/kg of body weight to about 100 mg/kg of body weight of the subject. In certain embodiments, an antibody of the present invention may be administered at one or more doses comprising between 10 mg to 600 mg.

The present invention also includes use of an anti-ACVR1 antibody or antigen-binding fragment thereof of the invention in the manufacture of a medicament for the treatment of a disease or disorder that would benefit from the activation of ACVR1 binding and/or activity.

Other embodiments will become apparent from a review of the ensuing detailed description.

BRIEF DESCRIPTION OF THE FIGURES

FIG. 2A shows a representative image of HO volume in the injured hindlimb in an in vivo post-traumatic HO model in WT mice as measured by total HO volume by microCT, attached HO (encircled by broken white lines) or unattached HO (encircled by short dashed white lines) 13 weeks post-surgery after receiving isotype control antibody.

FIG. 2B shows a representative image of HO volume in the injured hindlimb in an in vivo post-traumatic HO model in WT mice as measured by total HO volume by microCT, attached HO (encircled by broken white lines) or unattached HO (encircled by short dashed white lines) 13 weeks post-surgery after receiving Alk3-Fc. HO volumes by micro CT were significantly reduced after 13 weeks in mice receiving ALK3-Fc compared to mice receiving isotype control.

FIG. 2C shows a representative image of HO volume in the injured hindlimb in an in vivo post-traumatic HO model in WT mice as measured by total volume by microCT, attached HO (encircled by broken white lines) or unattached HO (encircled by short dashed white lines) 13 weeks post-surgery after receiving anti-ACVR antibody mAb27242. HO volumes by micro CT were significantly reduced after 13 weeks in mice receiving anti-ACVR antibody compared to mice receiving isotype control antibody.

DETAILED DESCRIPTION

Figure 1A:
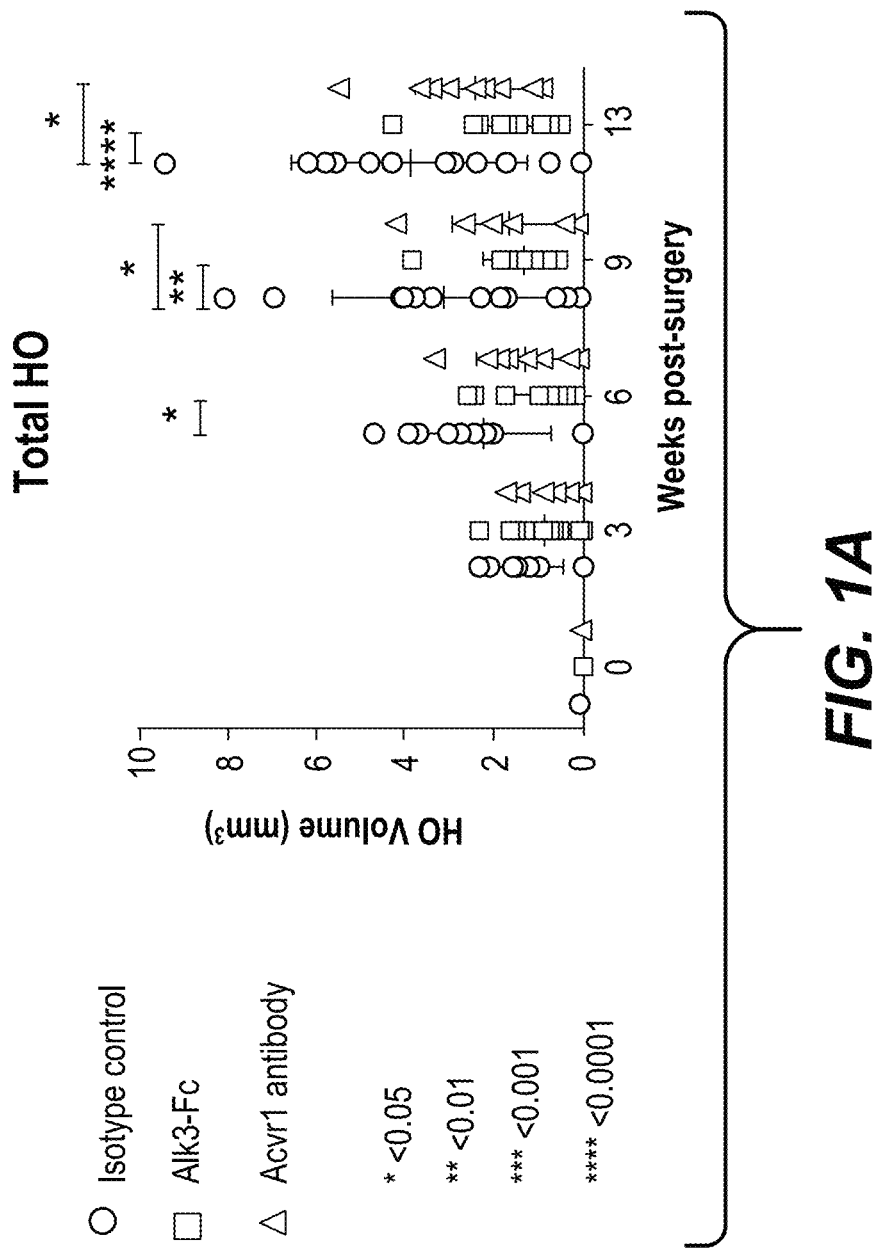
FIG. 1A shows a graph of total heterotopic ossification (HO) volume by microCT over a period of 13 weeks after surgery in an in vivo post-traumatic HO model in WT mice. Mice were administered either an isotype control antibody (circles, n=12), ALK3-Fc (squares, n=12) or an Acvr1 antibody mAb27242 (triangles, n=12) starting concurrently with induction of injury. HO volume was measured by pCT 3, 6, 9 and 13 weeks post injury. Acvr1 blocking antibodies significantly attenuated total HO compared to isotype control by 9 weeks post-surgery (p<0.05).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications, patents, and patent applications mentioned herein are incorporated herein by reference in their entirety.

Definitions

The term "ACVR1", also called "ALK2" refers to Activin A receptor type 1 (also known as Activin-like kinase 2). ACVR1 is a single-pass type I membrane protein. The full-length amino acid sequence of human ACVR1 is available with reference to UniProtKB Accession No. Q04771, as having 509 aa residues (SEQ ID NO: 341). The protein has an extracellular domain at amino acid residues 21-123, a transmembrane domain at amino acid positions 124-146, and a cytoplasmic domain at positions 147-509. On ligand binding, ACVR1 forms a receptor complex consisting of two type II and two type I transmembrane serine/threonine kinases. Type II receptors phosphorylate and activate type I receptors. Which autophosphorylate, then bind and activate SMAD transcriptional regulators. ACVR1 is a receptor for Activin.

The amino acid sequence of full-length human ACVR1 protein is exemplified by the amino acid sequence provided in UniProtKB/Swiss-Prot as accession number Q04771 (SEQ ID NO: 341). The full-length amino acid sequence of mouse ACVR1 protein is available with reference to Accession No. P37172 (SEQ ID NO: 342).

The term "ACVR1" includes recombinant ACVR1 protein or a fragment thereof. The term also encompasses ACVR1 protein or a fragment thereof coupled to, for example, a histidine tag, PADRE tag, mouse or human Fc, or a signal sequence (for example, SEQ ID NOs: 338-340). The term "ACVR1" may include an ACVR1 protein or a fragment thereof comprising a mutation. For example, the mutation may be based on corresponding amino acid sequence or fragment thereof of human ACVR1 UniProtKB Accession No. Q04771, (SEQ ID NO: 341). For example, the ACVR1 protein or fragment thereof may comprise a mutation, including but not limited to L196P, delP197_F198insL, R202I, R206H, Q207E, R258S, R258G, G325A, G328E, G328R, G328W, G356D, and R375P of corresponding SEQ ID NO: 341.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-ACVR1 monoclonal antibodies disclosed herein may comprise one or more amino acid substitutions, insertions and/or deletions in the framework and/or CDR regions of the heavy and light chain variable domains as compared to the corresponding germline sequences.

Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic biological properties, reduced immunogenicity, etc. Antibodies and antigen-binding fragments obtained in this general manner are encompassed within the present invention.

The present invention also includes fully human anti-ACVR1 monoclonal antibodies comprising variants of any of the HCVR, LCVR, and/or CDR amino acid sequences disclosed herein having one or more conservative substitutions. For example, the present invention includes anti-ACVR1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", or "fully human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo, for example in the CDRs and in particular CDR3. However, the term "human antibody", or "fully human antibody", as used herein, is not intended to include mAbs in which CDR sequences derived from the germline of another mammalian species (e.g., mouse), have been grafted onto human FR sequences. The term includes antibodies that are recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to ACVR1. Moreover, multi-specific antibodies that bind to one domain in ACVR1 and one or more additional antigens or a bi-specific that binds to two different regions of ACVR1 are nonetheless considered antibodies that "specifically bind", as used herein.

The term "high affinity" antibody refers to those mAbs having a binding affinity to ACVR1, expressed as $K_D$, of at least $10^{-8}$ M; preferably $10^{-9}$ M; more preferably $10^{-10}$ M, even more preferably $10^{-11}$ M, as measured by surface plasmon resonance, e.g., BIACORE™ or solution-affinity ELISA.

By the term "slow off rate", "Koff" or "kd" is meant an antibody that dissociates from ACVR1, with a rate constant of $1 \times 10^{-3}$ $s^{-1}$ or less, preferably $1 \times 10^{-4}$ $s^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to ACVR1 protein.

In specific embodiments, antibody or antibody fragments of the invention may be conjugated to a moiety such a ligand or a therapeutic moiety ("immunoconjugate"), a second anti-ACVR1 antibody, or any other therapeutic moiety useful for treating a ACVR1-associated disease or disorder.

An "isolated antibody", as used herein, is intended to refer to an antibody that is substantially free of other antibodies (Abs) having different antigenic specificities (e.g., an isolated antibody that specifically binds ACVR1, or a fragment thereof, is substantially free of Abs that specifically bind antigens other than ACVR1.

An "deactivating antibody" or an "antagonist antibody", as used herein (or an "antibody that decreases or blocks ACVR1 activity" or "an antibody that destabilizes the activated conformation"), is intended to refer to an antibody whose binding to ACVR1 results in deactivation of at least one biological activity of ACVR1. For example, an antibody of the invention may decrease anemia upon administration to a subject in need thereof.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a ACVR1-associated disease or disorder such as anemia or ectopic ossification. The term includes human subjects who have or are at risk of having such a disease or disorder.

As used herein, the terms "treat", "treating", or "treatment" refer to the reduction or amelioration of the severity of at least one symptom or indication of a ACVR1-associated disease or disorder due to the administration of a therapeutic agent such as an antibody of the present invention to a subject in need thereof. The terms include inhibition of progression of disease or of worsening of a symptom/indication. The terms also include positive prognosis of disease, i.e., the subject may be free of disease or may have reduced disease upon administration of a therapeutic agent such as an antibody of the present invention. The therapeutic agent may be administered at a therapeutic dose to the subject.

The terms "prevent", "preventing" or "prevention" refer to inhibition of manifestation of a ACVR1-associated disease or disorder or any symptoms or indications of such a disease or disorder upon administration of an antibody of the present invention.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to an ACVR1 protein, a fragment thereof, and/or mutant thereof. An antibody fragment may include a Fab fragment, a F(ab') 2 fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (Vi) $V_H$-$C_H2$-$C_H3$; (Vii) $V_H$-$C_L$; (Viii) $V_L$-$C_H1$; (ix) $V_L$-$C_H2$; (X) $V_L$-CH3; (xi) $V_L$-$C_H1$-$C_H2$; (XII) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric V H or V L domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to ACVR1.

An immunogen comprising any one of the following can be used to generate antibodies to ACVR1 protein. In certain embodiments, the antibodies of the invention are obtained from mice immunized with a full length, native ACVR1 protein (See, for example, UniProtKB/Swiss-Prot accession number Q04771) or with DNA encoding the protein or fragment thereof. Alternatively, the protein or a fragment thereof may be produced using standard biochemical techniques and modified and used as immunogen.

In some embodiments, the immunogen may be a recombinant ACVR1 protein or fragment thereof expressed in *E. coli* or in any other eukaryotic or mammalian cells such as Chinese hamster ovary (CHO) cells (for example, SEQ ID NOs: 338-340).

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to ACVR1 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild type or modified IgG1 or IgG4. While the constant region selected may vary according to specific use, high affinity antigen-binding and target specificity characteristics reside in the variable region.

Bioequivalents

The anti-ACVR1 antibodies and antibody fragments of the present invention encompass proteins having amino acid sequences that vary from those of the described antibodies, but that retain the ability to bind ACVR1 protein. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-ACVR1 Antibodies Comprising Fc Variants

According to certain embodiments of the present invention, anti-ACVR1 antibodies are provided comprising an Fc domain comprising one or more mutations which enhance or diminish antibody binding to the FcRn receptor, e.g., at acidic pH as compared to neutral pH. For example, the present invention includes anti-ACVR1 antibodies comprising a mutation in the $C_H2$ or a CH3 region of the Fc domain, wherein the mutation(s) increases the affinity of the Fc domain to FcRn in an acidic environment (e.g., in an endosome where pH ranges from about 5.5 to about 6.0).

Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-ACVR1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope of the present invention.

The present invention also includes anti-ACVR1 antibodies comprising a chimeric heavy chain constant ($C_H$) region, wherein the chimeric CH region comprises segments derived from the $C_H$ regions of more than one immunoglobulin isotype. For example, the antibodies of the invention may comprise a chimeric CH region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric CH region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric CH region as described herein may, in certain embodiments, exhibit modified Fc effector functions without adversely affecting the therapeutic or pharmacokinetic properties of the antibody. (See, e.g., U.S. Patent Application Publication 2014/0243504, the disclosure of which is hereby incorporated by reference in its entirety).

Biological Characteristics of the Antibodies

In general, the antibodies of the present invention function by binding to ACVR1 protein and decreasing its activity. For example, the present invention includes antibodies and antigen-binding fragments of antibodies that bind human ACVR1 protein (e.g., at 25° C. or at 37° C.) with a K D of less than 500 nM as measured by surface plasmon resonance, e.g., using the assay format as defined in Example 3 herein.

In certain embodiments, the antibodies or antigen-binding fragments thereof bind ACVR1 with a $K_D$ of less than about 500 nM, less than about 400 nM, less than about 300 nM, less than about 200 nM, less than about 100 nM, less than about 50 nM, less than about 25 nM, less than about 10 nM, less than about 5 nM, less than about 3 nM, less than about 2 nM, less than about 1 nM as measured by surface plasmon resonance, e.g., using the assay format as defined in Example 3 herein, or a substantially similar assay. In certain embodiments, the present invention provides an isolated anti-ACVR1 antibody or antigen-binding fragment thereof that is a fully human monoclonal antibody.

In certain embodiments, the antibodies or antigen-binding fragments thereof bind to human ACVR1 extracellular domain fused to an Fc (e.g., SEQ ID NO: 339) at 25° C. with a dissociation constant ($K_D$) of less than 60 nM, less than 12 nM, less than less than 2 nM, less than 1 nM, or less than 0.5 nM as measured in a surface plasmon resonance assay, e.g., using the assay format as defined in Example 3 herein, or a substantially similar assay.

In certain embodiments, the antibodies or antigen-binding fragments thereof bind to human ACVR1 extracellular domain fused to mFc (SEQ ID NO: 339) at 37° C. with a dissociation constant ($K_D$) of less than 150 nM, less than 15 nM, less than less than 5 nM, less than 1.5 nM, or less than 1 nM as measured in a surface plasmon resonance assay, e.g., using the assay format as defined in Example 3 herein, or a substantially similar assay.

In certain embodiments, the antibodies or antigen-binding fragments thereof bind to human ACVR1 extracellular domain fused to myc-myc-hexahistag (e.g., SEQ ID NO: 338) at 25° C. with a $K_D$ of less than 300 nM, less than 150 nM, less than 25 nM, less than 10 nM, less than 5 nM, less than 3 nM or less than 2 nM as measured in a surface plasmon resonance assay, e.g., using the assay format as defined in Example 3 herein, or a substantially similar assay.

In certain embodiments, the antibodies or antigen-binding fragments thereof bind to human ACVR1 extracellular domain fused to myc-myc-hexahistag (e.g., SEQ ID NO: 338) at 37° C. with a $K_D$ of less than 500 nM, less than 50 nM, less than 25 nM, less than 10 nM, as measured in a surface plasmon resonance assay, e.g., using the assay format as defined in Example 3 herein, or a substantially similar assay.

In certain embodiments, the antibodies or antigen-binding fragments thereof do not bind mouse ACVR1, e.g., using the assay format as defined in Example 3 herein, or a substantially similar assay.

In certain embodiments, the antibodies or antigen-binding fragments thereof bind to mouse ACVR1 extracellular domain fused to myc-myc-hexahistag (e.g., SEQ ID NO: 340) at 25° C. with a $K_D$ of greater than 500 nM, as measured in a surface plasmon resonance assay, e.g., using the assay format as defined in Example 3 herein, or a substantially similar assay.

In certain embodiments, the antibodies or antigen-binding fragments thereof bind to mouse ACVR1 extracellular domain fused to myc-myc-hexahistag (e.g., SEQ ID NO: 340) at 37° C. with a $K_D$ of greater than 500 nM, as measured in a surface plasmon resonance assay, e.g., using the assay format as defined in Example 3 herein, or a substantially similar assay. The present invention also includes antibodies or antigen-binding fragments thereof bind to cells expressing human ACVR1 protein or human ACVR (R206H) protein, e.g., using the assay format as defined in Example 5 herein, or a substantially similar assay.

In certain embodiments, the antibodies or antigen-binding fragments thereof inhibit activation of cells expressing human ACVR1(R206H) by human Activin A with a $IC_{50}$ of less than 25 nM, as measured in a cell-based bioassay, e.g., using the assay format as defined in Example 6 herein, or a substantially similar assay.

In certain embodiments, the antibodies or antigen-binding fragments thereof inhibit activation of cells expressing human ACVR1(R206H) by human BMP7 with a $IC_{50}$ of less than less than 5 nM, less than 3 nM, or less than 1 nM, or less than as measured in a cell-based bioassay, e.g., using the assay format as defined in Example 6 herein, or a substantially similar assay.

The invention also includes antibodies or antigen-binding fragments thereof that significantly decrease serum hepcidin when administered to mice expressing human ACVR1 in place of mouse allele, e.g., using the assay format as defined in Example 7 herein, or a substantially similar assay.

In certain embodiments, the antibodies or antigen-binding fragments thereof that significantly increase serum iron levels when administered to mice expressing human ACVR1 in place of mouse allele, e.g., using the assay format as defined in Example 7 herein, or a substantially similar assay.

In certain embodiments, the antibodies or antigen-binding fragments thereof inhibit wild-type ACVR1 signaling when administered to mice expressing human ACVR1 in place of mouse allele, e.g., using the assay format as defined in Example 7 herein, or a substantially similar assay.

In certain embodiments, the anti-ACVR antibodies or antigen-binding fragments thereof according to the invention significantly attenuate heterotopic ossification (HO) in a post-traumatic HO model in wild type mice, e.g., as described in Example 8 herein, or a substantially similar model.

In certain embodiments, the antibodies or antigen-binding fragments thereof specifically bind human ACVR1, a fragment thereof, or a mutant thereof, and comprise a HCVR comprising an amino acid sequence selected from the group consisting of HCVR sequence listed in Table 1 and a LCVR comprising an amino acid sequence selected from the group consisting of LCVR sequences listed in Table 1.

In one embodiment, the present invention provides an isolated recombinant antibody or antigen-binding fragment thereof that binds specifically to ACVR1 protein and inhibit ACVR1-mediated bone morphogenetic protein (BMP) signal transduction, wherein the antibody or fragment thereof exhibits one or more of the following characteristics: (a) is a fully human monoclonal antibody; (b) binds to human ACVR1 extracellular domain fused to an Fc (e.g., SEQ ID NO: 339) at with a dissociation constant ($K_D$) of less than 60 nM, less than 12 nM, less than less than 2 nM, less than 1 nM, or less than 0.5 nM as measured in a surface plasmon resonance assay; (c) binds to human ACVR1 extracellular domain fused to mFc (SEQ ID NO: 339) at 37° C. with a dissociation constant ($K_D$) of less than 150 nM, less than 15 nM, less than less than 5 nM, less than 1.5 nM, or less than 1 nM as measured in a surface plasmon resonance assay; (d) binds to human ACVR1 extracellular domain fused to myc-myc-hexahistag (e.g., SEQ ID NO: 338) at 25° C. with a $K_D$ of less than 300 nM, less than 150 nM, less than 25 nM, less than 10 nM, less than 5 nM, less than 3 nM or less than 2 nM as measured in a surface plasmon resonance assay; (e) binds to human ACVR1 extracellular domain fused to myc-myc-hexahistag (e.g., SEQ ID NO: 338) at 37° C. with a $K_D$ of less than 500 nM, less than 50 nM, less than 25 nM, less than 10 nM, as measured in a surface plasmon resonance assay; (f) does not bind mouse ACVR1 or binds to mouse ACVR1 extracellular domain fused to myc-myc-hexahistag (e.g., SEQ ID NO: 340) at 25° C. with a $K_D$ of greater than 500 nM, as measured in a surface plasmon resonance assay; (g) does not bind mouse ACVR1 or binds to mouse ACVR1 extracellular domain fused to myc-myc-hexahistag (e.g., SEQ ID NO: 340) at 37° C. with a $K_D$ of greater than 500 nM, as measured in a surface plasmon resonance assay; (k) binds to cells expressing human ACVR1 protein or human ACVR (R206H) protein; (l) inhibits activation of cells expressing human ACVR1 (R206H) by human Activin A with a $IC_{50}$ of less than 25 nM, as measured in a cell-based bioassay; (m) inhibits activation of cells expressing human ACVR1(R206H) by human BMP7 with a $IC_{50}$ of less than 20 nM, less than 5 nM, less than 3 nM, or less than 1 nM, or less than as measured in a cell-based bioassay; (m) significantly decreases serum hepcidin when administered to mice expressing human ACVR1 in place of mouse allele; (n) significantly increases serum iron levels when administered to mice expressing human ACVR1 in place of mouse allele; and/or (o) inhibits wild-type ACVR1 signaling when administered to mice expressing human ACVR1 in place of mouse allele; and (p) comprises a HCVR comprising an amino acid sequence selected from the group consisting of HCVR sequence listed in Table 1 and a LCVR comprising an amino acid sequence selected from the group consisting of LCVR sequences listed in Table 1.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Epitope Mapping and Related Technologies

The present invention includes anti-ACVR1 antibodies which interact with one or more amino acids found within one or more regions of the ACVR1 protein molecule. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the ACVR1 protein molecule (e.g. a linear epitope in a domain). Alternatively, the epitope may consist of a plurality of non-contiguous amino acids (or amino acid sequences) located within either or both of the aforementioned domains of the protein molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/ antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the present invention includes anti-ACVR1 antibodies and antigen-binding fragments thereof that interact with one or more epitopes found within the extracellular domain of ACVR1. The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular domain of ACVR1. Alternatively, the epitope may consist of a plurality of non-contiguous amino acids (or amino acid sequences) located within ACVR1 protein.

The present invention includes anti-ACVR1 antibodies that bind to the same epitope, or a portion of the epitope, as any of the specific exemplary antibodies listed in Table 1. Likewise, the present invention also includes anti-ACVR1 antibodies that compete for binding to ACVR1 protein or a fragment thereof with any of the specific exemplary antibodies listed in Table 1. For example, the present invention includes anti-ACVR1 antibodies that cross-compete for binding to ACV protein with one or more antibodies listed in Table 1.

One can easily determine whether an antibody binds to the same epitope as, or competes for binding with, a reference anti-ACVR1 antibody by using routine methods known in the art. For example, to determine if a test antibody binds to the same epitope as a reference anti-ACVR1 antibody of the invention, the reference antibody is allowed to bind to a ACVR1 protein or peptide under saturating conditions. Next, the ability of a test antibody to bind to the ACVR1 protein molecule is assessed. If the test antibody is able to bind to ACVR1 following saturation binding with the reference anti-ACVR1 antibody, it can be concluded that the test antibody binds to a different epitope than the reference anti-ACVR1 antibody. On the other hand, if the test antibody is not able to bind to the ACVR1 protein following saturation binding with the reference anti-ACVR1 antibody, then the test antibody may bind to the same epitope as the epitope bound by the reference anti-ACVR1 antibody of the invention.

To determine if an antibody competes for binding with a reference anti-ACVR1 antibody, the above-described binding methodology is performed in two orientations: In a first orientation, the reference antibody is allowed to bind to a ACVR1 protein under saturating conditions followed by assessment of binding of the test antibody to the ACVR1 molecule. In a second orientation, the test antibody is allowed to bind to a ACVR1 molecule under saturating conditions followed by assessment of binding of the reference antibody to the ACVR1 molecule. If, in both orientations, only the first (saturating) antibody is capable of binding to the ACVR1 molecule, then it is concluded that the test antibody and the reference antibody compete for binding to ACVR1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-ACVR1 monoclonal antibody conjugated to a therapeutic moiety ("immunoconjugate"), to treat an ACVR1-associated disease or disorder (e.g., anemia or ectopic ossification). As used herein, the term "immunoconjugate" refers to an antibody which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to ACVR1 protein. The type of therapeutic moiety that may be conjugated to the anti-ACVR1 antibody and will take into account the condition to be treated and the desired therapeutic effect to be achieved. Examples of suitable agents for forming immunoconjugates are known in the art; see for example, WO Multi-Specific Antibodies The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, ACVR1-specific antibodies are generated in a bi-specific format (a "bi-specific") in which variable regions binding to distinct domains of ACVR1 protein are linked together to confer dual-domain specificity within a single binding molecule. Appropriately designed bi-specifics may enhance overall ACVR1-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different VH domains (e.g., $V_H1$ and $V_H2$) to generate a bi-specific comprised of two binding "arms" ($V_H1$-$V_L1$ and $V_H2$-$V_L1$). Use of a single V L segment reduces the complexity of the system and thereby simplifies and increases efficiency in cloning, expression, and purification processes used to generate the bi-specific (See, for example, US2011/0195454 and US2010/0331527).

Alternatively, antibodies that bind more than one domains and a second target, such as, but not limited to, for example, a second different anti-ACVR1 antibody, may be prepared in a bi-specific format using techniques described herein, or other techniques known to those skilled in the art. Antibody variable regions binding to distinct regions may be linked together with variable regions that bind to relevant sites on, for example, the extracellular domain of ACVR1, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [*Epub: Dec.* 4, 2012]).

Therapeutic Administration and Formulations

The invention provides therapeutic compositions comprising the anti-ACVR1 antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 100 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 600 mg, about 5 to about 500 mg, or about 10 to about 400 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural, intracerebroventricular, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249:1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracranial, intraperitoneal and intramuscular injections, drip infusions, etc. These injectable preparations may be prepared by methods publicly known.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In treatment of DI PG, it may be necessary to overcome the blood-brain barrier. In certain embodiments, the blood-brain barrier is overcome by using one or more approaches disclosed in the art, e.g., in Parodi et al 2019, Pharmaceutics 11:245.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 300 mg and in about 10 to about 300 mg for the other dosage forms.

Therapeutic Uses of the Antibodies

The antibodies of the present invention are useful for the treatment, and/or prevention of a disease or disorder or condition associated with ACVR1 and/or for ameliorating at least one symptom associated with such disease, disorder or condition. In certain embodiments, an antibody or antigen-binding fragment thereof of the invention may be administered at a therapeutic dose to a patient with a disease or disorder or condition associated with ACVR1 or a mutant ACVR protein.

In certain embodiments, the antibodies of the present invention are useful for treating or preventing at least one symptom or indication of an ACVR1-associated or ACVR1 mutant protein-associated disease or disorder selected from the group consisting of heterotopic ossification, ectopic ossification, bone dysplasia, anemia, and diffuse intrinsic pontine glioma.

It is also contemplated herein to use one or more antibodies of the present invention prophylactically to subjects at risk for suffering from a ACVR1-associated disease or disorder. In one embodiment of the invention, the present antibodies are used for the preparation of a pharmaceutical composition or medicament for treating patients suffering from a disease, disorder or condition disclosed herein. In another embodiment of the invention, the present antibodies are used as adjunct therapy with any other agent or any other therapy known to those skilled in the art useful for treating or ameliorating a disease, disorder or condition disclosed herein.

Combination Therapies

Combination therapies may include an antibody of the invention and any additional therapeutic agent that may be advantageously combined with an antibody of the invention, or with a biologically active fragment of an antibody of the invention. The antibodies of the present invention may be combined synergistically with one or more drugs or therapy used to treat an ACVR1-associated or ACVR1 mutant protein-associated disease or disorder. In some embodiments, the antibodies of the invention may be combined with a second therapeutic agent to ameliorate one or more symptoms of said disease or condition.

Depending upon the disease, disorder or condition, the antibodies of the present invention may be used in combination with one or more additional therapeutic agents.

Examples of the additional therapeutic drug for ectopic ossification that can be administered in combination with the anti-ACVR1 antibody can include, but are not limited to, anti-Activin A inhibitor or antigen binding fragment thereof, and an anti-ACVR2 antibody or antigen-binding fragment thereof, anti-inflammatory drugs, steroids, bisphosphonates, muscle relaxants, and retinoic acid receptor (RAR) gamma agonists.

Activins belong to the transforming growth factor-beta (TGF-β) superfamily and exert a broad range of biological effects on cell proliferation, differentiation, metabolism, homeostasis, and apoptosis, as well as immune response and tissue repair. Activin A is a disulfide-linked homodimer (two beta-A chains) that binds to and activates heteromeric complexes of a type I (Act RI-A and Act RI-B) and a type II (Act RII-A and Act RII-B) serine-threonine kinase receptor. Activin A may act as a ligand to ACVR1 proteins or ACVR1 mutant proteins.

Examples of the anti-inflammatory drug can include aspirin, diclofenac, indomethacin, ibuprofen, ketoprofen, naproxen, piroxicam, rofecoxib, celecoxib, azathioprine, penicillamine, methotrexate, sulfasalazine, leflunomide, infliximab, and etanercept. Examples of the steroid can include prednisolone, beclomethasone, betamethasone, fluticasone, dexamethasone, and hydrocortisone. Examples of the bisphosphonate can include alendronate, cimadronate, clodronate, etidronate, ibandronate, incadronate, minodronate, neridronate, olpadronate, pamidronate, piridronate, risedronate, tiludronate, and zoledronate. Examples of the muscle relaxant can include cyclobenzaprine, metaxalone, and baclofen. Examples of the retinoic acid receptor gamma agonist can include palovarotene. Examples of the additional therapeutic drug for anemia may include recombinant erythropoietin (EPO) and iron supplements. Examples of additional therapeutic treatments for diffuse intrinsic pontine glioma may include radiation therapy, or experimental chemotherapy.

As used herein, the term "in combination with" means that additional therapeutically active component(s) may be administered prior to, concurrent with, or after the administration of the anti-ACVR1 antibody of the present invention. The term "in combination with" also includes sequential or concomitant administration of an anti-ACVR1 antibody and a second therapeutic agent.

The additional therapeutically active component(s) may be administered to a subject prior to administration of an anti-ACVR1 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, or less than 30 minutes before administration of the second component. In other embodiments, the additional therapeutically active component(s) may be administered to a subject after administration of an anti-ACVR1 antibody of the present invention. For example, a first component may be deemed to be administered "after" a second component if the first component is administered 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after or more after administration of the second component. In yet other embodiments, the additional therapeutically active component(s) may be administered to a subject concurrent with administration of an anti-ACVR1 antibody of the present invention. "Concurrent" administration, for purposes of the present invention, includes, e.g., administration of an anti-ACVR1 antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-ACVR1 antibody and the additional therapeutically active component may be administered intravenously, etc.); alternatively, each dosage form may be administered via a different route (e.g., the anti-ACVR1 antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-ACVR1 antibody "prior to", "concurrent with," or "after" (as those terms are defined herein above) administration of an additional therapeutically active component is considered administration of an anti-ACVR1 antibody "in combination with" an additional therapeutically active component.

The present invention includes pharmaceutical compositions in which an anti-ACVR1 antibody of the present invention is co-formulated with one or more of the additional therapeutically active component(s) as described elsewhere herein.

Diagnostic Uses of the Antibodies

The antibodies of the present invention may be used to detect and/or measure ACVR1 protein in a sample, e.g., for diagnostic purposes. Some embodiments contemplate the use of one or more antibodies of the present invention in assays to detect a ACVR1-associated- or ACVR mutant-protein-associated-disease or disorder. Exemplary diagnostic assays for ACVR1 may comprise, e.g., contacting a sample, obtained from a patient, with an anti-ACVR1 antibody of the invention, wherein the anti-ACVR1 antibody is labeled with a detectable label or reporter molecule or used as a capture ligand to selectively isolate ACVR1 from patient samples. Alternatively, an unlabeled anti-ACVR1 antibody can be used in diagnostic applications in combination with a secondary antibody which is itself detectably labeled. The detectable label or reporter molecule can be a radioisotope, such as 3H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure ACVR1 in a sample include enzyme-linked immunosorbent assay (ELISA), radioimmunoassay (RIA), and fluorescence-activated cell sorting (FACS).

Samples that can be used in ACVR1 diagnostic assays according to the present invention include any tissue or fluid sample obtainable from a patient, which contains detectable quantities of either ACVR1 protein, or fragments thereof, under normal or pathological conditions. Generally, levels of ACVR1 protein in a particular sample obtained from a healthy patient (e.g., a patient not afflicted with a disease associated with ACVR1) will be measured to initially establish a baseline, or standard, level of ACVR1. This baseline level of ACVR1 can then be compared against the levels of ACVR1 measured in samples obtained from individuals suspected of having a ACVR1-associated condition, or symptoms associated with such condition.

The antibodies specific for ACVR1 protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Activin A Receptor Receptor 1 (ACVR1)

Human antibodies to ACVR1 protein were generated in a VELOCIMMUNE® mouse comprising DNA encoding human Immunoglobulin heavy and kappa light chain variable regions. The mice were immunized with an immunogen comprising extracellular domain of human ACVR1 protein (e.g., SEQ ID NO: 339).

The antibody immune response was monitored by a ACVR1-specific immunoassay. When a desired immune response was achieved splenocytes were harvested and fused with mouse myeloma cells to preserve their viability and form hybridoma cell lines. The hybridoma cell lines were screened and selected to identify cell lines that produce ACVR1-specific antibodies. The cell lines were used to obtain several anti-ACVR1 chimeric antibodies (i.e., antibodies possessing human variable domains and mouse constant domains).

Anti-ACVR1 antibodies were also isolated directly from antigen-positive mouse B cells without fusion to myeloma cells, as described in U.S. Pat. No. 7,582,298, herein specifically incorporated by reference in its entirety. Using this method, several fully human anti-ACVR1 antibodies (i.e., antibodies possessing human variable domains and human constant domains) were obtained.

Exemplary antibodies generated as disclosed above were designated as mAb27396, mAb27241, mAb27242, mAb27243, mAb27245, mAb27247, mAb27404, mAb27405, mAb27400, mAb22124, mAb22125, mAb22168, mAb29226, mAb29226, mAb29237, mAb29256, mAb29257, mAb29261, mAb29266, mAb22115.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-ACVR1 antibodies of the invention.

TABLE 1

| Antibody Designation | Amino Acid Sequence Identifiers SEQ ID NO: | | | | | | | |
|---|---|---|---|---|---|---|---|---|
| | HCVR | HCDR1 | HCDR2 | HCDR3 | LCVR | LCDR1 | LCDR2 | LCDR3 |
| mAb27396 | 2 | 4 | 6 | 8 | 10 | 12 | 14 | 16 |
| mAb27241 | 22 | 24 | 26 | 28 | 30 | 32 | 34 | 36 |
| mAb27242 | 42 | 44 | 46 | 28 | 48 | 50 | 52 | 36 |
| mAb27243 | 58 | 24 | 46 | 60 | 62 | 50 | 64 | 66 |
| mAb27245 | 22 | 24 | 26 | 28 | 72 | 50 | 64 | 66 |
| mAb27247 | 76 | 78 | 80 | 82 | 84 | 86 | 88 | 90 |
| mAb27404 | 96 | 98 | 100 | 102 | 104 | 106 | 108 | 110 |
| mAb27405 | 116 | 98 | 100 | 102 | 119 | 106 | 122 | 110 |
| mAb27400 | 128 | 130 | 132 | 134 | 136 | 138 | 140 | 142 |
| mAb22124 | 148 | 150 | 152 | 154 | 156 | 158 | 14 | 160 |
| mAb22125 | 166 | 168 | 170 | 172 | 174 | 176 | 178 | 180 |
| mAb22168 | 186 | 188 | 152 | 191 | 193 | 195 | 178 | 197 |
| mAb29226 | 203 | 205 | 207 | 209 | 211 | 213 | 215 | 217 |
| mAb29233 | 223 | 225 | 227 | 229 | 231 | 233 | 178 | 235 |
| mAb29237 | 241 | 205 | 243 | 209 | 245 | 233 | 247 | 249 |
| mAb29256 | 255 | 257 | 259 | 261 | 263 | 265 | 14 | 267 |
| mAb29257 | 273 | 257 | 275 | 261 | 277 | 279 | 281 | 283 |
| mAb29261 | 289 | 257 | 291 | 261 | 293 | 233 | 178 | 235 |
| mAb29266 | 300 | 4 | 303 | 305 | 307 | 309 | 311 | 313 |
| mAb22115 | 319 | 321 | 323 | 325 | 327 | 329 | 331 | 333 |

The corresponding nucleic acid sequence identifiers are set forth in Table 2.

TABLE 2

Nucleic Acid Sequence Identifiers

| Antibody Designation | SEQ ID NO: | | | | | | | |
|---|---|---|---|---|---|---|---|---|
| | HCVR | HCDR1 | HCDR2 | HCDR3 | LCVR | LCDR1 | LCDR2 | LCDR3 |
| mAb27396 | 1 | 3 | 5 | 7 | 9 | 11 | 13 | 15 |
| mAb27241 | 21 | 23 | 25 | 27 | 29 | 31 | 33 | 35 |
| mAb27242 | 41 | 43 | 45 | 27 | 47 | 49 | 51 | 35 |
| mAb27243 | 57 | 23 | 45 | 59 | 61 | 49 | 63 | 65 |
| mAb27245 | 21 | 23 | 25 | 27 | 71 | 49 | 63 | 65 |
| mAb27247 | 75 | 77 | 79 | 81 | 83 | 85 | 87 | 89 |
| mAb27404 | 95 | 97 | 99 | 101 | 103 | 105 | 107 | 109 |
| mAb27405 | 115 | 117 | 99 | 101 | 118 | 120 | 121 | 109 |
| mAb27400 | 127 | 129 | 131 | 133 | 135 | 137 | 139 | 141 |
| mAb22124 | 147 | 149 | 151 | 153 | 155 | 157 | 13 | 159 |
| mAb22125 | 165 | 167 | 169 | 171 | 173 | 175 | 177 | 179 |
| mAb22168 | 185 | 187 | 189 | 190 | 192 | 194 | 177 | 196 |
| mAb29226 | 202 | 204 | 206 | 208 | 210 | 212 | 214 | 216 |
| mAb29233 | 222 | 224 | 226 | 228 | 230 | 232 | 177 | 234 |
| mAb29237 | 240 | 204 | 242 | 208 | 244 | 232 | 246 | 248 |
| mAb29256 | 254 | 256 | 258 | 260 | 262 | 264 | 13 | 266 |
| mAb29257 | 272 | 256 | 274 | 260 | 276 | 278 | 280 | 282 |
| mAb29261 | 288 | 256 | 290 | 260 | 292 | 232 | 177 | 294 |
| mAb29266 | 299 | 301 | 302 | 304 | 306 | 308 | 310 | 312 |
| mAb22115 | 318 | 320 | 322 | 324 | 326 | 328 | 330 | 332 |

Antibodies referred to herein typically have fully human variable regions, but may have human or mouse constant regions. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 or 2—will remain the same, and the binding properties to antigen are expected to be identical or substantially similar regardless of the nature of the Fc domain. In certain embodiments, selected antibodies with a mouse IgG1 Fc are converted to antibodies with human IgG4 Fc. In one embodiment, the IgG4 Fc domain comprises 2 or more amino acid changes as disclosed in US20100331527. In one embodiment, the human IgG4 Fc comprises a serine to proline mutation in the hinge region (S108P) to promote dimer stabilization. Unless indicated otherwise, all antibodies used in the following examples comprise a human IgG4 isotype.

Table 3 sets forth the nucleic acid (DNA) and amino acid (PEP) sequence identifiers of the heavy and light chains (HC and LC) of selected anti-ACVR1 antibodies of the invention.

TABLE 3

Sequence Identifiers for Heavy and Light Chains

| Antibody Designation | SEQ ID NO: | | | |
|---|---|---|---|---|
| | HC DNA | HC PEP | LC DNA | LC PEP |
| mAb27396 | 17 | 18 | 19 | 20 |
| mAb27241 | 37 | 38 | 39 | 40 |
| mAb27242 | 53 | 54 | 55 | 56 |
| mAb27243 | 67 | 68 | 69 | 70 |
| mAb27245 | 37 | 38 | 73 | 74 |
| mAb27247 | 91 | 92 | 93 | 94 |
| mAb27404 | 111 | 112 | 113 | 114 |
| mAb27405 | 123 | 124 | 125 | 126 |
| mAb27400 | 143 | 144 | 145 | 146 |
| mAb22124 | 161 | 162 | 163 | 164 |
| mAb22125 | 181 | 182 | 183 | 184 |
| mAb22168 | 198 | 199 | 200 | 201 |
| mAb29226 | 218 | 219 | 220 | 221 |
| mAb29233 | 236 | 237 | 238 | 239 |
| mAb29237 | 250 | 251 | 252 | 253 |
| mAb29256 | 268 | 269 | 270 | 271 |
| mAb29257 | 284 | 285 | 286 | 287 |
| mAb29261 | 295 | 296 | 297 | 298 |
| mAb29266 | 314 | 315 | 316 | 317 |
| mAb22115 | 334 | 335 | 336 | 337 |

Example 3: Antibody Binding to ACVR1 as Determined by Surface Plasmon Resonance

Experimental Procedure

Equilibrium dissociation constants ($K_D$) for ACVR1 binding to purified anti-ACVR1 monoclonal antibodies were determined using a real-time surface plasmon resonance biosensor (SPR-Biacore), Biacore 4000. All binding studies were performed in 10 mM HEPES, 150 mM NaCl, 3 mM EDTA, and 0.05% v/v surfactant Tween-20, pH 7.4 (HBS-ET) running buffer at 25° C. and 37° C. The Biacore CM5 sensor surface was first derivatized by amine coupling with a monoclonal mouse anti-human Fc antibody (GE, #BR-1008-39 or REGN2567) to capture anti-ACVR1 monoclonal antibodies. Different concentrations of ACVR1 reagents, human ACVR1 extracellular domain expressed with a C-terminal myc-myc-hexahistidine tag (hACVR1-MMH; SEQ ID NO: 338), mouse ACVR1 extracellular domain expressed with a C-terminal myc-myc-hexahistidine tag (mACVR1-MMH; SEQ ID NO: 340), human ACVR1 extracellular domain expressed with a C-terminal mouse IgG2a Fc tag (hACVR1-mFc; SEQ ID NO: 339), were first prepared in HBS-ET running buffer (900 nM-3.7 nM; serially diluted by 3-fold). ACVR1 reagents were then injected over anti-human Fc captured anti-ACVR1 monoclonal antibody surface for 2.5-3 minutes at a flow rate of 30 µL/minute, while the dissociation of monoclonal antibody bound ACVR1 reagent was monitored for 10-15 minutes in HBS-ET running buffer. Kinetic association rate constant ($k_a$) and dissociation rate constant ($k_d$) were determined by fitting the real-time sensorgrams to a 1:1 binding model using Scrubber 2.0c curve-fitting software. Binding dissociation equilibrium constants ($K_D$) and dissociative half-lives (t ½) were calculated from the kinetic rate constants as:

$$K_D(M) = \frac{kd}{ka}, \text{ and } t1/2(\min) = \frac{\ln(2)}{60 * kd}$$

Results

Binding kinetics parameters for different ACVR1 reagents to anti-ACVR1 monoclonal antibodies of the invention at 25° C. and 37° C. are shown in Table 4 through Table 9.

TABLE 4

Binding kinetics parameters of hACVR1-MMH binding to anti-ACVR1 monoclonal antibodies at 25° C.

| mAb captured | mAb Capture Level (RU) | 900 nM or 100 nM Ag Bound (RU) | $k_a$ (1/Ms) | $k_d$ (1/s) | $K_D$ (M) | $t_{1/2}$ (min) |
|---|---|---|---|---|---|---|
| mAb29257 | 350 + 4.6 | 47 | 6.18E+04 | 5.21E−04 | 8.43E−09 | 22 |
| mAb27396 | 349 + 4.5 | 23 | 2.56E+05 | 7.45E−02 | 2.91E−07 | 0.16 |
| mAb29226 | 344 + 3.4 | 57 | 1.13E+05 | 9.37E−04 | 8.27E−09 | 12 |
| MAB27405 | 366 + 2.2 | 37 | 6.99E+04 | 1.47E−03 | 2.10E−08 | 8 |
| H4H27247 | 349 + 2.8 | 52 | 1.15E+05 | 1.19E−03 | 1.04E−08 | 10 |
| mAb27404 | 366 + 1.1 | 46 | 9.92E+04 | 4.46E−04 | 4.49E−09 | 26 |
| mAb27242 | 363 + 1.9 | 63 | 8.68E+04 | 1.35E−04 | 1.56E−09 | 86 |
| mAb27243 | 353 + 2.8 | 51 | 5.41E+04 | 1.60E−04 | 2.96E−09 | 72 |
| mAb27245 | 364 + 3 | 35 | 2.58E+04 | 2.07E−04 | 8.01E−09 | 56 |
| mAb27241 | 346 + 2 | 34 | 1.89E+04 | 1.23E−04 | 6.52E−09 | 94 |
| mAb29266 | 351 + 3 | 44 | 6.21E+04 | 6.79E−03 | 1.09E−07 | 1.7 |
| mAb27400 | 352 + 3.4 | 2 | NB* | NB* | NB* | NB* |
| mAb22125 | 687 + 2.1 | 44 | 4.13E+05 | 4.20E−01 | 1.02E−06 | 0.03 |
| mAb22124 | 641 + 1.8 | 21 | 6.61E+05 | 1.30E+00 | 1.97E−06 | 0.01 |
| mAb22168 | 646 + 0.9 | 36 | 7.98E+05 | 8.43E−01 | 1.06E−06 | 0.01 |
| mAb29233 | 370 + 1.1 | 1 | NB* | NB* | NB* | NB* |
| mAb29237 | 305 + 3.2 | 0 | NB* | NB* | NB* | NB* |
| mAb29256 | 332 + 2.3 | −2 | NB* | NB* | NB* | NB* |
| mAb29261 | 332 + 3.6 | 0 | NB* | NB* | NB* | NB* |
| mAb22115 | 630 + 1.5 | 93 | 3.34E+04 | 4.85E−03 | 1.45E−07 | 2.4 |
| Isotype Control mAb | 637 + 0.5 | 1 | NB* | NB* | NB* | NB* |

*NB indicates that no binding was observed under the current experimental conditions.

TABLE 5

Binding kinetics parameters of hACVR1-MMH binding to anti-ACVR1 monoclonal antibodies at 37° C.

| mAb captured | mAb Capture Level (RU) | 900 nM or 100 nM Ag Bound (RU) | $k_a$ (1/Ms) | $k_d$ (1/s) | $K_D$ (M) | $t_{1/2}$ (min) |
|---|---|---|---|---|---|---|
| mAb29257 | 431 + 1.5 | 64 | 1.53E+05 | 3.26E−03 | 2.14E−08 | 3.5 |
| mAb27396 | 451 + 4.6 | 22 | 4.96E+05 | 1.80E−01 | 3.62E−07 | 0.06 |
| mAb29226 | 397 + 1.8 | 68 | 1.82E+05 | 4.56E−03 | 2.50E−08 | 2.5 |
| mAb27405 | 440 + 1.3 | 52 | 1.19E+05 | 5.28E−03 | 4.44E−08 | 2.2 |
| mAb27247 | 404 + 2.4 | 67 | 2.09E+05 | 4.04E−03 | 1.93E−08 | 2.9 |
| mAb27404 | 453 + 4 | 67 | 2.40E+05 | 1.83E−03 | 7.63E−09 | 6 |
| mAb27242 | 441 + 1.1 | 82 | 1.44E+05 | 8.30E−04 | 5.77E−09 | 14 |
| mAb27243 | 412 + 1.8 | 71 | 1.23E+05 | 1.16E−03 | 9.41E−09 | 10 |
| mAb27245 | 448 + 2.2 | 66 | 5.39E+04 | 1.73E−03 | 3.22E−08 | 7 |
| mAb27241 | 430 + 0.9 | 66 | 4.32E+04 | 8.52E−04 | 1.97E−08 | 14 |
| mAb29266 | 418 + 3.8 | 38 | 1.56E+05 | 2.99E−02 | 1.91E−07 | 0.39 |
| mAb27400 | 430 + 2.9 | 15 | 9.71E+03 | 4.76E−04 | 4.90E−08 | 24 |
| mAb22125 | 892 + 3.1 | 25 | IC # | IC # | IC # | IC # |
| mAb22124 | 831 + 1.3 | 14 | IC # | IC # | IC # | IC # |
| mAb22168P | 842 + 0.8 | 27 | IC # | IC # | IC # | IC # |
| mAb29233 | 453 + 7.4 | 3 | NB* | NB* | NB* | NB* |
| mAb29237 | 330 + 23 | 1 | NB* | NB* | NB* | NB* |
| mAb29256 | 371 + 5.1 | 0 | NB* | NB* | NB* | NB* |

TABLE 5-continued

Binding kinetics parameters of hACVR1-MMH binding to anti-ACVR1 monoclonal antibodies at 37° C.

| mAb captured | mAb Capture Level (RU) | 900 nM or 100 nM Ag Bound (RU) | $k_a$ (1/Ms) | $k_d$ (1/s) | $K_D$ (M) | $t_{1/2}$ (min) |
|---|---|---|---|---|---|---|
| mAb29261 | 405 + 3.9 | 5 | NB* | NB* | NB* | NB* |
| mAb22115 | 835 + 1.9 | 86 | 7.04E+04 | 3.08E−02 | 4.38E−07 | 0.37 |
| Isotype Control mAb | 879 + 1.3 | 0 | NB* | NB* | NB* | NB* |

*NB indicates that no binding was observed under the current experimental conditions
IC indicates that the binding data was inconclusive

TABLE 6

Binding kinetics parameters of hACVR1-mFc binding to anti-ACVR1 monoclonal antibodies at 25° C.

| mAb captured | mAb Capture Level (RU) | 100 nM Ag Bound (RU) | $k_a$ (1/Ms) | $k_d$ (1/s) | $K_D$ (M) | $t_{1/2}$ (min) |
|---|---|---|---|---|---|---|
| mAb29257 | 350 + 2 | 157 | 1.29E+05 | 1.21E−04 | 9.36E−10 | 95 |
| mAb27396 | 351 + 1.7 | 170 | 3.24E+05 | 4.93E−04 | 1.52E−09 | 23 |
| mAb29226 | 341 + 0.9 | 188 | 2.10E+05 | 1.61E−04 | 7.67E−10 | 72 |
| mAb27405 | 363 + 1.9 | 142 | 1.06E+05 | 2.01E−04 | 1.90E−09 | 57 |
| mAb27247 | 346 + 0.7 | 186 | 2.29E+05 | 1.80E−04 | 7.87E−10 | 64 |
| mAb27404 | 363 + 1.1 | 160 | 1.98E+05 | 8.76E−05 | 4.44E−10 | 132 |
| mAb27242 | 362 + 1.5 | 199 | 1.44E+05 | 2.90E−05 | 2.02E−10 | 398 |
| mAb27243 | 349 + 4.7 | 170 | 1.13E+05 | 3.63E−05 | 3.18E−10 | 318 |
| mAb27245 | 362 + 2 | 145 | 3.81E+04 | 5.06E−05 | 1.34E−09 | 228 |
| mAb27241 | 345 + 2.1 | 135 | 3.49E+04 | 3.20E−05 | 9.18E−10 | 361 |
| mAb29266 | 353 + 1.7 | 178 | 1.14E+05 | 6.20E−04 | 5.43E−09 | 19 |
| mAb27400 | 348 + 1.4 | 24 | 1.19E+04 | 1.42E−04 | 1.19E−08 | 81 |
| mAb22125 | 685 + 3.2 | 268 | 6.52E+05 | 8.02E−03 | 1.23E−08 | 1.4 |
| mAb22124 | 637 + 1.2 | 172 | 7.39E+05 | 4.09E−02 | 5.54E−08 | 0.28 |
| mAb22168 | 645 + 0.7 | 264 | 8.37E+05 | 9.28E−03 | 1.11E−08 | 1.2 |
| mAb29233 | 368 + 0.6 | 2 | NB* | NB* | NB* | NB* |
| mAb29237 | 279 + 2.9 | −2 | NB* | NB* | NB* | NB* |
| mAb29256 | 315 + 1.9 | −1 | NB* | NB* | NB* | NB* |
| mAb29261 | 334 + 2.4 | 0 | NB* | NB* | NB* | NB* |
| mAb22115 | 629 + 1.1 | 264 | 6.69E+04 | 7.65E−04 | 1.14E−08 | 15 |
| Isotype Control mAb | 638 + 0.9 | −2 | NB* | NB* | NB* | NB* |

*NB indicates that no binding was observed under the current experimental conditions.

TABLE 7

Binding kinetics parameters of hACVR1-mFc binding to anti-ACVR1 monoclonal antibodies at 37° C.

| mAb captured | mAb Capture Level (RU) | 100 nM Ag Bound (RU) | $k_a$ (1/Ms) | $k_d$ (1/s) | $K_D$ (M) | $t_{1/2}$ (min) |
|---|---|---|---|---|---|---|
| mAb29257 | 425 + 1.9 | 201 | 3.14E+05 | 4.95E−04 | 1.58E−09 | 23 |
| mAb27396 | 448 + 3.5 | 197 | 4.54E+05 | 1.96E−03 | 4.31E−09 | 6 |
| mAb29226 | 387 + 1.5 | 212 | 3.40E+05 | 5.21E−04 | 1.53E−09 | 22 |
| mAb27405 | 434 + 1.9 | 185 | 2.33E+05 | 7.42E−04 | 3.18E−09 | 16 |
| mAb27247 | 393 + 2.3 | 219 | 3.71E+05 | 5.15E−04 | 1.39E−09 | 22 |
| mAb27404 | 449 + 1.2 | 216 | 3.03E+05 | 3.38E−04 | 1.11E−09 | 34 |
| mAb27242 | 437 + 1 | 250 | 2.82E+05 | 1.89E−04 | 6.69E−10 | 61 |
| mAb27243 | 409 + 1.3 | 228 | 2.36E+05 | 2.59E−04 | 1.10E−09 | 45 |
| mAb27245 | 444 + 2 | 222 | 9.17E+04 | 3.35E−04 | 3.65E−09 | 34 |
| mAb27241 | 426 + 1.7 | 216 | 8.22E+04 | 2.01E−04 | 2.44E−09 | 57 |
| mAb29266 | 411 + 2.8 | 205 | 2.35E+05 | 9.11E−04 | 3.88E−09 | 13 |
| mAb27400 | 418 + 2.5 | 68 | 1.27E+04 | 1.63E−04 | 1.28E−08 | 71 |
| mAb22125 | 885 + 2.4 | 243 | 7.29E+05 | 5.77E−02 | 7.92E−08 | 0.20 |
| mAb22124 | 825 + 2.7 | 158 | 8.23E+05 | 1.19E−01 | 1.45E−07 | 0.10 |
| mAb22168 | 838 + 0.8 | 278 | 8.12E+05 | 4.58E−02 | 5.64E−08 | 0.25 |
| mAb29233 | 445 + 1 | 3 | NB* | NB* | NB* | NB* |
| mAb29237 | 263 + 6 | 5 | NB* | NB* | NB* | NB* |

TABLE 7-continued

Binding kinetics parameters of hACVR1-mFc binding to anti-ACVR1 monoclonal antibodies at 37° C.

| mAb captured | mAb Capture Level (RU) | 100 nM Ag Bound (RU) | $k_a$ (1/Ms) | $k_d$ (1/s) | $K_D$ (M) | $t_{1/2}$ (min) |
|---|---|---|---|---|---|---|
| mAb29256 | 350 + 2.6 | 3 | NB* | NB* | NB* | NB* |
| mAb29261 | 394 + 5.4 | 11 | IC # | IC # | IC # | IC # |
| mAb22115 | 830 + 1.5 | 317 | 8.33E+04 | 2.50E−03 | 3.01E−08 | 4.6 |
| Isotype Control mAb | 875 + 1.1 | −1 | NB* | NB* | NB* | NB* |

*NB indicates that no binding was observed under the current experimental conditions.
IC indicates that the binding data was inconclusive

TABLE 8

Binding kinetics parameters of mACVR1-mmh binding to anti-ACVR1 monoclonal antibodies at 25° C.

| mAb captured | mAb Capture Level (RU) | 900 nM or 100 nM Ag Bound (RU) | $k_a$ (1/Ms) | $k_d$ (1/s) | $K_D$ (M) | $t_{1/2}$ (min) |
|---|---|---|---|---|---|---|
| mAb29257 | 353 + 1.3 | −2 | NB* | NB* | NB* | NB* |
| mAb27396 | 353 + 1.4 | 1 | NB* | NB* | NB* | NB* |
| mAb29226 | 342 + 0.5 | 2 | NB* | NB | NB* | NB* |
| mAb27405 | 364 + 1.2 | 0 | NB* | NB* | NB* | NB* |
| mAb27247 | 347 + 0.8 | 3 | NB* | NB* | NB* | NB* |
| mAb27404 | 364 + 1.1 | 1 | NB* | NB* | NB* | NB* |
| mAb27242 | 362 + 1.8 | 6 | 2.38E+05 | 1.44E−01 | 6.02E−07 | 0.08 |
| mAb27243 | 349 + 2 | 6 | 1.48E+05 | 1.31E−01 | 8.83E−07 | 0.09 |
| mAb27245 | 363 + 1 | 1 | NB* | NB* | NB* | NB* |
| mAb27241 | 347 + 0.8 | 1 | NB* | NB* | NB* | NB* |
| mAb29266 | 353 + 1.4 | 5 | IC # | IC # | IC # | IC # |
| mAb27400 | 349 + 1.4 | −3 | NB* | NB* | NB* | NB* |
| mAb22125 | 686 + 2.8 | 41 | 6.88E+05 | 5.75E−01 | 8.36E−07 | 0.02 |
| mAb22124 | 640 + 1 | 18 | 7.08E+05 | 1.50E+00 | 2.13E−06 | 0.01 |
| mAb22168 | 647 + 0.3 | 33 | 1.25E+06 | 1.08E+00 | 8.65E−07 | 0.01 |
| mAb29233 | 369 + 0.7 | 1 | NB* | NB* | NB* | NB* |
| mAb29237 | 292 + 5.1 | −3 | NB* | NB* | NB* | NB* |
| mAb29256 | 323 + 3.3 | −3 | NB* | NB* | NB* | NB* |
| mAb29261 | 338 + 1.4 | −1 | NB* | NB* | NB* | NB* |
| mAb22115 | 629 + 1.2 | 94 | 2.80E+04 | 4.78E−03 | 1.71E−07 | 2.4 |
| Isotype Control mAb | 638 + 0.4 | −2 | NB* | NB* | NB* | NB* |

*NB indicates that no binding was observed under the current experimental conditions.
IC indicates that the binding data was inconclusive.

TABLE 9

Binding kinetics parameters of mACVR1-mmh binding to anti-ACVR1 monoclonal antibodies at 37° C.

| mAb captured | mAb Capture Level (RU) | 900 nM or 100 nM Ag Bound (RU) | $k_a$ (1/Ms) | $k_d$ (1/s) | $K_D$ (M) | $t_{1/2}$ (min) |
|---|---|---|---|---|---|---|
| mAb29257 | 430 + 3 | 2 | NB* | NB* | NB* | NB* |
| mAb27396 | 451 + 4.4 | 4 | NB* | NB* | NB* | NB* |
| mAb29226 | 392 + 1.9 | 2 | NB* | NB* | NB* | NB* |
| mAb27405 | 438 + 1.1 | 2 | NB* | NB* | NB* | NB* |
| mAb27247 | 398 + 1.4 | 4 | NB* | NB* | NB* | NB* |
| mAb27404 | 452 + 1.9 | 4 | NB* | NB* | NB* | NB* |
| mAb27242 | 439 + 1.2 | 4 | NB* | NB* | NB* | NB* |
| mAb27243 | 410 + 1.8 | 5 | IC # | IC # | IC # | IC # |
| mAb27245 | 446 + 2.6 | 2 | NB* | NB* | NB* | NB* |
| mAb27241 | 428 + 1.1 | 2 | NB* | NB* | NB* | NB* |
| mAb29266 | 407 + 17.4 | 5 | NB* | NB* | NB* | NB* |
| mAb27400 | 423 + 3 | 2 | NB* | NB* | NB* | NB* |
| mAb22125 | 887 + 1.6 | 23 | IC # | IC # | IC # | IC # |
| mAb22124 | 828 + 1.1 | 14 | IC # | IC # | IC # | IC # |

TABLE 9-continued

Binding kinetics parameters of mACVR1-mmh binding to anti-ACVR1 monoclonal antibodies at 37° C.

| mAb captured | mAb Capture Level (RU) | 900 nM or 100 nM Ag Bound (RU) | $k_a$ (1/Ms) | $k_d$ (1/s) | $K_D$ (M) | $t_{1/2}$ (min) |
|---|---|---|---|---|---|---|
| mAb22168 | 840 + 0.8 | 23 | IC # | IC # | IC # | IC # |
| mAb29233 | 447 + 1.1 | 1 | NB* | NB* | NB* | NB* |
| mAb29237 | 287 + 9 | −1 | NB* | NB* | NB* | NB* |
| mAb29256 | 358 + 3.4 | 0 | NB* | NB* | NB* | NB* |
| mAb29261 | 399 + 5 | 2 | NB* | NB* | NB* | NB* |
| mAb22115 | 834 + 1.4 | 85 | 5.89E+04 | 2.97E−02 | 5.04E−07 | 0.39 |
| Isotype Control mAb | 877 + 1.8 | 0 | NB* | NB* | NB* | NB* |

*NB indicates that no binding was observed under the current experimental conditions.
IC indicates that the binding data was inconclusive At 25° C., anti-ACVR1 monoclonal antibodies that bound to hACVR1-MMH had $K_D$ values ranging from 1.56 nM to 1.97 μM, as shown in Table 4. At 37° C., anti-ACVR1 monoclonal antibodies that bound to hACVR1-MMH had $K_D$ values ranging from 5.77 nM to 438 nM, as shown in Table 5.

At 25° C., anti-ACVR1 monoclonal antibodies that bound to hACVR1-mFc had $K_D$ values ranging from 0.20 nM to 55.4 nM, as shown in Table 6. At 37° C., anti-ACVR1 monoclonal antibodies that bound to hACVR1-mFc had $K_D$ values ranging from 0.67 nM to 145 nM, as shown in Table 7. At 25° C., anti-ACVR1 monoclonal antibodies that bound to mACVR1-MMH had $K_D$ values ranging from 171 nM to 2.13 μM, as shown in Table 8. At 37° C., only one anti-ACVR1 monoclonal antibody bound to mACVR1-MMH with a $K_D$ value of 504 nM, as shown in Table 9.

Example 4: Cross-Competition Between Different Anti-ACVR1 Monoclonal Antibodies

Experimental Procedure

Binding competition within a panel of anti-ACVR1 monoclonal antibodies was determined using a real time, label-free bio-layer interferometry assay on the Octet HTX biosensor platform (Pall ForteBio Corp.). The entire experiment was performed at 25° C. in 10 mM HEPES, 150 mM NaCl, 3 mM EDTA, and 0.05% v/v Surfactant Tween-20, 1 mg/mL BSA, pH7.4 (HBS-EBT) buffer with the plate shaking at the speed of 1000 rpm. To assess whether two antibodies are able to compete with one another for binding to their respective epitopes, human ACVR1 extracellular domain expressed with a C-terminal myc-myc-hexahistidine tag (hACVR1-MMH; SEQ ID NO: 338) was first captured by dipping anti-His antibody coated Octet biosensor tips (Fortebio Inc, #18-5079) by submerging the biosensor tips in wells containing 10 μg/mL hACVR1-MMH for 40 seconds. The antigen captured biosensor tips were then saturated with the first anti-ACVR1 monoclonal antibody (referred to as mAb-1) by dipping into wells containing 50 μg/mL solution of mAb-1 for 4 minutes. The biosensor tips were then dipped into wells containing 50 μg/mL solution of second anti-ACVR1 monoclonal antibody (referred to as mAb-2) for 3 minutes. The biosensor tips were washed in HBS-EBT buffer between every step of the experiment. The real-time binding response was monitored over the entire duration of the experiment and the binding response at the end of every step was recorded. The response of mAb-2 binding to hACVR1-MMH complexed with mAb-1 was compared and competitive/non-competitive behavior of different anti-ACVR1 monoclonal antibodies was determined as shown in Table 10.

Results

TABLE 10

Cross-competition between anti-ACVR1 monoclonal antibodies

| mAb-1 | mAb-2 competing with mAb-1 |
|---|---|
| mAb29257 | mAb27396 |
|  | mAb27242 |
|  | mAb27243 |
|  | mAb27241 |
|  | mAb27245 |
|  | mAb27247 |
|  | mAb27404 |
|  | mAb27405 |
| mAb27396 | mAb29257 |
|  | mAb27242 |
|  | mAb27243 |
|  | mAb27241 |
|  | mAb27245 |
|  | mAb27247 |
|  | mAb27404 |
|  | mAb27405 |
| mAb27242 | mAb29257 |
|  | mAb27396 |
|  | mAb27243 |
|  | mAb27241 |
|  | mAb27245 |
|  | mAb27247 |
|  | mAb27404 |
|  | mAb27405 |
| mAb27243 | mAb29257 |
|  | mAb27396 |
|  | mAb27242 |
|  | mAb27241 |
|  | mAb27245 |
|  | mAb27247 |
|  | mAb27404 |
|  | mAb27405 |
| mAb27241 | mAb29257 |
|  | mAb27396 |
|  | mAb27242 |
|  | mAb27243 |
|  | mAb27245 |
|  | mAb27247 |
|  | mAb27404 |
|  | mAb27405 |
| mAb27245 | mAb29257 |
|  | mAb27396 |
|  | mAb27242 |
|  | mAb27243 |

TABLE 10-continued

Cross-competition between anti-ACVR1 monoclonal antibodies

| mAb-1 | mAb-2 competing with mAb-1 |
|---|---|
| mAb27247 | mAb27241 |
|  | mAb27247 |
|  | mAb27404 |
|  | mAb27405 |
|  | mAb29257 |
|  | mAb27396 |
|  | mAb27242 |
|  | mAb27243 |
|  | mAb27241 |
|  | mAb27245 |
|  | mAb27404 |
|  | mAb27405 |
| mAb27404 | mAb29257 |
|  | mAb27396 |
|  | mAb27242 |
|  | mAb27243 |
|  | mAb27241 |
|  | mAb27245 |
|  | mAb27247 |
|  | mAb27405 |
| mAb27405 | mAb29257 |
|  | mAb27396 |
|  | mAb27242 |
|  | mAb27243 |
|  | mAb27241 |
|  | mAb27245 |
|  | mAb27247 |
|  | mAb27404 |

Table 10 shows the cross-competition between selected anti-ACVR1 antibodies.

Example 5: Cell Binding by Flow Cytometry with HEK293/hACVR1-Wt and HEK293/hACVR1-R206H Cells In order to assess cell binding by anti-hACVR1 antibodies two cell lines were generated to stably over-express full length hACVR1 in HEK293 cells along with a BMP-response element fused to firefly luciferase reporter (BRE-Luc). One cell line contained the wild type version of hACVR1 (amino acids 1-509 of accession #Q04771), and was named HEK293/BRE-luc/hACVR1-wild type. It is hereafter referred to as HEK293/hACVR1-wt. The other line contained hACVR1 (R206H). A single clone of this cell line was isolated, and the resulting cell line was named HEK293/BRE-luc/hACVR1-R206H-clone H2. It is hereafter referred to as HEK293/hACVR1-R206H.

To assess binding of the anti-ACVR1 antibodies of the invention to the receptor expressed on the cell surface, either 66.6 nM or 70 nM of the antibodies were incubated with $0.5 \times 10^6$ cells/well at 4° C. for 30 minutes in PBS (without calcium and magnesium) containing 2% FBS. After incubation with primary antibodies, the cells were stained with 3.2 μg/mL of Alexa Fluor®-647 conjugated secondary antibody (Jackson ImmunoResearch Laboratories Inc., anti-human #109-607-003) at 4° C. for 25 or 30 minutes. Cells were fixed using BD CytoFix™ (Becton Dickinson, #554655) and analyzed on either Hypercyt® or IQue® Flow Cytometers (Intellicyt®). Unstained and secondary antibody alone controls were also tested for all cell lines. The results were analyzed using ForeCyt® (IntelliCyt®) software to determine the geometric means of fluorescence for viable cells and binding ratios were calculated by normalizing the geometric mean value of the test condition by the geometric mean value of the corresponding unstained cells.

TABLE 11

Binding of anti-hACVR1 antibodies to HEK293/BRE-luc/hACVR1 cells

| | MFI - Normalized to Unstained Control | | | | |
|---|---|---|---|---|---|
| | 66.6 nM antibody | | | 70 nM antibody | |
| mAb PID | HEK293 Parental | HEK293/ hACVR1-wt | HEK293/ hACVR1-R206H | HEK293 Parental | HEK293/ hACVR1-R206H |
| mAb22115 | 6 | 4 | 4 | Not Tested | Not Tested |
| mAb22124 | 2 | 41 | 116 | Not Tested | Not Tested |
| mAb22125 | 1 | 183 | 235 | Not Tested | Not Tested |
| mAb22168 | 1 | 116 | 213 | Not Tested | Not Tested |
| mAb29226 | Not Tested | Not Tested | Not Tested | 23 | 1900 |
| mAb29233 | Not Tested | Not Tested | Not Tested | 3 | 5 |
| mAb29237 | Not Tested | Not Tested | Not Tested | 9 | 10 |
| mAb29256P | Not Tested | Not Tested | Not Tested | 3 | 3 |
| mAb29257 | Not Tested | Not Tested | Not Tested | 26 | 1662 |
| mAb29261 | Not Tested | Not Tested | Not Tested | 2 | 2 |
| mAb29266 | Not Tested | Not Tested | Not Tested | 13 | 1642 |
| mAb27396 | Not Tested | Not Tested | Not Tested | 2 | 954 |
| mAb27241 | Not Tested | Not Tested | Not Tested | 19 | 1165 |
| mAb27242 | Not Tested | Not Tested | Not Tested | 23 | 1734 |
| mAb27243 | Not Tested | Not Tested | Not Tested | 18 | 1570 |
| mAb27245 | Not Tested | Not Tested | Not Tested | 21 | 1662 |
| mAb27247 | Not Tested | Not Tested | Not Tested | 7 | 1659 |
| mAb27404 | Not Tested | Not Tested | Not Tested | 18 | 1872 |

TABLE 11-continued

Binding of anti-hACVR1 antibodies to HEK293/BRE-luc/hACVR1 cells

| | MFI - Normalized to Unstained Control | | | | |
|---|---|---|---|---|---|
| | 66.6 nM antibody | | | 70 nM antibody | |
| mAb PID | HEK293 Parental | HEK293/ hACVR1-wt | HEK293/ hACVR1-R206H | HEK293 Parental | HEK293/ hACVR1-R206H |
| mAb27405 | Not Tested | Not Tested | Not Tested | 11 | 1563 |
| mAb27400 | Not Tested | Not Tested | Not Tested | 7 | 840 |
| hIgG4 Isotype Control | 1 | 3 | 1 | 1 | 3 |
| Anti-Human 2" alone | 1 | 1 | 1 | 1 | 1 |

As shown in Table 11, four of the 20 anti-hACVR1 antibodies of the invention showed binding to HEK293/hACVR1-wt cells with binding ratios ranging from 4 to 183-fold. All twenty anti-hACVR1 antibodies of the invention were tested in binding to HEK293/hACVR1-R206H cells and they showed binding to cells with binding ratios ranging from 2 to 1900-fold. The anti-hACVR1 antibodies of the invention demonstrated binding to the HEK293 parental cells, with binding ratios 1 to 26-fold. The isotype control antibodies and secondary antibodies alone samples demonstrated binding ratios ranging from 1 to 3-fold.

Example 6: Functional Inhibition of ACVR1 in Cell-Based Bioassay with HEK293/BRE-Luc/hACVR1-R206H-Clone H2 Cells, Activated by hBMP7 or hActivin A Activin A receptor type I, ACVR1 (also known as ActRI, ACVR1A, or Alk2), is a single-pass transmembrane receptor, and a member of the type I BMP receptor of the TGF-β receptor super family. Upon ligand binding, ACVR1 together with a type II receptor initiates a downstream signaling cascade leading to activation of receptor specific R-SMAD protein (SMAD1, SMAD5, or SMAD8) and collaborating SMAD, SMAD4, and leads to transcriptional regulation of genes (Massagué J, TGF-beta Signal Transduction, Annu. Rev. Biochem. 1998. 67:753-91, PMID: 9759503; Massague et al. Smad transcription factors, Genes Dev. 2005 19: 2783-2810, PMID: 16322555). In order to assess anti-ACVR1 antibody inhibition of ACVR1 (R206H), the mutation found in FOP (Shore et al., Nat Genet. 2006 May; 38(5):525-7. Epub 2006 Apr. 23. PMID: 16642017), a bioassay was established in HEK293 cells (human embryonic kidney, ATCC). HEK293 cells endogenously express ACVR1, the necessary Type II receptors, SMAD proteins, and other components that form a functional BMP signaling pathway. To drive the signaling through ACVR1, a cell line was generated to stably overexpress full length human ACVR1 (amino acids 1-509, R206H, of accession #Q04771), along with a BMP-response element fused to firefly luciferase reporter (BRE-Luc). A single clone of the cell line was isolated, and the resulting cell line was named HEK293/BRE-luc/hACVR1-R206H-clone H2. It is hereafter referred to as HEK293/BRE-luc/hACVR1-R206H.

For the bioassay, HEK293/BRE-luc/hACVR1-R206H cells were plated at 10,000 cells/well in a 96-well plate in assay buffer (DMEM High Glucose+10% FBS+Pen/Strep/L-Glutamine) and incubated for 5 hours at 37° C. in 5% $CO_2$. Following the 5 hour incubation, anti-ACVR1 antibodies or an isotype control antibody that were serially diluted in assay buffer from either 300 nM to 73.2 pM or 173.3 nM to 42.3 pM (plus a sample containing buffer alone without test molecule) were added to the cells and incubated at 25° C. for 30 minutes. After 30 minutes, either 3 nM human Activin A (hActivin A, R&D System 338-AC), 2 nM human Bone Morphogenetic Protein 7 (hBMP7, R&D System 354-BP/C) or 3 nM hBMP7 were added to cells. To obtain a dose dependent activation by the ligands, hActivin A or hBMP7 were serially diluted from either 200 nM to 3.4 pM or 100 nM to 1.7 pM in assay buffer (plus a sample containing buffer alone without test molecule) and added to cells not treated with antibodies. After overnight incubation at 37° C. in 5% CO2, luciferase activity was measured with OneGlo™ reagent (Promega, #E6031) and VictorX or Envision plate readers (Perkin Elmer). The results were analyzed using nonlinear regression (4-parameter logistics) with Prism software (GraphPad) to obtain $EC_{50}$ and $IC_{50}$ values. The percentage of inhibition was calculated with the RLU values by using the following equation:

$$\% \text{ Inhibition} = 100 \times \frac{RLU_{Baseline} - RLU_{Inhibition}}{RLU_{Baseline} - RLU_{Background}}$$

In this equation "$RLU_{Baseline}$" is the luminescence value from the cells treated constant amount of ligand (hActivin A or hBMP7) without antibodies, "$RLU_{inhibition}$" is the luminescence value with maximum concentration of a particular antibody with a particular concentration of ligand, and "$RLU_{Background}$" is the luminescence value from cells without any ligands or antibodies.

Twenty anti-human ACVR1 antibodies of the invention were tested for their ability to inhibit activation of HEK293/BRE-luc/hACVR1-R206H cells. Results are shown in Table 12.

TABLE 12

Inhibition of anti-hACVR1 antibodies in presence of hACVR1 ligands in HEK293/BRE-luc/hACVR1-R206H cells

| Ligand EC$_{50}$ [M] | hActivin A | | hBMP7 | | | |
|---|---|---|---|---|---|---|
| Constant | 3.33E−10 | | 2.97E−10 | | 1.22E−09 | |
| Ligand | 3 nM hActivin A | | 3 nM hBMP7 | | 2 nM hBMP7 | |
| mAb PID | IC$_{50}$ [M] | % Inhibition | IC$_{50}$ [M] | % Inhibition | IC$_{50}$ [M] | % Inhibition |
| mAb22115 | No Inhibition | No Inhibition | No Inhibition | No Inhibition | Not Tested | Not Tested |
| mAb22124 | 1.8E−08 | 51 | >1.0E−07 | 46 | Not Tested | Not Tested |
| mAb22125 | 1.9E−08 | 78 | 1.6E−08 | 51 | Not Tested | Not Tested |
| mAb22168 | 2.3E−08 | 75 | >1.0E−07 | 52 | Not Tested | Not Tested |
| mAb29226 | Not Tested | Not Tested | Not Tested | Not Tested | 7.3E−10 | 70 |
| mAb29233 | Not Tested | Not Tested | Not Tested | Not Tested | No Inhibition | No Inhibition |
| mAb29237 | Not Tested | Not Tested | Not Tested | Not Tested | No Inhibition | No Inhibition |
| mAb29256 | Not Tested | Not Tested | Not Tested | Not Tested | No Inhibition | No Inhibition |
| mAb29257 | Not Tested | Not Tested | Not Tested | Not Tested | 1.4E−10 | 62 |
| mAb29261 | Not Tested | Not Tested | Not Tested | Not Tested | No Inhibition | No Inhibition |
| mAb29266 | Not Tested | Not Tested | Not Tested | Not Tested | 1.9E−09 | 93 |
| mAb27396 | Not Tested | Not Tested | Not Tested | Not Tested | 5.8E−10 | 90 |
| mAb27241 | Not Tested | Not Tested | Not Tested | Not Tested | 1.8E−09 | 110 |
| mAb27242 | Not Tested | Not Tested | Not Tested | Not Tested | 1.2E−09 | 109 |
| mAb27243 | Not Tested | Not Tested | Not Tested | Not Tested | 1.3E−09 | 112 |
| mAb27245 | Not Tested | Not Tested | Not Tested | Not Tested | 1.5E−09 | 110 |
| mAb27247 | Not Tested | Not Tested | Not Tested | Not Tested | 7.6E−10 | 111 |
| mAb27404 | Not Tested | Not Tested | Not Tested | Not Tested | 8.8E−10 | 109 |
| mAb27405 | Not Tested | Not Tested | Not Tested | Not Tested | 7.6E−10 | 107 |
| mAb27400 | Not Tested | Not Tested | Not Tested | Not Tested | 2.0E−09 | 96 |
| hIgG4 Isotype (REGN1945) | No Inhibition | No Inhibition | No Inhibition | No Inhibition | No Inhibition | No Inhibition |

As shown in Table 12, ten of the antibodies of the invention, showed at least 90% inhibition of 2 nM hBMP7, with 10 50 values for the inhibiting antibodies ranging from 580 pM to 2.0 nM. Five of the antibodies of the invention, showed between 46% and 78% inhibition of either 3 nM hActivin A, 2 nM or 3 nM hBMP7, with 10 50 values for the inhibiting antibodies ranging from 140 pM to >100 nM. Five antibodies of the invention did not show inhibition of any of ligands tested. An isotype control antibody did not demonstrate any measurable inhibition of HEK293/BRE-luc/hACVR1-R206H cells activated by either hActivin A or hBMP7. The ligands activated HEK293/BRE-luc/hACVR1-R206H cells with E0 50 values of 297 pM or 1.22 nM for hBMP7, and 333 pM for hActivin A.

Example 7: Anti-ACVR1 Antibody Testing In Vivo; Serum Analysis of Acvr1$^{hu/hu}$ Mice for Hepcidin and Iron Levels Hepcidin and iron levels were tested in Acvr1$^{hu/hu}$ mice after treatment with anti-ACVR1 antibodies mAb27242; mAb27243; mAb27247; and hIgG4 isotype control antibody (REGN1945).

BMP6 mediated activation of ACVR1 directly activates transcription of Hamp, the gene that encodes hepcidin. Hepcidin is a negative regulator of iron levels by causing internalization of ferroportin (slc40a1), the only known iron exporter. Inhibition of the BMP6-ACVR1 signaling cascade leads to decreased Hamp transcription, resulting in decreased circulating levels of hepcidin. A reduction of circulating hepcidin results in increased ferroportin levels, which allows increased uptake of iron from the small intestines, thereby increasing circulating iron levels.

Therefore, to determine the effects of anti-ACVR1 antibodies of the invention on serum hepcidin and iron, an in vivo experiment in mice was performed. For the experiment, mice expressing human ACVR1 in place of the mouse allele (referred to as Acvr1$^{hu/hu}$ mice) were utilized. Forty-two female Acvr1$^{hu/hu}$ mice (12-15 weeks old) were dosed with 10 mg/kg of either isotype control, mAb27242, mAb27243 or mAb27247 on Days 1 and 5 of the experiment. Mice were sacrificed for serum collection at Day 8. Serum was analyzed for Hepcidin protein levels using the Hepcidin-Murine Complete ELISA (Intrinsic Lifesciences, Cat #HMC-001) and iron levels using a QuantiChrom Iron Assay Kit (BioAssay Systems, Cat #DIFE-250). Results are shown in Table 13.

TABLE 13

Serum Hepcidin and Serum Iron levels in Acvr1$^{hu/hu}$ mice

| | Serum Hepcidin | | Serum Iron | |
|---|---|---|---|---|
| Antibody tested | Mean | Standard deviation | Mean | Standard deviation |
| Isotype control | 288.3 | 71.92 | 206.6 | 64.74 |
| mAb27242 | 140.0 | 78.86 | 462.1 | 70.77 |
| mAb27243 | 123.7 | 34.58 | 513.1 | 140.0 |
| mAb27247 | 220.1 | 58.66 | 332.1 | 159.7 |

As shown in Table 13, ACVR1 antibodies of the invention, mAb27242 and mAb27243, decreased serum hepcidin and increased serum iron levels in Acvr1$^{hu/hu}$ mice, whereas mAb27247 showed no effect on serum hepcidin or serum iron levels in Acvr1h 1 mice. This indicates that mAb27242 and mAb27243 can inhibit wild type ACVR1 signaling.

Example 8: Anti-ACVR1 Antibody Testing In Vivo; Post-Traumatic Heterotopic Ossification Model The present study evaluated effects of an anti-ACVR1 antibody of the invention mAb27242 and an anti-activin A antibody in an in vivo post-traumatic HO model in mice.

Heterotopic ossification (HO), the formation of ectopic bone in soft tissues, occurs in two primary forms: post-traumatic HO (tHO) typically found in patients who have experienced musculoskeletal or neurogenic injury and the genetically driven fibrodysplasia ossificans progressive (FOP) downstream to a specific point mutation known as R206H in the ACVR1 receptor. Both diseases undergo a process of endochondral ossification in the formation of ectopic bone.

The principle management for HO remains surgical excision that is often complicated by recurrence, nearly universally so in FOP. While both post-traumatic and FOP varieties of HO have been demonstrated to reflect an aberrancy in inflammation that triggers endochondral ossification, the antecedent signals for this convergent programming seem distinct within the existing literature. In both varieties, pathology appears dependent on the signaling from a specific subset of receptors sensitive to ligands of the transforming growth factor beta (TGFβ) superfamily including Alk2/ACVR1, Alk3/BMPR1A, Alk4/ACVR1B, Alk5/TGFBRI, Alk6/BMPR1B and Alk7/ACVR1C.

Activin A is found in FOP fibroblasts. Sequestration of activin A in validated mouse models of FOP have demonstrated near eradication of subsequent lesions. Muscle injury in a mouse model of FOP (Acvr1[R206H]) results in HO that can be completely abrogated using an activin A blocking antibody (Hatsell et al. Sci Transl Med. Sep. 2 2015; 7(303):303ra137). Effective attenuation of FOP HO with pharmacologic inhibition of activin A via an anti-activin A neutralizing antibody REGN2477 has also been demonstrated (Upadhyay et al., 2017, J Bone Mineral Res 32(12): 2489-2499).

However, recent literature has identified a contrast between tHO and FOP, namely the ACVR1 gene conferring a net gain-of-function and novel activation by activin A as the primary driving force behind FOP lesions.

The present experiment evaluated the effect of an anti-ACVR1 antibody of the invention and an anti-activin A antibody in an in vivo post-traumatic HO model in mice. Specifically, post-traumatic heterotopic ossification was measured by microCT analysis in mice after treatment with anti-ACVR1 antibody mAb27242.

Recombinant Proteins and Antibody Dosing of Mice

A human Acvr1 antibody (mAb27242 according to the present invention and a neutralizing antibody generated against human activin A (US Patent Application 20150037339) were employed. ALK3-Fc was also employed in post-traumatic HO formation to investigate potential inhibitory impact of inhibiting several of the osteogenic BMPs. Alk3-Fc was generated in house, in CHO cells and purified. Alk3-Fc consists of the extracellular domain of Alk3 (Swiss Prot #P27037 Q24-R152) linked to the human IgG1 Fc domain (D104-K330).

For treatment studies mice were separated to ensure age matching across groups, treatments were initiated on the same day as injury. Mice (n=15/group) were injected subcutaneously (s.c.) weekly with 25 mg/kg of an activin A blocking antibody, or isotype-control antibody. For the second experiment mice (n=12/group) were injected s.c. with 10 mg/kg of the Acvr1 blocking antibody, Alk3-Fc or an isotype control antibody. HO formation was monitored by in vivo microCT imaging over a period of at least 13 weeks.

Burn/Tenotomy Injury Model

Mice evaluated for ectopic bone were wild type (WT) C57BLJ6J mice (Jackson Laboratories). Briefly, WT mice were injected with tamoxifen for 5 days @ 40 mg/kg i.p., to initiate model. All mice received presurgical analgesia consisting of 0.06 mg·kg-1 buprenorphine for 48h, followed by anesthesia with inhaled isoflurane, and close postoperative monitoring with analgesic administration. Mice received 30% total body surface area partial-thickness burn on a shaved dorsum followed by transection of the left Achilles tendon. Dorsal burn was induced using a metal block heated to 60° C. in a water bath and applied to the dorsum for 18 s continuously. HO anlagen was observed by week 3 with mature bone formation visible by microCT by 9 weeks.

Results

Acvr1 blocking antibodies or Alk3-Fc attenuated HO in the post-traumatic HO model in mice; however, inhibition of activin A does not alter HO formation.

Figure 1B:
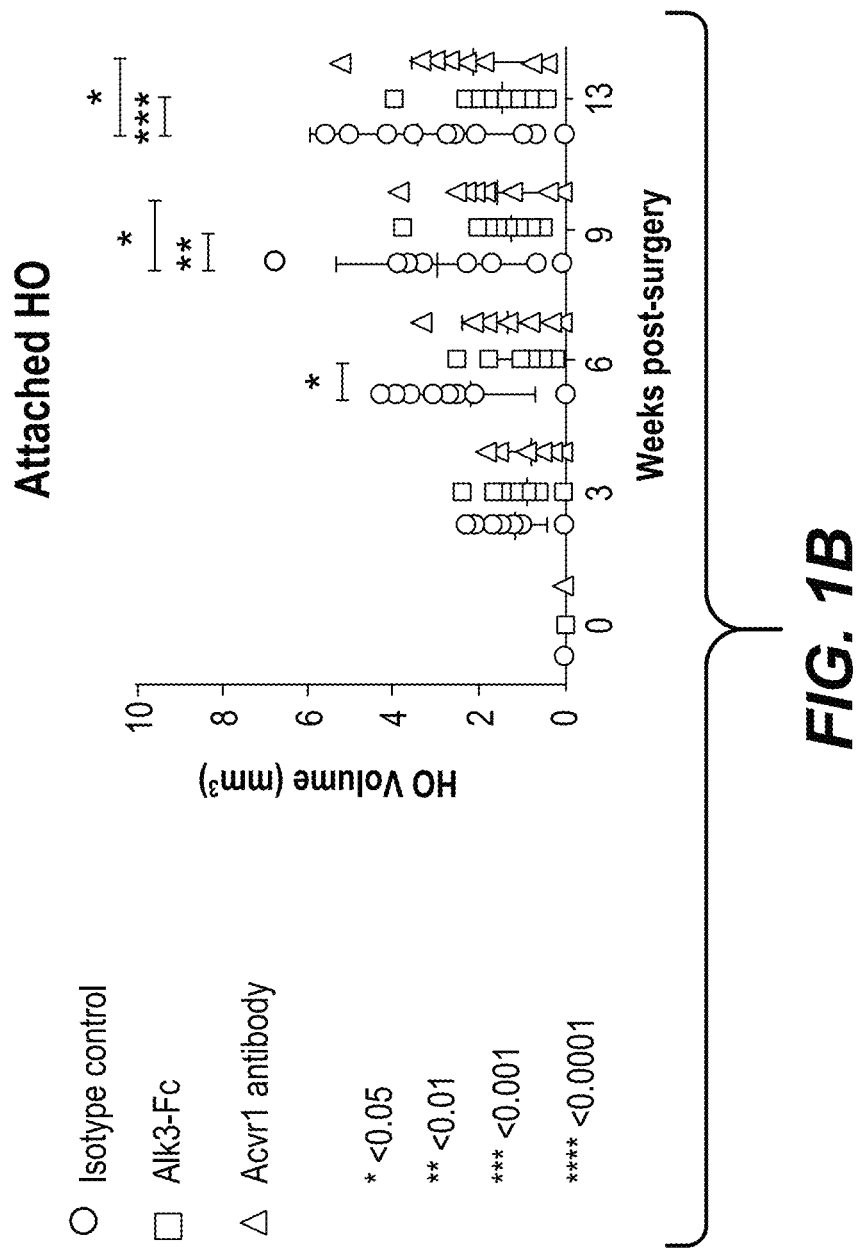
FIG. 1B shows a graph of attached heterotopic ossification (HO) volume by microCT over a period of 13 weeks after surgery in an in vivo post-traumatic HO model in WT mice. Mice were administered either an isotype control antibody (circles, n=12), ALK3-Fc (squares, n=12) or an Acvr1 antibody mAb27242 (triangles, n=12) starting concurrently with induction of injury. HO volume was measured by pCT 3, 6, 9 and 13 weeks post injury. Acvr1 blocking antibodies significantly attenuated attached HO compared to isotype control by 9 weeks post-surgery (p<0.05).
Figure 1C:
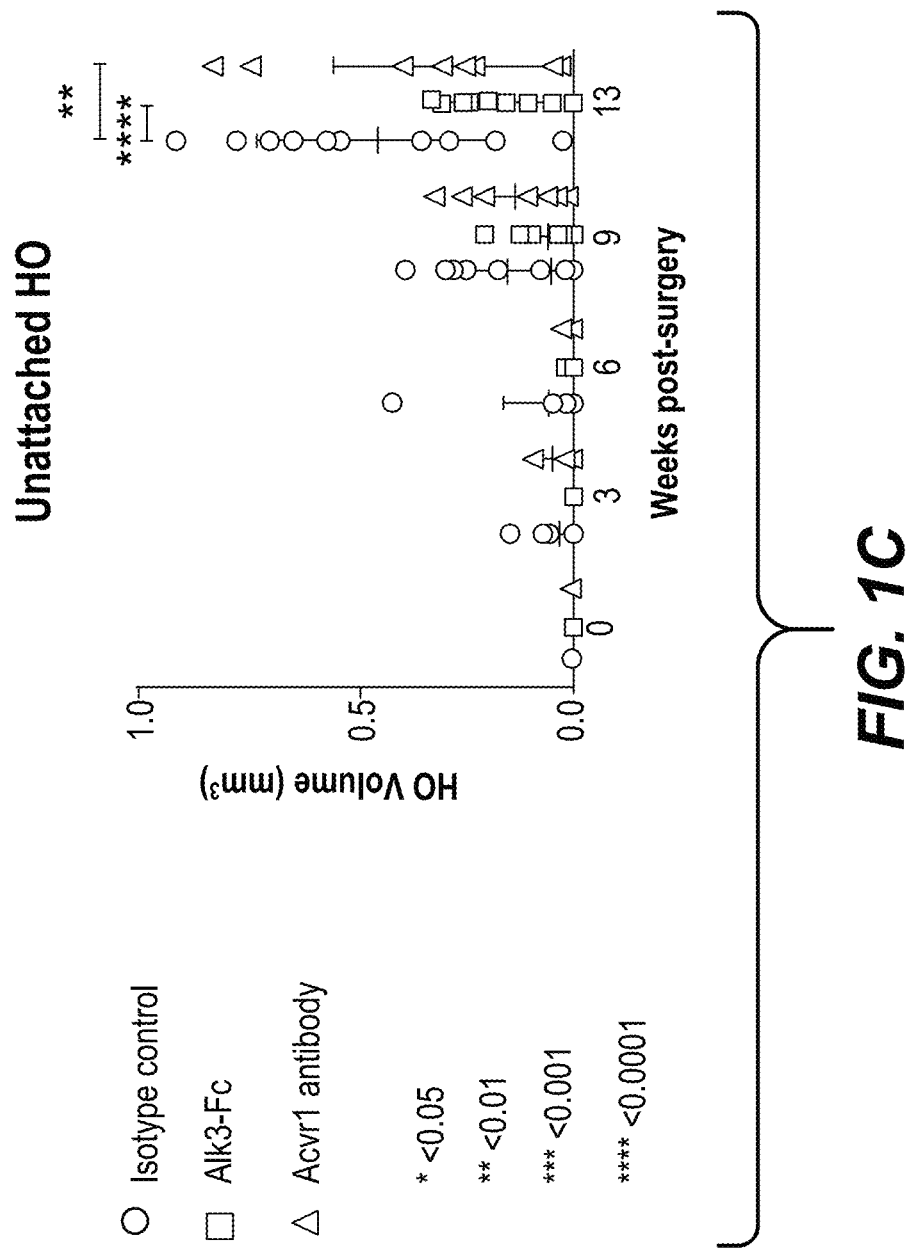
FIG. 1C shows a graph of unattached heterotopic ossification (HO) volume by microCT over a period of 13 weeks after surgery in an in vivo post-traumatic HO model in WT mice. Mice were administered either an isotype control antibody (circles, n=12), ALK3-Fc (squares, n=12) or an Acvr1 antibody mAb27242 (triangles, n=12) starting concurrently with induction of injury. HO volume was measured by pCT 3, 6, 9 and 13 weeks post injury. Acvr1 blocking antibodies significantly attenuated attached HO compared to isotype control by 13 weeks post-surgery (p<0.01).

Mice were administered either isotype control (n=12) or anti-ACVR (n=12) antibodies or Alk3-Fc (n=12) starting concurrently with induction of injury in the tHO model. FIGS. 1A-C show results of microCT analysis in mice that were administered either an isotype control antibody (circles, n=12), ALK3-Fc (squares, n=12) or an Acvr1 antibody (triangles, n=12) (mAb27242) starting concurrently with induction of injury. Total HO (FIG. 1A), attached HO (FIG. 1B), and unattached HO (FIG. 10) volumes were measured by microCT analysis at 3, 6, 9 and 13 weeks post injury.

In wild type mice induced with burn/tenotomy injury, inhibition of ACVR1 using a blocking antibody decreased HO formation by 40% (3.92 mm 3 vs 2.4 mm 3 total HO at week 13) demonstrating that at least some of the BMP signal responsible for HO formation and growth was transmitted through ACVR1. (FIGS. 1A-C). Acvr1 blocking antibodies significantly attenuated total HO (FIG. 1A) and attached HO (FIG. 1B) compared to isotype control by 9 weeks post-surgery (p<0.05). Acvr1 blocking antibodies significantly attenuated unattached HO (FIG. 10) compared to isotype control by 13 weeks post-surgery (p<0.01).

In wild type mice induced with burn/tenotomy injury, ALK3-Fc reduced, but did not completely inhibit, HO by 60% (3.92 mm 3 vs 1.63 mm 3 total HO at week 13) consistent with previously published data (Agarwal et al. Mol Ther. Aug. 2 2017; 25(8):1974-87) (FIG. 1A). Alk3-Fc significantly attenuated total HO (FIG. 1A) and attached HO (FIG. 1B) compared to isotype control by 6 weeks post-surgery (p<0.05). Alk3-Fc also significantly attenuated unattached HO (FIG. 10) compared to isotype control by 13 weeks post-surgery (p<0.0001).

Figures 2A, 2B, 2C:
FIGS. 2A-C show images of HO volume in the injured hindlimb in an in vivo post-traumatic HO model in WT mice as measured by total HO volume by microCT, attached HO (encircled by broken white lines) or unattached HO (encircled by short dashed white lines) 13 weeks post-surgery.

Images of HO volume in the injured hindlimb in WT mice as measured by total HO volume, attached HO (encircled by broken white lines) or unattached HO (encircled by short dashed white lines) are shown in FIGS. 2A-C. HO volumes by micro CT were significantly reduced after 13 weeks in both ALK3-Fc (FIG. 2B) and Acvr1 antibody (FIG. 2C) treated mice compared to isotype control (FIG. 2A). Total HO volume and attached HO volume was significantly reduced by 6 or 9 weeks post injury in the Alk3-Fc and Acvr1 antibody treated groups respectively.

In addition, WT mice were administered either activin A (n=15) antibodies or isotype control (n=15) starting concurrently with induction of injury in the burn/tenotomy injury model. HO volume was measured by microCT analysis 9 weeks post injury. HO volume in the injured hindlimb as measured by total volume, attached HO volume, or unattached HO volume was not significantly different between treatment groups. Activin A inhibition did not reduce HO formation or growth. Further stratification of floating and bone associated HO also did not demonstrate a difference between activin A treated and vehicle control treated animals (data not shown).

This example shows Acvr1 blocking antibodies significantly attenuate HO in an in vivo post-traumatic HO model; however, no significant effect of anti-activin A antibody was observed.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. An isolated antibody or antigen-binding fragment thereof that binds specifically to activin A receptor type 1 (ACVR1) protein and/or a mutant thereof, wherein the antibody or antigen-binding fragment thereof interacts with one or more amino acids contained within the extracellular domain of ACVR1 (amino acids 21-123 of SEQ ID NO: 341), and wherein the antibody or antigen-binding fragment thereof binds to cells expressing full-length ACVR1 protein and/or a mutant thereof,
  wherein the antibody or antigen-binding fragment thereof comprises
  three heavy chain complementarity determining regions (CDRs) (HCDR1, HCDR2 and HCDR3) contained within a heavy chain variable region (HCVR) comprising the amino acid sequence of SEQ ID NO: 42; and three light chain CDRs (LCDR1, LCDR2 and LCDR3) contained within a light chain variable region (LCVR) comprising the amino acid sequence of SEQ ID NO: 48; or
  three heavy chain CDRs (HCDR1, HCDR2 and HCDR3) contained within a HCVR comprising the amino acid sequence of SEQ ID NO: 58; and three light chain CDRs (LCDR1, LCDR2 and LCDR3) contained within a LCVR comprising the amino acid sequence of SEQ ID NO: 62.

2. The isolated antibody or antigen-binding fragment of claim 1, wherein the full-length ACVR1 protein or mutant thereof is a full-length human ACVR1 protein or mutant thereof.

3. The isolated antibody or antigen-binding fragment thereof of claim 2, wherein the full-length human ACVR1 protein comprises amino acids 21-509 of SEQ ID NO: 341.

4. The isolated antibody or antigen-binding fragment thereof of claim 1, wherein the mutant ACVR1 protein comprises a mutation selected from the group consisting of ACVR1 L196P, delP197_F198insL, R202I, R206H, Q207E, R258S, R258G, G325A, G328E, G328R, G328W, G356D, and R375P of SEQ ID NO: 341.

5. The isolated antibody or antigen-binding fragment of claim 4, wherein the isolated antibody or antigen-binding fragment thereof binds to ACVR1(R206H) protein and inhibits ACVR1(R206H)-mediated bone morphogenetic protein (BMP) signal transduction.

6. The antibody or antigen-binding fragment thereof of claim 1, wherein the antibody has one or more properties selected from the group consisting of:
  (a) is a fully human monoclonal antibody; (b) binds to human ACVR1 extracellular domain fused to an Fc (e.g., SEQ ID NO: 339) at 25° C. with a dissociation constant ($K_D$) of less than 60 nM, less than 12 nM, less than less than 2 nM, less than 1 nM, or less than 0.5 nM as measured in a surface plasmon resonance assay; (c) binds to human ACVR1 extracellular domain fused to mFc (SEQ ID NO: 339) at 37° C. with a dissociation constant ($K_D$) of less than 150 nM, less than nM, less than less than 5 nM, less than 1.5 nM, or less than 1 nM as measured in a surface plasmon resonance assay; (d) binds to human ACVR1 extracellular domain fused to myc-myc-hexahistag (e.g., SEQ ID NO: 338) at 25° C. with a $K_D$ of less than 300 nM, less than 150 nM, less than 25 nM, less than 10 nM, less than 5 nM, less than 3 nM or less than 2 nM as measured in a surface plasmon resonance assay; (e) binds to human ACVR1 extracellular domain fused to myc-myc-hexahistag (e.g., SEQ ID NO: 338) at 37° C. with a $K_D$ of less than 500 nM, less than 50 nM, less than 25 nM, less than 10 nM, as measured in a surface plasmon resonance assay; (f) does not bind mouse ACVR1 or binds to mouse ACVR1 extracellular domain fused to myc-myc-hexahistag (e.g., SEQ ID NO: 340) at 25° C. with a $K_D$ of greater than 500 nM, as measured in a surface plasmon resonance assay; (g) does not bind mouse ACVR1 or binds to mouse ACVR1 extracellular domain fused to myc-myc-hexahistag (e.g., SEQ ID NO: 340) at 37° C. with a $K_D$ of greater than 500 nM, as measured in a surface plasmon resonance assay; (k) binds to cells expressing human ACVR1 protein or human ACVR1 (R206H) protein; (l) inhibits activation of cells expressing human ACVR1(R206H) by human Activin A with a $IC_{50}$ of less than 25 nM, as measured in a cell-based bioassay; (m) inhibits activation of cells expressing human ACVR1(R206H) by human BMP7 with a $IC_{50}$ of less than 20 nM, less than 5 nM, less than 3 nM, or less than 1 nM, or less than as measured in a cell-based bioassay; (m) significantly decreases serum hepcidin when administered to mice expressing human ACVR1 in place of mouse allele; (n) significantly increases serum iron levels when administered to mice expressing human ACVR1 in place of mouse allele; and/or (o) inhibits wild-type ACVR1 signaling when administered to mice expressing human ACVR1 in place of mouse allele; and (p) comprises a HCVR/LCVR amino acid sequence pair selected from the group consisting of SEQ ID NOs: 42/48 and 58/62.

7. The antibody or antigen-binding fragment thereof of claim 1 comprising:
  (a) a HCDR1 domain having the amino acid sequence of SEQ ID NO: 44;
  (b) a HCDR2 domain having the amino acid sequence of SEQ ID NO: 46;
  (c) a HCDR3 domain having the amino acid sequence of SEQ ID NO: 28;
  (d) a LCDR1 domain having the amino acid sequence of SEQ ID NO: 50;
  (e) a LCDR2 domain having the amino acid sequence of SEQ ID NO: 52; and
  (f) a LCDR3 domain having the amino acid sequence of SEQ ID NO: 36.

8. The antibody or antigen-binding fragment thereof of claim 7 comprising the HCVR/LCVR amino acid sequence pair of SEQ ID NOs: 42/48.

9. The antibody or antigen-binding fragment thereof of claim 1 comprising: (a) a HCDR1 domain having the amino acid sequence of SEQ ID NO: 24; (b) a HCDR2 domain having the amino acid sequence of SEQ ID NO: 46; (c) a HCDR3 domain having the amino acid sequence of SEQ ID NO: 60; (d) a LCDR1 domain having the amino acid sequence of SEQ ID NO: 50; (e) a LCDR2 domain having the amino acid sequence of SEQ ID NO: 64; and (f) a LCDR3 domain having the amino acid sequence of SEQ ID NO: 66.

10. The antibody or antigen-binding fragment thereof of claim 9 comprising a HCVR/LCVR amino acid sequence pair of SEQ ID NOs: 58/62.

11. A pharmaceutical composition comprising an isolated antibody or antigen-binding fragment thereof that binds to ACVR1 according to claim 1 and a pharmaceutically acceptable carrier or diluent.

12. An antibody or antigen-binding fragment thereof that binds to ACVR1, wherein the antibody or antigen-binding fragment comprises
- three heavy chain CDRs (HCDR1, HCDR2 and HCDR3) contained within a HCVR comprising the amino acid sequence of SEQ ID NO: 42, and three light chain CDRs (LCDR1, LCDR2 and LCDR3) contained within a LCVR comprising the amino acid sequence of SEQ ID NO: 48; or
- three heavy chain CDRs (HCDR1, HCDR2 and HCDR3) contained within a HCVR comprising the amino acid sequence of SEQ ID NO: 58; and three light chain CDRs (LCDR1, LCDR2 and LCDR3) contained within a LCVR comprising the amino acid sequence of SEQ ID NO: 62.

13. The antibody or antigen-binding fragment thereof of claim 12 comprising:
(a) a HCDR1 domain having the amino acid sequence of SEQ ID NO: 44;
(b) a HCDR2 domain having the amino acid sequence of SEQ ID NO: 46;
(c) a HCDR3 domain having the amino acid sequence of SEQ ID NO: 28;
(d) a LCDR1 domain having the amino acid sequence of SEQ ID NO: 50;
(e) a LCDR2 domain having the amino acid sequence of SEQ ID NO: 52; and
(f) a LCDR3 domain having the amino acid sequence of SEQ ID NO: 36.

14. The antibody or antigen-binding fragment thereof of claim 13 comprising a HCVR having the amino acid sequence of SEQ ID NO: 42, and a LCVR having the amino acid sequence of SEQ ID NO: 48.

15. The antibody or antigen-binding fragment thereof of claim 12 comprising: (a) a HCDR1 domain having the amino acid sequence of SEQ ID NO: 24; (b) a HCDR2 domain having the amino acid sequence of SEQ ID NO: 46; (c) a HCDR3 domain having the amino acid sequence of SEQ ID NO: 60; (d) a LCDR1 domain having the amino acid sequence of SEQ ID NO: 50; (e) a LCDR2 domain having the amino acid sequence of SEQ ID NO: 64; and (f) a LCDR3 domain having the amino acid sequence of SEQ ID NO: 66.

16. The antibody or antigen-binding fragment thereof of claim 15 comprising a HCVR having the amino acid sequence of SEQ ID NO: 58, and a LCVR having the amino acid sequence of SEQ ID NO: 62.

17. An isolated monoclonal antibody or antigen-binding fragment thereof that inhibits ACVR1-mediated and/or ACVR1(R206H)-mediated bone morphogenetic protein (BMP) signal transduction
- wherein the antibody or antigen-binding fragment thereof comprises
- three heavy chain CDRs contained within a HCVR comprising the amino acid sequence of SEQ ID NO: 42; and three light chain CDRs contained within a LCVR comprising the amino acid sequence of SEQ ID NO: 48; or
- three heavy chain CDRs contained within a HCVR comprising the amino acid sequence of SEQ ID NO: 58; and three light chain CDRs contained within a LCVR comprising the amino acid sequence of SEQ ID NO: 62.

18. The antibody or antigen-binding fragment thereof of claim 17 comprising the CDR amino acid sequences of SEQ ID NOs: 44, 46, 28, 50, 52, and 36.

19. The antibody or antigen-binding fragment thereof of claim 18 comprising the HCVR/LCVR amino acid sequence pair of SEQ ID NOs: 42/48.

20. The antibody or antigen-binding fragment thereof of claim 17 comprising the CDR amino acid sequences of SEQ ID NOs: 24, 46, 60, 50, 64, and 66.

21. The antibody or antigen-binding fragment thereof of claim 20 comprising the HCVR/LCVR amino acid sequence pair of SEQ ID NOs: 58/62.

* * * * *